United States Patent
Dockal et al.

(10) Patent No.: US 9,417,251 B2
(45) Date of Patent: Aug. 16, 2016

(54) METHODS AND SYSTEMS FOR SCREENING COMPOSITIONS COMPRISING NON-ANTICOAGULANT SULFATED POLYSACCHARIDES

(71) Applicants: Baxter International Inc., Deerfield, IL (US); Baxter Healthcare S.A., Glattpark (Opfikon) (CH)

(72) Inventors: Michael Dockal, Vienna (AT); Friedrich Scheiflinger, Vienna (AT); Zhenqing Zhang, Deerfield, IL (US); Susanne Till, Deerfield, IL (US); Sabine Knappe, Deerfield, IL (US); Christina Szabo, Deerfield, IL (US)

(73) Assignees: Baxalta GmbH, Glattpark (CH); Baxalta Incorporated, Deerfield, IL (US)

( * ) Notice: Subject to any disclaimer, the term of this patent is extended or adjusted under 35 U.S.C. 154(b) by 278 days.

(21) Appl. No.: 13/964,684

(22) Filed: Aug. 12, 2013

(65) Prior Publication Data

US 2014/0051657 A1    Feb. 20, 2014

Related U.S. Application Data

(60) Provisional application No. 61/683,144, filed on Aug. 14, 2012.

(51) Int. Cl.
*G01N 33/86* (2006.01)

(52) U.S. Cl.
CPC .................. *G01N 33/86* (2013.01)

(58) Field of Classification Search
CPC ...................................... G01N 33/86
See application file for complete search history.

(56) References Cited

U.S. PATENT DOCUMENTS

| | | | |
|---|---|---|---|
| 4,431,546 A | 2/1984 | Hughes et al. | |
| 6,593,311 B2 | 7/2003 | Sakai et al. | |
| 7,829,549 B2 | 11/2010 | Johnson | |
| 2003/0203845 A1 | 10/2003 | Knudsen et al. | |
| 2005/0282771 A1 | 12/2005 | Johnson | |
| 2005/0282775 A1 | 12/2005 | Kennedy | |
| 2006/0088912 A1 | 4/2006 | Yan et al. | |
| 2007/0218076 A1 | 9/2007 | Michailovna et al. | |
| 2008/0107678 A1 | 5/2008 | Johnson | |
| 2009/0098185 A1 | 4/2009 | Johnson | |
| 2009/0269325 A1 | 10/2009 | Johnson | |
| 2011/0110921 A1 | 5/2011 | Dockal et al. | |

FOREIGN PATENT DOCUMENTS

| | | |
|---|---|---|
| CN | 1344565 | 4/2002 |
| CN | 1320002 | 1/2006 |
| EP | 0251134 | 5/1989 |
| EP | 1327448 | 6/2005 |
| JP | 7215990 | 8/1995 |
| JP | 2002262788 | 9/2002 |
| JP | 3371124 | 1/2003 |
| JP | 410324508 | 6/2003 |
| JP | 2003171262 | 6/2003 |
| WO | WO9815292 | 4/1998 |
| WO | WO9918961 | 4/1999 |
| WO | WO2004029095 | 4/2004 |
| WO | WO2005117912 | 12/2005 |
| WO | WO2007127298 | 11/2007 |
| WO | WO2008090631 | 7/2008 |
| WO | WO2008103234 | 8/2008 |
| WO | WO2010020423 | 2/2010 |

OTHER PUBLICATIONS

Bates, et al., "The new heparins", Cornary Artery Disease, 1998, vol. 9, No. 2-3, 65-74.
Bishop, et al., "Recombinant biologics for treatment of bleeding disorders" Nat Rev Drug Discov. 2004;3(8):684-94.
Bourin, et al., "Glycosaminoglycans and the regulation of blood coagulation", Biochem J. 1993; 289(Pt 2): 313-330.
Broze, et al., "The role of tissue factor pathway inhibitor in a revised coagulation cascade", Semin Hematol. 1992;29(3):159-69.
Broze, GJ Jr. "The rediscovery and isolation of TFPI", J Thromb Haemost. 2003;1(8):1671-5.
Brummel., "Factor VIIa replacement therapy in factor VII deficiency", J Thromb Haemost. 2004;2(10):1735-44.
Carcao, et al., "Prophylactic factor replacement in hemophilia", Blood Rev. 2004;18(2):101-13.
Colliec, et al., "Anticoagulant properties of a fucoïdan fraction", Thromb Res. 1991; 15;64(2):143-54.
Church, et al., "Antithrombin Activity of Fucoidan. The Interaction of Fucoidan With Heparin Cofactor II, Antithrombin III, and Thrombin," J. Bioi. Chem., 1989; 264(6):3618-23.
Davie, et al., "The Coagulation Cascade: Initiation, Maintenance, and Regulation," Biochemistry, 1991;30(43):10363-70.
Erhardtsen, et al., "Blocking of Tissue Factor Pathway Inhibitor (TFPI) Shortens the Bleeding Time in Rabbits With Antibody Induced Haemophilia A," Blood Coagul. Fibrinolysis, 1995;2(5):388-94.
Fryer, et al., "Selective O-Desulfation Produces Nonanticoagulant Heparin That Retains Pharmacological Activity in the Lung," J Pharmacol £xp Ther., 1997;m(I):208-19.
Fogarty, Patrick F., "Biological rationale for new drugs in the bleeding disorders pipeline", Hematology Am Soc Hematol Educ Program, 2011; 397-404.

(Continued)

*Primary Examiner* — Amber D Steele
(74) *Attorney, Agent, or Firm* — Bozicevic, Field & Francis LLP; Bret E. Field

(57) ABSTRACT

Aspects of the invention include methods for identifying one or more NASP (non-anticoagulant sulfated polysaccharide) compositions that are suitable for treating a subject having a blood coagulation disorder. In practicing methods according to certain embodiments, NASP compositions are evaluated by determining the coagulation activity and chemical makeup of the NASP composition and the molecular structure of the NASP. Systems for practicing methods of the invention as well as compositions suitable for treating a subject having a blood coagulation disorder are also described.

21 Claims, 22 Drawing Sheets

(56) References Cited

OTHER PUBLICATIONS

Gao, et al., "Development of column-pretreatment chelating resins for matrix elimination/multi-element determination by inductively coupled plasma-mass spectrometry", Analyst. 2002;127(12):1713-9.
Gailani, et al., "Factor XI activation in a revised model of blood coagulation", Science. 1991 ;253(5022):909-12.
Giedrojc, et al., "Comparative Study on the In Vitro and In Vivo Activities of Heparinoids Derivative Investigated on the Animal Model," J. Cardiovasc. Pharmacol., 1999;34(3):340-5.
Goodman-Gilman, "The Pharmacological Basis of Therapeutics" editors Joel G. Hardman and Lee E. Limbard; published by The McGraw-Hill Companies Inc., 2001, 54-56.
Granert, et al., "Effects of Polysaccharide Fucoidin on Cerebrospinal Fluid Interleukin-I and Tumor Necrosis Factor Alpha in Pneumococcal Meningitis in the Rabbit," Irifect. Immun., 1999;67(5):2071-4.
Hirsh, et al., "New Anticoagulants," Blood, 2005;W(2):453-63.
Irhimeh et al., "Pilot clinical study to evaluate the anticoagulant activity of fucoidan", Blood Coagulation and Fibrinolysis, 2009, vol. 20, No. 7, pp. 607-610.
Johnson, et al., "Novel Anticoagulants Based on Inhibition of the Factor ViialTissue Factor Pathway," Coron. Artery. Dis., 1998; 2(2-3):83-7.
Johnson, et al., "Discovery of tight junction modulators: significance for drug development and delivery", Drug Discov Today, 2008;13(5-6):261-7.
Kim et al., "A 4-week repeated oral dose toxicity study of fucoidan from the Sporophyll of Undaria pinnatifida in Sprague-Dawley rats", Toxicology,2010, vol. 267, No. 1-3, pp. 154-158.
Kitamura, et al., "Fucoldan from Brown Seaweed Laminaria angustata var. longissima" Agricultural and Biological Chemistry, 1991, vol. 55, No. 2, 1991, Tokyo JP, pp. 615-616.
Kleesiek, et al., "The 536C-->T Transition in the Human Tissue Factor Pathway Inhibitor (TFPJ) Gene Is Statistically Associated With a Higher Risk for Venous Thrombosis," Thromb. Haemost., 1999;82(1):1-5.
Kleim, et al., "Successful renal transplantation in severe von Willebrand's disease", Oxford Journals Medicine, Nephrology Dialysis Transplantation, 1994, vol. 9, issue 7, 837-838.
Lee, "Von Willebrand Disease, Hemophilia A and B, and Other Factor Deficiencies," Int. Anesthesiol. Clin., 2004;42(3):59-76.
Li et al., "Fucoidan: structure and bioactivity" Molecules, 2008, vol. 13, No. 8 pp. 1671-1695.
Li et al, "Toxicological Evaluation of Ducoidian Extracted from Laiminara Japonica in Wistar Rats" Foo Chem Toxicol, 2005;43:421-426.
Life Extension, Optimized Fucoidan with Maritech 926, http://www.lef.org/Vitamins-Supplements/Item01513/Optimized-Fucoidan-with-Maritech-926.html, catalog No. 01513, 1995-2013.
Liu, et al., "Improved coagulation in bleeding disorders by Non-Anticoagulant Sulfated Polysaccharides (NASP)," Thrombosis and Haemostasis,2006;95:68-76.
Luyt, et al., "Low-Molecular-Weight Fucoidan Promotes Therapeutic Revascularization in a Rat Model of Critical Hindlimb Ischemia," J. Pharmacol. Exp. Ther., 2003;305(1):24-30.
MacGregor, et al., "Metabolism of Sodium Pentosan Polysulphate in Man Measured'by a New Competitive Binding Assay for Sulphated Polysaccharides—Comparison With Effects Upon Anticoagulant Activity, Lipolysisand Platelet Alpha-Granule Proteins," Thromb. Haemost., 1985;53(3):4II-4.
Mabeau, et al,. "Fractionation and Analysis of Fucans From Brown Algae", Phytochemistry (Oxford), 1990, vol. 29, No. 8, pp. 2441-2446.
Mann, "Thrombin: Can't Live Without It; Probably Die From It," Chest 124(3 Suppl), 2003:IS-3S.
Mann, "Thrombin Formation," Chest 124(3 Suppl) 2003:4S-10S.
Marais, et al., "A fucoidan fraction from Ascophyllum nodosum", Carbohydrate Research, Elsevier Scientific Publishing Company, 2001, vol. 336, No. 2, pp. 155-159.
McAuliffe, et al., "Carbohydrate drugs—an ongoing challenge", Chem.Indus., Magazine, 1997;2:170-4.
McCaffrey et al., "Fucoidan is a non-Anticoagulant inhibitor of intimal hyperplasia", Biochem. Biophys. Res. Commun., 1992;184(2):773-81.
Millet, et al. "Antithrombotic and Anticoagulant Activities of a Low Molecular Weight Fucoidan by the Subcutaneous Route", Thromb. Haemost.,1999;81:391-5.
Mourao, "Use of Slfated Fucans as Anticoagulant and Antithombotic Agents: Future Perspectives" Curr Pharma Des., 2004;10: 967-981.
Nagaoka, et al., "Structural study of fucoidan from Cladosiphon okamuranus tokida", Glycoconjugate Journal, 1999, vol. 16, Issue 1,19-26.
National Research Council, "Guide for the Care and Use of Laboratory Animals", by Institute of Laboratory Animal Resources, National Research Council, Nat. Acad. Press, 1996.
Nishino, et al., "Isolation and partial characterization of a novel amino sugar-containing fucan sulfate from commercial Fucus vesiculosus fucoidan", Carbohydr Res. 1994;4;255:213-24.
Nordfang, et al. "Inhibition of Extrinsic Pathway Inhibitor Shortens the Coagulation Time of Normal Plasma and of Hemophilia Plasma," Thromb. Haemost.,1991;66(4):464-67.
Novotny, et al. "Purification and Properties of Heparin-Releasable Lipoprotein-Associated Coagulation Inhibitor," Blood, 1991;78(2):394-400.
Official Action in U.S. Appl. No. 11/140,504, Mail Date Aug. 4, 2008, 41 pages.
Official Action in U.S. Appl. No. 11/140,504, Mail Date Mar. 16, 2009, 162 pages.
Official Action in U.S. Appl. No. 12/316,632, Mail Date Jun. 25, 2009, 21 pages.
Official Action in U.S. Appl. No. 13/111,684, Mail Date Jan. 27, 2012, 27 pages.
Official Action in U.S. Appl. No. 12/449,712, Mail Date Apr. 2, 2012, 101 pages.
Official Action in U.S. Appl. No. 12/893,798, Mail Date May 2, 2012, 54 pages.
Official Action in U.S. Appl. No. 13/111,684, Mail Date Jul. 2, 2012, 18 pages.
Official Action in U.S. Appl. No. 12/893,798, Mail Date Aug. 10, 2012, 33 pages.
Official Action in U.S. Appl. No. 12/449,712, Mail Date Oct. 5, 2012, 13 pages.
Orgueira, et al. "Modular Synthesis of Heparin Oligosaccharides," Chem. Eur. J., 2003; 2(1):140-69.
Prasad et al., "Efficacy and safety of a new-class hemostatic drug candidate, AV513, in dogs with homphilia A" Blood, 2008, vol. 111, No. 2, 672-679.
Pipe, Steven W., "Hemophilia: new protein therapeutics", Hematology Am Soc Hematol Educ Program, 2010:203-9.
Rapaport, et al., "The Tissue Factor Pathway: How It Has Become a 'Prima Ballerina'," Thromb. Haemost., 1995;74(1):7-17.
Roberts, et al., "Current Concepts of Hemostasis: Implications for Therapy," Anesthesiology, 2004;100(3):722-30.
Schaub, Robert G., "Recent advances in the development of coagulation factors and procoagulants for the treatment of hemophilia", Biochem Pharmacol. 2011;15;82(2):91-8.
Sinay, Pierre, "Sugars Slide Into Heparin Activity," Nature, 1999;398(6726):377-8.
Springer, et al., "Isolation of anticoagulant fractions from crude fucoidin", Proc Soc Exp Biol Med. 1957;94(2):404-9.
Sukuki, et al., "Adsorption and removal of oxo-anions of arsenic and selenium on the zirconium(IV) loaded polymer resin functionalized with diethylenetriamine-N,N,N',N'-polyacetic acid", J Environ Monit. 2000;2(6):1 page.
Thanou, et al., "Mono-N-carboxymethyl chitosan (MCC), a polyampholytic chitosan derivative, enhances the intestinal absorption of low molecular weight heparin across intestinal epithelia in vitro and in vivo", J Pharm Sci. 2001;90(1):38-46.
Toida ei al. "Structure and Bioactivity of Sulfated Polysaccarides", Trends in Glyoeseienee and Glyeoteehnology, 2003;15(81):29-46.
Van't Veer, et al., "Regulation of Tissue Factor Initiated Thrombin Generation by the Stoichiometric Inhibitors Tissue Factor Pa thwa y Inhibitor, Antithrombin-III, and Heparin Cofactor-II", Journal of

(56) References Cited

OTHER PUBLICATIONS

Biological Chemistry, American Society of Biolochemical Biologists, Birmingham, 1997;US, 272(7):4367-4377.
Vicente, et al., "Unbalanced Effects of 1-23 Dermation Sulfates With Different Sulfation Patterns on Coagulation, Thrombosis and Bleeding," Thromb Haenos, 2001 86(5): 121 5-1220.
Wang, et al., "N-Desulfated Non-Anticoagulant Heparin Inhibits Leukocyte Adhesion and Transmigration In Vitro and Attenuates Acute Peritonitis and Ischemia and Reperfusion Injury In Vivo," Inflamm. Res., 2002;51(9):435-43.
Welsch, et al., "Effect of lipoprotein-associated coagulation inhibitor (LACI) on thromboplastin-induced coagulation of normal and hemophiliac plasmas", Thromb. Res., 1991 ;64(2):213-22.
Westrick, et al., "Deficiency of Tissue Factor Pathway Inhibitor Promotes Atherosclerosis and Thrombosis in Mice," Circulation, 2001; 103(25):3044-6.
Williams, et al., "Comparative Effects of Heparin and the Sulfatoid GMI474 on Coagulation parameters in Plasma and Blood From Various Species," Gen. Pharmacol., 1998; 30(3):337-41.
Wuilllemin, et al., "Thrombin-mediated activation of endogenous factor XI in plasma in the presence of physiological glycosaminoglycans occurs only with high concentrations of thrombin", Br J Haematol.,1996;92(2):466-72.

Anticoagulant Activity of NASP Compositions by Activated Partial Thromboplastin Time Assay (aPTT)

Activation of the Contact Pathway

Inhibition of Tissue Factor Pathway Inhibitor
Dilute Prothrombin Time (dPT)

Molecular Structure by ¹³Carbon Nuclear Magnetic Resonance Spectroscopy

Overlaid $^1$H and $^{13}$C NMR spectra of size-separated fractions of *F.v.* fucoidan.

3-D HSQC-TOCSY NMR Spectroscopy

Sulfation and Glycosidic Bond Configuration

Residues A and B

Major structures of Fraction C6

Where $R_1$ = $SO_3Na$ (8%, mol%) or H (92%, mol%); n ≈ 276; m ≈ 191. These numbers were calculated using the sulfur content and molecular weight of this fraction.

¹H-NMR Spectroscopy of Oversulfated and Desulfated NASPs

METHODS AND SYSTEMS FOR SCREENING COMPOSITIONS COMPRISING NON-ANTICOAGULANT SULFATED POLYSACCHARIDES

CROSS-REFERENCE TO RELATED APPLICATION

Pursuant to 35 U.S.C. §119(e), this application claims priority to U.S. Provisional Application Ser. No. 61/683,144 filed on Aug. 14, 2012, the disclosure of which is herein incorporated by reference.

INTRODUCTION

Bleeding is one of the most serious and significant manifestations of disease, and may occur from a local site or be systemic. Localized bleeding may be associated with lesions and may be further complicated by a defective haemostatic mechanism. Blood clotting is inadequate in bleeding disorders, which may be caused by congenital coagulation disorders, acquired coagulation disorders, or hemorrhagic conditions induced by trauma. Congenital or acquired deficiencies of any of the coagulation factors may be associated with a hemorrhagic tendency. Congenital coagulation disorders include hemophilia, a recessive X-linked disorder involving a deficiency of coagulation factor VIII (hemophilia A) or factor IX (hemophilia B) and von Willebrand disease, a rare bleeding disorder involving a severe deficiency of von Willebrand factor. Acquired coagulation disorders may arise in individuals without a previous history of bleeding as a result of a disease process. For example, acquired coagulation disorders may be caused by inhibitors or autoimmunity against blood coagulation factors, such as factor VIII, von Willebrand factor, factors IX, V, XI, XII and XIII; or by hemostatic disorders such as caused by liver disease, which may be associated with decreased synthesis of coagulation factors.

SUMMARY

Aspects of the invention include methods for identifying one or more NASP (non-anticoagulant sulfated polysaccharide) compositions that are suitable for treating a subject having a blood coagulation disorder. In practicing methods according to certain embodiments, NASP compositions are evaluated by determining the coagulation activity and chemical makeup of the NASP composition and the molecular structure of the NASP. Systems for practicing methods of the invention as well as compositions suitable for treating a subject having a blood coagulation disorder are also described.

In some embodiments, methods include evaluating one or more NASP compositions and determining whether each NASP composition is suitable for treating a subject having a blood coagulation disorder. In other embodiments, methods include screening a plurality of NASP compositions, comparing each NASP composition with each other and identifying whether one or more of the NASP compositions may be suitable for treating a subject having a blood coagulation disorder.

In embodiments of the invention, methods include determining the coagulation activity of the composition, such as measuring the procoagulant activity and the anticoagulant activity of the composition. For instance, measuring the procoagulant activity may include assessing plasma clotting (e.g., in normal or FVIII-inhibited plasma) by calibrated automated thrombography or rotation thromboelastometry, determining the $EC_{50}$ of the composition and determining the procoagulant window of the NASP composition. Measuring the anticoagulant activity may include in certain instances, evaluating an increase in blood plasma clotting time, determining the concentration of the NASP at which a 50% increase in clotting time is observed and determining the ratio of procoagulation activity and anticoagulation activity. In other instances, determining the coagulation activity of the composition includes assessing the TFPI-inhibiting activity of the NASP. In yet other instances, determining the coagulation activity of the composition includes determining the effect of the composition on contact pathway activation.

In other embodiments, methods include determining the molecular structure of the NASP, such as determining the molecular weight of the NASP, determining the polydispersity of NASP molecular weight, determining the monosaccharide content of the NASP, determining the sulfur content of the NASP and determining the structural configuration (e.g., glycosidic bonds) of the NASP.

In yet other embodiments, methods include determining the chemical makeup of the NASP composition, such as determining the elemental composition, the non-NASP saccharide content, the protein content and the impurity content (e.g., organic and inorganic).

Aspects of the invention also include identifying one or more NASP compositions that may be suitable for treating a subject having a blood coagulation disorder based on the determined coagulation activity, chemical makeup of the NASP composition and the molecular structure of the NASP. In other embodiments, aspects also include screening a plurality of NASP compositions by comparing the determined coagulation activities, chemical makeups and molecular structures of the plurality of NASP compositions and selecting one or more of the NASP compositions that may be suitable for treating a subject having a blood coagulation disorder.

Systems for screening and evaluating one or more NASP compositions according to methods described above are also of interest. For example, systems may include input controls for inputting data based on the determined coagulation activities, chemical makeups and molecular structures of the one or more NASP compositions, processors for evaluating data obtained for each NASP composition and an output for displaying one or more NASP compositions selected as being suitable for treating a subject having a blood coagulation disorder.

BRIEF DESCRIPTION OF THE FIGURES

FIG. 5a shows procoagulant activity determined by CAT assays in FVIII-inhibited human plasma. FIG. 5b shows anticoagulant effect measured by aPTT assays. FIG. 5c shows procoagulant activity by $EC_{50}$ values derived from thrombin generation curves as a function of molecular weight. FIG. 5d shows trends observed for anticoagulant activity.

FIG. 6a shows procoagulant activity determined by CAT assays in FVIII-inhibited human plasma. FIG. 6b shows anticoagulant effect measured by aPTT assays. FIG. 6c shows procoagulant activity by $EC_{50}$ values derived from thrombin generation curves as a function of molecular weight. FIG. 6d shows trends observed for anticoagulant activity.

DETAILED DESCRIPTION

Figure 1A:
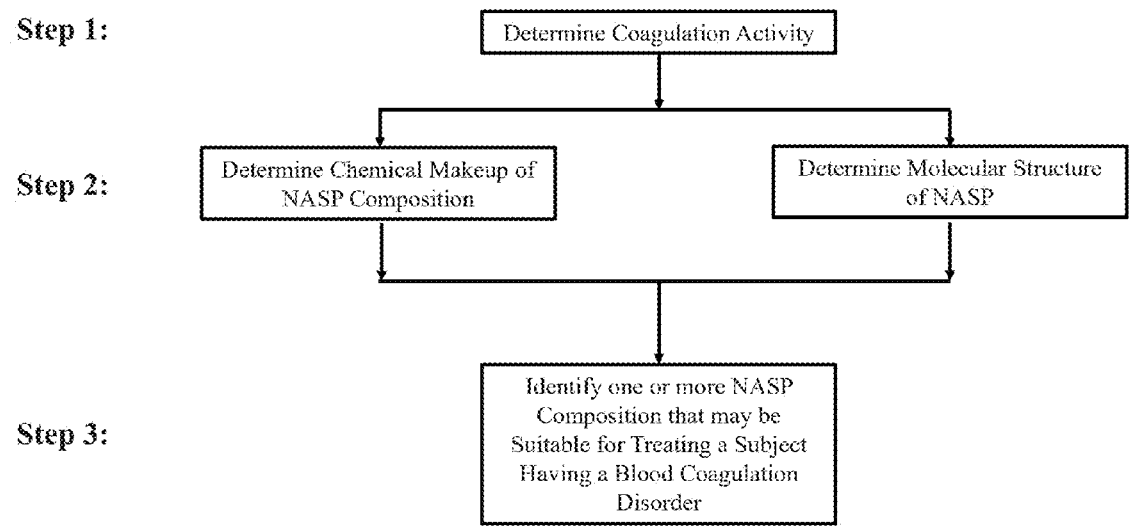
FIGS. 1a-b show flow charts illustrating steps for evaluating one or more NASP compositions according to certain embodiments of the invention.

Aspects of the invention include methods for identifying one or more NASP (non-anticoagulant sulfated polysaccharide) compositions that are suitable for treating a subject having a blood coagulation disorder. In practicing methods according to certain embodiments, NASP compositions are evaluated by determining the coagulation activity and chemical makeup of the NASP composition and the molecular structure of the NASP. Systems for practicing methods of the invention as well as compositions suitable for treating a subject having a blood coagulation disorder are also described.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In further describing the subject invention, methods for evaluating one or more NASP compositions are first described in greater detail. Next, methods for identifying one more NASP compositions that may be suitable for treating a subject having a blood coagulation disorder are reviewed. Systems for practicing methods of the subject invention are also described.

Methods for Identifying One or More NASP Compositions

As summarized above, aspects of the invention include methods for identifying one or more NASP compositions that are suitable for treating a subject having a blood coagulation disorder. In some embodiments, methods include evaluating one or more NASP compositions and determining whether each NASP composition is suitable for treating a subject having a blood coagulation disorder. In other embodiments, methods include screening a plurality of NASP compositions, comparing each NASP composition with each other and identifying whether one or more of the NASP compositions that may be suitable for treating a subject having a blood coagulation disorder.

In describing the subject methods, the term "blood coagulation disorder" is used herein in its conventional sense to refer to any disorder associated with excessive bleeding, such as a congenital coagulation disorder, an acquired coagulation disorder, administration of an anticoagulant, or a trauma induced hemorrhagic condition. Bleeding disorders may include, but are not limited to, hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrand factor, a vitamin K deficiency, a disorder of fibrinogen, including afibrinogenemia, hypofibrinogenemia, and dysfibrinogenemia, an alpha$_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy. Alternatively, a blood coagulation disorder may be the result of administering an anticoagulant to a subject. For example, the subject may have been treated with an anticoagulant including, but not limited to, heparin, a coumarin derivative, such as warfarin or dicumarol, TFPI, AT III, lupus anticoagulant, nematode anticoagulant peptide (NAPc2), active-site blocked factor VIIa (factor VIIai), factor IXa inhibitors, factor Xa inhibitors, including fondaparinux, idraparinux, DX-9065a, and razaxaban (DPC906), inhibitors of factors Va and VIIIa, including activated protein C (APC) and soluble thrombomodulin, thrombin inhibitors, including hirudin, bivalirudin, argatroban, and ximelagatran. In certain embodiments, the anticoagulant in the subject may be an antibody that binds a clotting factor, including but not limited to, an antibody that binds to Factor V, Factor VII, Factor VIII, Factor IX, Factor X, Factor XIII, Factor II, Factor XI, Factor XII, von Willebrand factor, prekallikrein, or high molecular weight kininogen (HMWK).

The term "subject" is meant the person or organism which is diagnosed as having a blood coagulation disorder. As such, subjects of the invention may include but are not limited to mammals, e.g., humans and other primates, such as chimpanzees and other apes and monkey species; and the like, where in certain embodiments the subject are humans.

In describing the present invention, the term "NASP" refers to sulfated polysaccharides (SP) which exhibit non-anticoagulant and anticoagulant activity in any of the various clotting assays described. In embodiments of the invention, NASP compositions may be obtained from any convenient source. For example, NASP compositions may be natural NASP compositions which are found or derived from a naturally occurring source, such as from an animal or plant source and encompass a broad range of subclasses including glycosaminoglycans, heparins, fucoidans, carrageenans, pentosan polysulfates, dermatan sulfates and dextran sulfates. In some embodiments, natural NASP compositions are extracted from a biological source. By "biological source" is meant a naturally-occurring organism or part of an organism. For example, NASP compositions may be extracted from plants, animals, fungi or bacteria. In particular, NASP compositions may be extracted from edible seaweeds, brown algae, echinoderms (e.g., sea urchins, sea cucumbers) and the like. Any convenient protocol can be employed for extracting the NASP composition from the biological source. For instance, the NASP composition can be extracted from the biological source by acid-base extraction, enzymatic degradation, selective precipitation, filtration, among other procedures. Methods for extracting and isolating NASPs from biological sources such as edible seaweeds and brown algae are described in detail in co-pending U.S. patent application Ser. No. 12/449,712, filed Feb. 25, 2010, the disclosure of which is herein incorporated by reference, in its entirety. In certain instances, NASP compositions include fucoidans. As used herein the term, "fucoidan" refers to a diverse group of naturally-occurring complex sulfated polysaccharides which are extracted from certain edible seaweeds, brown algae and echinoderms (e.g., sea urchins, sea cucumbers). In some embodiments, fucoidans are NASPs which are extracted from organisms from the genus *Fucus, Laminaria, Cladosiphon, Namacystus, Undaria, Chordaria, Sargassum, Leathesia, Desmarestia, Dictyosiphon, Dictyota, Padina, Spatoglossum, Adenocystis, Pylayella, Ascophyllum, Bifurcaria, Himanthalia, Hizikia, Pelvetia, Alaria, Arthrothamnus, Chorda, Ecklonia, Eisenia, Macrocystis, Nereocystis, Petalonia, Scytosiphon*, and *Saundersella*, among others. In certain embodiments, fucoidans are *Laminaria japonica* (L.j.) fucoidans; *Fucus vesiculosus* (F.v.) fucoidans, *Undaria pinnatifida* (U.p.) fucoidans, and *Ecklonia maxima* (E.m.) fucoidans.

Depending on the source of the NASP composition, NASP compositions may include one or more NASPs. For example, NASP compositions may include two or more NASPs, such as three or more NASPs and including four or more NASPs. As such, where NASP compositions include more than one NASP, methods may include separating and purifying the NASPs prior to evaluating the one or more NASP compositions. NASPs may be separated using any convenient protocol, such as by acid-base extraction, ion chromatography, affinity chromatography, gel exclusion chromatography, high performance liquid chromatography, size exclusion chromatography and the like.

Figure 1B:
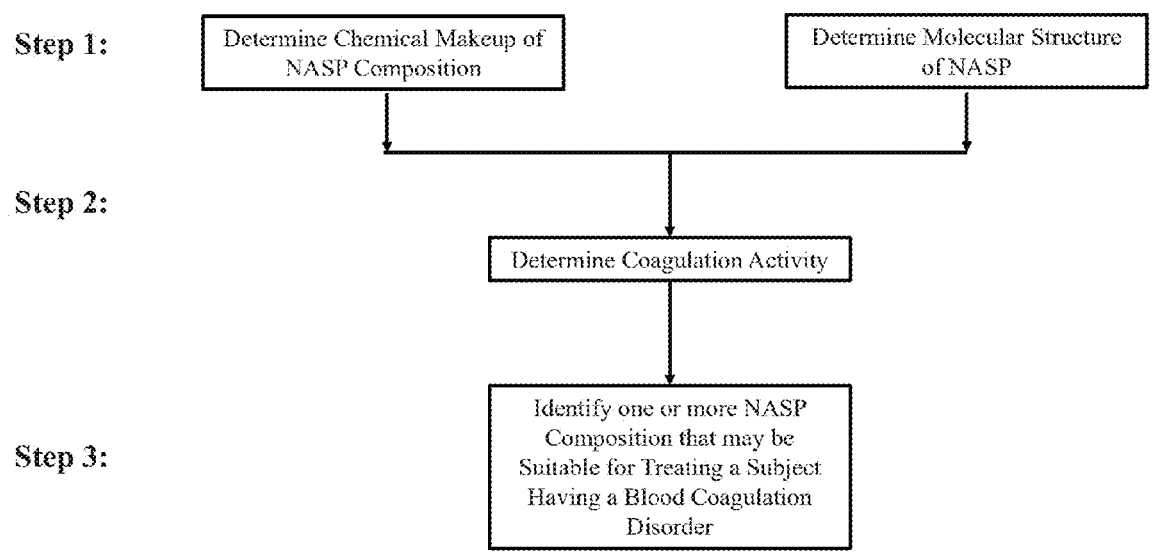

As described above, aspects of the invention include evaluating one or more NASP compositions by determining the coagulation activity and the chemical makeup of the NASP composition and the molecular structure of the NASP. Each step may be conducted at any time during methods of the invention. As such, the coagulation activity, chemical makeup and NASP molecular structure may be determined simultaneously or sequentially. For example, FIG. 1a depicts a flow chart illustrating steps for evaluating one or more NASP compositions according to certain embodiments of the invention. As shown in FIG. 1a, methods may include first, assessing the coagulation activity of the NASP composition, followed by determining the chemical makeup of the NASP composition and the NASP molecular structure. Alternatively, as shown in FIG. 1b, the chemical makeup of the NASP composition and the NASP molecular structure may be determined first, followed by assessing the coagulation activity. In other instances, the coagulation activity, the chemical makeup and the NASP molecular structure are all determined simultaneously. Furthermore, one or more NASP compositions may be evaluated at any given time. As such, in certain instances, more than one NASP composition may be evaluated simultaneously, such as two or more NASP compositions, such as three or more NASP compositions, such as four or more NASP compositions, including five or more NASP compositions may be evaluated simultaneously.

In evaluating a NASP composition according to embodiments of the invention, methods include determining the coagulation activity of the composition. By "coagulation activity" is meant any biological effect that a NASP composition may have on the process of clotting, including anticoagulation and procoagulation. Any sample medium for studying clot formation may be employed to assess coagulation activity and may include but is not limited to whole blood, normal blood plasma, coagulation factor-deficient blood plasma, coagulation factor-inhibited blood plasma, congenitally coagulation factor-deficient blood plasma and synthetically produced plasmas, among others. In some embodiments, coagulation activity is assessed in normal plasma. In other embodiments, coagulation activity is assessed in coagulation factor-inhibited plasmas. By "coagulation factor-inhibited plasmas" is meant one or more coagulation factors (e.g., Factor VIII, Factor IX or Factor XI) are functionally removed from the plasma, such as by an inhibitor, providing coagulation factor-neutralizing activity. In yet other embodiments, coagulation activity is assessed in coagulation factor-deficient plasmas. By "coagulation factor-deficient plasmas" is meant one or more coagulation factors are removed from the plasma, such as by selective affinity immuno-adsoprtion or are plasma samples from patients with congenital coagulation factor deficiencies. For example, coagulation activity may be assessed in plasmas in which Factor VIII (FVIII), Factor IX (FIX) or Factor XI (FXI) have been removed from the plasma (i.e., the plasma is absent of FVIII, FIX or FXI). Alternatively, coagulation activity may be assessed in antibody-mediated FVIII-inhibited, FIX-inhibited or FXI-inhibited plasmas.

According to some embodiments, determining the coagulation activity includes assessing the procoagulant activity of the NASP composition. The term "procoagulant activity" as used herein, refers to the positive effect the NASP composition has in accelerating initiation of coagulation as well as increasing the overall coagulation rate, as compared with a suitable control (determined by blood clotting assays, e.g., CAT, dPT, described in detail below). In other words, procoagulant activity is the effect the NASP composition has on reducing the amount of time for coagulation to begin or in reducing the total amount of time for coagulation to be completed.

Assessing the procoagulant activity of the NASP composition may include, in certain instances, measuring the increase in the overall rate of coagulation by the NASP composition. For example, the overall rate of coagulation may be increased by the NASP composition by 1% or more as compared with a suitable control, such as 5% or more, such as 10% or more, such as 15% or more, such as 20% or more, such as 30% or more, such as 40% or more, such as 50% or more, such as 75% or more, such as 90% or more, such as 95% or more and including 99% or more as compared with a suitable control. In some instances, the overall rate of coagulation that may be increased by the NASP composition ranges from 0.5% to 99% as compared to a suitable control, such as 5% to 90% such as 10% to 75% and including 15% to 50% as compared to a suitable control. Assessing the procoagulant activity of the NASP composition may also include measuring the acceleration in initiating coagulation by the NASP composition. For example, the amount of time required for the coagulation to begin may be reduced by the NASP composition by 5% or more as compared to a suitable control, such as by 10% or more, such as by 25% or more, such as by 50% or more, such as by 75% or more, such as by 90% or more and including by 95% or more as compared to a suitable control. In some instances, the amount of time required for coagulation to begin that may be reduced by the NASP composition ranges from 0.5% to 99% as compared to a suitable control, such as 5% to 90% such as 10% to 75% and including 15% to 50% as compared to a suitable control. The increase in the overall rate of coagulation and the acceleration in initiating coagulation may be measured by any convenient protocol, such as for example, blood clotting assays, calibrated automated thrombography (CAT), activated partial thromboplastin time assay (aPTT) or thromboelastography rotation thromboelastometry (ROTEM) assay, among other clotting protocols.

Assessing the procoagulant activity of the NASP composition may also include evaluating the effect of the composition on thrombin generation. Thrombin is produced in the blood coagulation cascade by the enzymatic cleavage of two sites on prothrombin by activated Factor X (Xa). Thrombin acts to convert factor XI to XIa, VIII to VIIIa, V to Va, and fibrinogen to fibrin. Since the production of thrombin is dependent upon the activity of tissue factors in the blood coagulation cascade, thrombin generation in coagulation factor-inhibited or coagulation factor-deficient plasma is significantly reduced as compared to normal levels. When a NASP composition is added to coagulation factor-inhibited or coagulation factor-deficient plasmas, thrombin generation is increased as a function of the concentration of the NASP.

As such, methods according to certain embodiments, include measuring the amount of thrombin generation that is restored by the NASP composition in coagulation factor-inhibited or coagulation factor-deficient plasmas. For example, NASP compositions may restore the amount of thrombin generation to 5% or more of normal levels, such as 10% or more, such as 25% or more, such as 50% or more, such as 75% or more, such as 90% or more, such as 95% or more, including restoring the amount of thrombin generation in coagulation factor-inhibited plasma or coagulation factor-deficient plasma to 100% of normal levels. In some instances, the amount of thrombin generation that is restored by the NASP composition in coagulation factor-inhibited or coagulation factor-deficient plasmas ranges from 0.5% to 100%, such as 5% to 90% such as 10% to 75% and including 15% to 50%. In other instances, NASP compositions may increase thrombin generation in coagulation factor-inhibited or coagulation factor-deficient plasmas beyond normal levels, such as for example, by 5% or more, such as 10% more, such as 25% or more, such as 50% or more, such as 75% or more, including 100% or more, such as 1.5 times normal levels, such as 2 times normal levels, such as 3 times normal levels, including 5 times normal levels. In certain instances, evaluating the effect of the composition on thrombin generation includes measuring the concentration of the NASP required to restore coagulation in FVIII-inhibited plasma to normal levels. For example, the concentration of the NASP required to restore coagulation to normal levels in FVIII-inhibited plasma may range from 0.1 to 10 μg/mL, such as from 0.5 to 5 μg/mL, such as from 0.75 to 2.5 μg/mL and including from 0.8 to 2 μg/mL.

Methods may also include evaluating the effect of the NASP composition on thrombin generation by measuring the concentration of the NASP at peak thrombin generation. For example, the concentration of the NASP at peak thrombin generation may be 10 μg/mL or less, such as 8 μg/mL or less, such as 7.5 μg/mL or less, such as 5 μg/mL or less, such as 2.5 μg/mL or less, such as 1 μg/mL and including 0.8 μg/mL or less. Likewise, the half maximal effective concentration ($EC_{50}$) of the NASP may also be measured in order to evaluate the effect of the NASP composition on thrombin generation. The term "half maximal effective concentration" is used herein in its conventional sense to refer to the concentration of the NASP which induces thrombin generation halfway between baseline and its maximum value. As such, the $EC_{50}$ value for procoagulant activity reflects the relative potency of the NASP composition on thrombin generation, where the $EC_{50}$ represents the optimal concentration of NASP in thrombin generation experiments. For example, the $EC_{50}$ value for procoagulant activity of the NASP composition may be 5.0 μg/mL or less, such as 4.5 μg/mL or less, such as 4.0 μg/mL or less, such as 3.5 μg/mL or less, such as 3.0 μg/mL or less, such as 2.0 μg/mL or less, such as 1.5 μg/mL or less, such as 1.25 μg/mL or less, such as 1.0 μg/mL or less, such as 0.8 μg/mL or less, such as 0.6 μg/mL or less, such as 0.4 μg/mL or less, such as 0.3 μg/mL or less, such as 0.2 μg/mL or less and including 0.1 μg/mL or less. In some instances, the $EC_{50}$ value for procoagulant activity of the NASP composition ranges from 5.0 to 0.001 μg/mL, such as 4.0 to 0.005 μg/mL, such as 3.0 to 0.01 μg/mL and including 2.5 to 0.05 μg/mL.

Assessing the procoagulant activity of the composition may also include determining the procoagulant window of the composition. By "procoagulant window" is meant the range in the concentrations of the NASP which exhibit procoagulant activity (i.e, an increase in the overall rate or acceleration in the initiation of coagulation). In other words, the procoagulant window is the range of NASP concentrations which may exhibit a positive therapeutic response in treating a blood coagulation disorder. The procoagulant window is the range that is between a noneffective amount and an amount which results in anticoagulant activity. In other words, below the lowest concentration of the procoagulant window, the NASP has no effect on clotting and above the highest concentration of the procoagulant window, anticoagulant activity is observed. For example, a NASP concentration which falls within the procoagulant window may increase the rate of clotting by 5% or more, such as 10% or more, such as 25% or more, such as 50% or more, such as 75% or more, such as 90% or more, including by 99% or more and in certain instances, increasing the rate of blood clot formation by 1.5-fold or more, such as 2-fold or more, such as 5-fold or more, such as 10-fold or more, such as 50-fold or more, including increasing the rate of blood clot formation by 100-fold or more. In some instances, the NASP concentration which falls within the procoagulant window may increase the rate of clotting in a range of 1% to 99%, such as 5% to 90% and including 10% to 75% and in certain instances, increasing the rate of blood clot formation in a range of 1.5-fold to 1000-fold such as 5-fold to 500-fold, such as 10-fold to 250-fold and including 20-fold to 100-fold. The determined procoagulant window of a NASP composition may vary, ranging from 0.1 to 500 μg/mL, such as 0.1 to 400 μg/mL, such as 0.1 to 300 μg/mL, such as 0.1 to 200 μg/mL and including 0.1 to 100 μg/mL.

Methods may also include assessing the procoagulant activity of the NASP composition by measuring tissue factor pathway inhibitor (TFPI)-neutralizing activity. TFPI is a single-chain polypeptide which can reversibly inhibit FXa and thrombin (factor IIa) during the coagulation cascade. While FXa is inhibited, the Xa-TFPI complex can inhibit FVIIa-tissue factor complex, which results in a reduction in clotting below normal levels. As such, by "TFPI-neutralizing activity" is meant that inhibition by TFPI is reduced by the NASP composition. In certain instances, methods include determining whether the NASP composition exhibits TFPI-neutralizing activity. Where the NASP composition exhibits TFPI-neutralizing activity, methods may also include measuring the reduction in TFPI activity as a result of the NASP composition. For example, the NASP composition may reduce TFPI activation by 1% or more, such as 5% or more, such as 10% or more, such as 15% or more, such as 20% or more, such as 30% or more, such as 40% or more, such as 50% or more, such as 75% or more, such as 90% or more, such as 95% or more, including reducing inhibition by TFPI by 99% or more, as determined by blood clotting assays. In some instances, the reduction of TFPI activation by the NASP composition may range from 1% to 99%, such as 5% to 90%, such as 10% to 75% and including 15% to 50%. The TFPI-neutralizing activity of the NASP composition may be measured using any convenient protocol, such by dilute prothrombin time assay or calibrated automated thrombography. The TFPI-neutralizing activity may be tested in normal plasma with added full length TFPI or in TFPI-depleted plasmas with added full-length TFPI or with C-terminal truncated TFPI. The determined half maximal effective concentration for TFPI-neutralizing activity of the NASP may be in some embodiments, 5.0 μg/mL or less, such as 3.0 μg/mL or less, such as 2.0 μg/mL or less, such as 1.5 μg/mL or less, such as 1.0 μg/mL or less, such as 0.9 μg/mL or less, such as 0.8 μg/mL or less, such as 0.7 μg/mL or less, such as 0.6 μg/mL or less, such as 0.5 μg/mL or less and including 0.4 μg/mL or less. In some instances, the half maximal effective concentration for TFPI-neutralizing activity of the NASP ranges from 0.01 μg/mL to 10 μg/mL, such as 0.05 μg/mL to 7 μg/mL, such as 0.1 μg/mL to 5 μg/mL and including 0.5 μg/mL to 2.5 μg/mL.

In certain instances, measuring tissue factor pathway inhibitor (TFPI)-neutralizing activity further includes confirming the mechanism of TFPI-neutralizing activity by the NASP using surface plasmon resonance binding experiments. For example, confirming mechanism of TFPI-neutralizing activity may include determining that the NASP binds to full-length TFPI. In other instances, confirming the mechanism of TFPI-neutralizing activity may include determining that the NASP binds to the C-terminal region of TFPI.

Assessing the procoagulant activity of the NASP composition may also include determining whether the composition activates the contact pathway (i.e., intrinsic coagulation pathway). The contact pathway begins with formation of the primary complex on collagen by high-molecular-weight kininogen (HMWK), prekallikrein, and FXII (Hageman factor). Prekallikrein is converted to kallikrein and FXII becomes FXIIa. FXIIa converts FXI into FXIa. Factor XIa activates FIX, which with its co-factor FVIIIa form the tenase complex, which activates FX to FXa. Since the contact pathway is associated with inflammation, NASP compositions which activate the contact pathway would be less suitable in treating a subject having a blood coagulation disorder. Determining whether the NASP composition activates the contact pathway may be tested using any convenient protocol. For example, NASP compositions may be tested for activation of the contact pathway using normal plasma in the presence and absence of corn trypsin inhibitor (CTI). CTI inhibits FXIIa and thus, blocks the contact pathway. As such, if the NASP composition exhibits higher thrombin formation in the absence of CTI than in the presence of CTI, the NASP composition activates the contact pathway. Where the NASP composition activates the contact pathway, methods may also include measuring the concentration of the NASP at which the contact pathway is activated. For example, the concentration of the NASP which activates the contact pathway may be determined to be 5 μg/mL or greater, such as 6 μg/mL or greater, such as 7 µg/mL or greater, such as 8 µg/mL or greater, such as 10 µg/mL or greater, such as 15 µg/mL or greater, such as 20 µg/mL or greater, such as 25 µg/mL or greater and including 35 µg/mL or greater. In some instances, the concentration of the NASP which activates the contact pathway may range from 3 µg/mL to 100 µg/mL, such as 5 µg/mL to 90 µg/mL, such as 7.5 µg/mL to 75 µg/mL and including 10 µg/mL to 50 µg/mL. In other embodiments, methods include comparing the concentration of the NASP which activates the contact pathway with the half maximal effective concentration ($EC_{50}$) for procoagulation by the NASP. For example, the concentration of the NASP which activates the contact pathway may be 10-fold or greater than the $EC_{50}$ value for procoagulant activity of the NASP, such as 15-fold or greater, such as 20-fold or greater, such as 25-fold or greater and including 30-fold or greater than the $EC_{50}$ of the NASP. In some instances, the concentration of the NASP which activates the contact pathway ranges from 5-fold to 50-fold than the $EC_{50}$ value for procoagulant activity of the NASP, such as 5-fold to 40-fold, such as 7-fold to 35-fold and including 10-fold to 25-fold than the $EC_{50}$ value for procoagulant activity of the NASP.

As described above, methods include determining the coagulation activity of the composition. In some embodiments, determining the coagulation activity also includes assessing the anticoagulant activity of the NASP composition. The term "anticoagulant activity" as used herein, refers to the effect the NASP composition has in delaying the initiation of coagulation as well as decreasing the overall coagulation rate, as compared with a suitable control (determined by blood clotting assays, e.g., aPTT, CAT). In other words, anticoagulant activity is the effect the NASP composition has in increasing the amount time for coagulation to begin or in increasing the total amount of time for coagulation to be completed.

Assessing the anticoagulant activity of the NASP composition may include, in certain instances, measuring the decrease in the overall rate of coagulation by the NASP composition. For example, the overall rate of coagulation may be decreased by the NASP composition by 1% or more as compared with a suitable control, such as 5% or more, such as 10% or more, such as 15% or more, such as 20% or more, such as 30% or more, such as 40% or more, such as 50% or more, such as 75% or more, such as 90% or more, such as 95% or more and including 99% or more as compared with a suitable control. In some instances, the overall rate of coagulation that may be decreased by the NASP composition ranges from 1% to 99% as compared with a suitable control, such as 5% to 90%, such as 7.5% to 75% and including 10% to 50% as compared with a suitable control. Assessing the anticoagulant activity of the NASP composition may also include measuring the delay in initiating coagulation by the NASP composition. For example, the amount of time required for the coagulation to begin may be increased by the NASP composition by 5% or more as compared to a suitable control, such as by 10% or more, such as by 25% or more, such as by 50% or more, such as by 75% or more, such as by 90% or more and including by 95% or more as compared to a suitable control. In some instances, the amount of time required for the coagulation to begin may be increased by the NASP ranges from 1% to 99%, such as 5% to 90%, such as 7.5% to 75% and including 10% to 50% as compared to a suitable control. The decrease in overall rate of coagulation and the delay in initiating coagulation by the NASP composition may be determined using any convenient protocol, such as for example by activated partial thromboplastin time assay.

In certain embodiments, assessing the anticoagulant activity includes measuring clotting time as a function of NASP concentration. In particular, measuring clotting time as a function of NASP concentration may include determining the concentration of the NASP at which a 50% increase in clotting time occurs as compared to normal plasma. In other words, methods include measuring the amount of the NASP required to reduce the overall rate of coagulation by 50% as compared to normal levels. For example, the NASP concentration at which a 50% increase in clotting time occurs may be 2 µg/mL or greater, such as 3 µg/mL or greater, such as 4 µg/mL or greater, such as 5 µg/mL or greater, such as 6 µg/mL or greater, such as 7 µg/mL or greater, such as 8 µg/mL or greater and including 10 µg/mL or greater. In some instances, the NASP concentration at which a 50% increase in clotting time occurs ranges from 0.01 µg/mL to 25 µg/mL, such as 0.05 µg/mL to 20 µg/mL, such as 0.1 µg/mL to 15 µg/mL and including 1 µg/mL to 10 µg/mL.

In assessing the coagulation activity of the NASP composition, methods may also include comparing the procoagulant activity with the anticoagulant activity. For instance, methods may include calculating the ratio of the NASP concentration at which a 50% increase in clotting time occurs to the half maximal effective concentration for procoagulation. In these instances, the ratio value may be 1.1 or greater, such as 5 or greater, such as 10 or greater, such as 15 or greater, such as 25 or greater, such as 35 or greater and including 50 or greater. In some instances, the ratio ranges from 1.1 to 100, such as 1.5 to 90, such as 2 to 75 and including a ratio which ranges from 5 to 50. A high ratio value (e.g., 20 or greater) indicates that the NASP composition has significant procoagulant activity and little anticoagulant activity. A low ratio value (e.g., 10 or lower) indicates that the NASP composition has a weak procoagulant activity and significant anticoagulant activity.

In evaluating a NASP composition according to embodiments of the invention, methods also include assessing the molecular structure of the NASP. In some embodiments, determining the molecular structure of the NASP includes determining the average molecular weight of the NASP. For example, the average molecular weight of the NASP may be from 10 to 1000 kDa daltons, such as from 50 to 800 kDa, such as from 100 to 500 kDa daltons, including 100 to 200 kDa. In certain instances, the average molecular weight of the NASP is 15 kDa or greater, such as 20 kDa or greater, such as 25 kDa or greater and including 35 kDa or greater. In other instances, the average molecular weight of the NASP is 41 kDa or less, such as 40 kDa or less, such as 30 kDa or less, such as 20 kDa or less and including 15 kDa.

Since the NASP compositions that are evaluated may contain NASPs having a broad range of sizes and molecular weights, methods of the invention may also include determining the polydispersity of the NASP composition. For example, the polydispersity of the NASP composition may be 1.1 or greater, such as 1.25 or greater, such as 1.3 or greater, such as 1.5 or greater, such as 1.8 or greater and including 2.0 and greater. In some instances, the polydispersity of the NASP composition ranges from 1.1 to 2, such as 1.2, such as 1.3 and including 1.5. The molecular weight and polydispersity can be determined using any convenient protocol, such as for example, gel permeation chromatography or high-performance size-exclusion chromatography (HPSEC), capillary electrophoresis, PAGE (polyacrylamide gel electrophoresis), agarose gel electrophoresis, among others. In certain embodiments, the molecular weight of the NASP is determined using Size Exclusion Chromatography-MultiAngle Light Scattering (SEC-MALLS).

In certain embodiments, assessing the molecular structure of the NASP composition includes determining the saccharide content of the NASP. For example, the saccharide content may include fucose residues, xylose residues, galactose residues, glucose residues, mannose residues, rhamnose residues, arabinose residues and uronic acid. Since saccharide content of NASPs vary, methods according to certain embodiments, also include determining the heterogeneity of the saccharide content. In determining the heterogeneity of the saccharide content, the amount of each saccharide residue is first determined and then the percentage that each saccharide contributes to the total saccharide content is then calculated. For example, the fucose content may be determined to be 40% or greater, such as 50% or greater, such as 75% or greater, such as 80% or greater, such as 85% or greater and including 90% or greater. In some instances, the fucose content may be determined to be a percentage which ranges from 40% to 99%, such as 50% to 95%, and including 60% to 90%. In other instances, the galactose content may be determined to be 10% or greater, such as 15% or greater, such as 25% or greater, such as 30% or greater and including determining that the galactose content is 35% or greater. In some instances, the galactose content may be determined to be a percentage which ranges from 1% to 30%, such as 2% to 25%, such as 3% to 20% and including 5% to 15%. In yet other instances, the glucose content may be determined to be 10% or less, such as 5% or less, such as 4% or less, such as 3% or less, such as 2% or less and including determining that the glucose content is 1% or less. In some instances, the glucose content may be determined to be a percentage which ranges from 0.1% to 10%, such as 0.5% to 8% and including 1% to 5%. In yet other instances, the alginate content may be determined to be 10% or less, such as 5% or less, such as 4% or less, such as 3% or less, such as 2% or less and including determining that the alginate content is 1% or less. In some instances, the alginate content may be determined to be a percentage which ranges from 0.1% to 10%, such as 0.5% to 8% and including 1% to 5%. The saccharide content and heterogeneity may be determined using any convenient protocol, such as for example, by hydrolyzing the NASP into its corresponding monosaccharides and analyzing the monosaccharides composition by mass spectrometry, inductively coupled plasma, ion chromatography, gas chromatography, atomic absorption, graphite furnace atomic absorption spectrometry, inductively coupled plasma mass spectrometry, inductively coupled plasma atomic emission spectrometry, flame atomic absorption spectrometry, or some other convenient protocol.

Assessing the molecular structure of the NASP may also include determining the fucose and alginate content by $^{13}$C-NMR (Nuclear Magnetic Resonance) spectroscopy. NMR spectroscopy can be a powerful technique for elucidating the structure and quantitative characteristics of complex carbohydrates. Thus, in certain embodiments, quantitative $^{13}$C-NMR may be employed to characterize the fucose and alignate content of the NASP. To determine quantitative conditions for the fucose and alginate content by $^{13}$C-NMR, relative peak areas may be evaluated using various relaxation delays. In particular, saccharide anomeric peaks at δ 88-112 ppm, carbons of the sugar ring at δ 55-88 ppm, the carbonyl peak of alginate at δ 170-185 ppm and the methyl peak of fucose at δ 9-20 ppm may be integrated. Since alginate contains a carbonyl moiety and every saccharide contains one anomeric carbon per residue, the alginate content (% mol alginate/mol NASP) may be calculated by the equation:

$$C\%^{alginate} = (\int carbonyls / \int anomerics) \times 100\%, \quad (1)$$

where $\int carbonyls$ is the integral of carbonyl groups and $\int anomerics$ is the integral of the anomeric carbons.

Likewise, fucose content (% mol fucose/mol NASP) is calculated using the methyl group of fucose by the equation:

$$C\%^{fucose} = (\int methyls / (\int anomerics - \int carbonyls)) \times 100\%, \quad (2)$$

wherein $\int methyls$ is the integral of methyl groups on fucose. Where the NASP sample has been determined to contain only a small amount of alginate (e.g., less than 10%), the fucose content may be calculated using the equation:

$$C\%^{fucose} = (\int methyls / (\int anomerics)) \times 100\%. \quad (3)$$

As desired, the fucose content determined by quantitative $^{13}$C-NMR may subsequently be compared with the fucose content as determined by hydrolysis of the NASP as described above. Since the hydrolysis method determines the individual monosaccharide content and $^{13}$C-NMR determines the saccharide content in an intact NASP, the values determined by the respective methods may differ slightly. However, the difference in saccharide content determined by the hydrolysis method and by $^{13}$C-NMR will not differ by more than 10%, such as 8% or less, such as 7% or less, such as 6% or less, such as 5% or less, such as by 4% or less, such as 3% or less, such as by 2% or less, such as 1% or less and including by 0.1% or less. For example, the difference in saccharide content determined by the hydrolysis method from the saccharide content determined by $^{13}$C-NMR may range from 0.001% to 10%, such as 0.005% to 9%, such as 0.01% to 8% and including 0.1% to 5%.

In addition to determining the fucose and alginate content, $^{13}$C-NMR may be employed to qualitatively determine the heterogeneity of the saccharide content. The heterogeneity of the saccharide content may be determined by observing the degree of complexity of the anomeric and sugar carbon regions of the $^{13}$C-NMR spectra. Based on the complexity of the anomeric and sugar carbon regions in the $^{13}$C-NMR spectra, a qualitative assessment of the heterogeneity of the saccharide content can be made about the NASP composition. For example, if a highly complex $^{13}$C-NMR spectra is observed in the anomeric and sugar carbon regions, the NASP composition may be determined to have high heterogeneity. In contrast, if the $^{13}$C-NMR spectrum has little complexity in the anomeric and carbon regions, the NASP composition may be determined to have low heterogeneity. Subsequently, the heterogeneity observed by $^{13}$C-NMR spectrum may be confirmed quantitatively as desired, such as by hydrolysis of the NASP composition and analyzed using ion chromatography, mass spectrometry, inductively coupled plasma, gas chromatography, atomic absorption, graphite furnace atomic absorption spectrometry, inductively coupled plasma mass spectrometry, inductively coupled plasma atomic emission spectrometry, flame atomic absorption spectrometry or some other convenient protocol, as described above.

In some embodiments, assessing the molecular structure of a NASP includes determining the degree of polymerization of the NASP. The term "degree of polymerization" is used in its conventional sense to refer to the length of the polysaccharide backbone of the NASP. In other words the degree of polymerization is the number of monosaccharide units positioned along the polysaccharide backbone of the NASP. For example, methods may include determining that the NASP has a degree of polymerization which ranges from 25 to 5000, such as 50 to 2500, such as 75 to 1500, such as 100 to 1000 and including of 125 to 500. In certain embodiments, the NASP may be determined to have a degree of polymerization which ranges from 70 to 200. In some instances, methods include determining that the NASP has a degree of polymerization which is 20 or greater, such as 30 or greater, such as 50 or greater, such as 100 or greater, such as 125 or greater and including 150 or greater. In certain instances, methods include determining that the NASP has a degree of polymerization which is 70 or greater. The degree of polymerization may be determined using any convenient protocol, such as for example, by size exclusion chromatography or size fractionation using ultra-filtration with a plurality of cut-off filter membranes. Alternatively, the degree of polymerization may be determined by hydrolyzing the NASP into its corresponding monosaccharides and analyzing the monosaccharides composition by mass spectrometry, inductively coupled plasma, ion chromatography, gas chromatography, atomic absorption, graphite furnace atomic absorption spectrometry, inductively coupled plasma mass spectrometry, inductively coupled plasma atomic emission spectrometry, flame atomic absorption spectrometry or some other convenient protocol.

In certain embodiments, assessing the molecular structure of the NASP includes determining the glycosidic bond configuration of the NASP. For example, determining the glycosidic bond configuration may include determining whether the NASP is a linear polysaccharide, a branched polysaccharide, or both linear and branched. By "linear polysaccharide" is meant a polysaccharide or part of a polysaccharide that contains only α-1,4 glycosidic bonds, α-1,2 glycosidic bonds or α-1,3 glycosidic bonds, or alternating α-1,2/α-1,3/α-1,4 glycosidic bonds. By "branched polysaccharide" is meant a polysaccharide or part of a polysaccharide that contains two or more glycosidic bonds to other saccharide residues, where one of the glycosidic bonds is an α-1,4-glycosidic bond, α-1,2 glycosidic bonds or α-1,3 glycosidic bonds, or alternating α-1,2/α-1,3/α-1,4 glycosidic bonds, and the other is an α-1,6-glycosidic bond. Where the NASP is both linear and branched, methods may further include determining the relative percentage of linear portions of the polysaccharide to branched portions of the polysaccharide. For example, the NASP may be 10% linear or more, such as 25% linear or more, such as 50% linear or more, such as 75% linear or more and including 90% linear or more. Likewise, the NASP may be 10% branched or more, such as 25% branched or more, such as 50% branched or more, such as 75% branched or more and including 90% branched or more. In some instances, the percentage of the NASP which is linear or branch ranges from 1% to 90%, such as 5% to 75% and including 10% to 50%. The ratio of linear saccharide residues to branching saccharide residues in NASPs of interest may be 3 or less, such as 2.5 or less, such as 2 or less, such as 1.5 or less, such as 1.4 or less, such as 1.3 or less, such as 1.2 or less and including 1 or less. In some instances, the ratio of linear saccharide residues to branching residues ranges from 0.5 to 3, such as 1 to 2.5, such as a ratio of 1.4. In other words, in NASPs of interest one in every 3 saccharide residues or less has a branching saccharide residue attached to it, such as one in every 2.5 saccharide residues or less, such as one in every 2 saccharide residues, such as one in every 1.5 saccharide residues and including one in every 1.4 saccharide residues has a branching saccharide residue attached to it. Any convenient protocol can be employed to determine the glycosidic bond configuration of the NASP and may include but is not limited to NMR spectroscopy, 2-D NMR spectroscopy (e.g., proton correlation spectroscopy (COSY), proton-carbon phase sensitive multiplicity edited heteronuclear single quantum correlation (HSQC) and proton-carbon heteronuclear multiple bond correlation (HMBC)), 3-D NMR spectroscopy (e.g., HSQC-TOCSY), tandem mass spectrometry, electrospray ionization trap mass spectrometry, capillary electrophoresis, IR spectroscopy, or any combination thereof.

In assessing the molecular structure of a NASP, methods may also include determining the anionic charge density of the NASP. The term "anionic charge density" is used in its conventional sense to refer to the measure of formal negative charge per saccharide residue of the NASP. In other words, the anionic charge density is the average negative charge per saccharide residue in the NASP. For example, the anionic charge density of the NASP may be 0.1 or greater, such as 0.2 or greater, such as 0.3 or greater, such as 0.5 or greater, such as 0.6 or greater and including 0.75 or greater. In these embodiments, 10% or greater of the saccharide residues of the NASP may anionic, such as 20% or greater, such as 30% or greater, such as 50% or greater, such as 60% or greater and including 75% or greater of the saccharide residues of the NASP may be anionic. In certain embodiments, methods include determining that the anionic charge density of the NASP ranges from 0.1 to 0.6, such as 0.2 to 0.6, such as 0.3 to 0.6, including 0.5 to 0.6, such as 0.55. In some embodiments, the anionic charge density is equivalent to the degree of sulfation, as described in greater detail below.

In assessing the molecular structure of the NASP, methods may also include determining the sulfur content of the NASP. In some embodiments, determining the sulfur content includes determining the weight percent of sulfur in the NASP. For instance, the NASP may be determined to have 5% or more sulfur by weight, such as 10% or more sulfur by weight, such as 15% or more sulfur by weight, such as 20% or more sulfur by weight, including 25% or more sulfur by weight. In some instances, the NASP may be determined to have a sulfur content by weight which ranges from 1% sulfur by weight to 25% sulfur by weight, such as 3% to 20% and including as 5% to 15%. Any convenient protocol can be employed to determine the weight percent of sulfur, such as for example ion chromatography, gas chromatography, mass spectrometry, inductively coupled plasma, atomic absorption, inductively coupled plasma mass spectrometry, inductively coupled plasma atomic emission spectrometry, flame atomic absorption spectrometry, graphite furnace atomic absorption spectrometry, or any combination thereof.

In certain embodiments, determining the sulfur content may include determining the amount of sulfur in the NASP that is present as sulfate. The term "sulfate" is used in its conventional sense refers to the oxyanion of sulfur, $SO_4^{2-}$, however, any oxyanion of sulfur having a central sulfur atom bonded to at least one oxygen atom may be employed, such as sulfite, persulfate, hyposulfate or thiosulfate. For instance, the NASP may be determined to have 10% or more sulfate by weight, such as 15% or more sulfate by weight, such as 20% or more sulfate by weight, including 25% or more sulfate by weight. In some instances, the NASP may be determined to have a sulfate content by weight which ranges from 1% sulfate by weight to 25% sulfate by weight, such as 3% to 20% and including as 5% to 15%. Any convenient protocol can be employed to determine the amount by weight of sulfate in the NASPs, such as those described above for determining sulfur content. For example, methods for determining the amount of sulfation may include but is not limited to mass spectrometry, inductively coupled plasma, ion chromatography, gas chromatography, atomic absorption, graphite furnace atomic absorption spectrometry, inductively coupled plasma mass spectrometry, inductively coupled plasma atomic emission spectrometry, flame atomic absorption spectrometry, acidimetric titration, or any combination thereof.

Furthermore, in determining the amount of sulfate present in the NASP, the degree of sulfation may also be determined. The term "degree of sulfation" is used in its conventional sense to refer to the average number of sulfate groups per saccharide residue of the NASP. For example, the degree of sulfation of the NASP may be 0.1 or greater, such as 0.2 or greater, such as 0.3 or greater, such as 0.5 or greater, such as 0.6 or greater, such as 0.7 or greater, such as 0.9 or greater, such as 1.0 or greater, such as 1.25 or greater and including 1.5 or greater. In certain embodiments, methods include determining that the degree of sulfation of the NASP ranges from 0.1 to 0.6, such as 0.15 to 0.6, such as 0.2 to 0.6, such as 0.3 to 0.6 and including 0.5 to 0.6, such as 0.55.

In some embodiments, assessing the molecular structure of the NASP includes determining the sulfation configuration of the NASP. In other words, methods may include determining the sulfate pattern of sulfated saccharide residues of a NASP. For example, the saccharide residue may be determined to be sulfated at the 4-O-position. In other instances, the saccharide residue is determined to be sulfated at the 3-O-position. In yet other instances, the saccharide residue is determined to be sulfated at the 2-O-position. In certain instances, the monosaccharide residue may be determined to be sulfated at both the 4-position and at the 3-position. In other instances, each saccharide residue may determined to be sulfated at the 4-O-position and the 2-O-position. In other instances, each saccharide residue may be determined to be sulfated at the 3-O-position and the 2-O-position. In yet other instances, each saccharide residue may be determined to be sulfated at the 4-O-position, 3-O-position and 2-O-position. Each saccharide residue of the NASP polysaccharide backbone may have the same or different sulfation configurations. For example, 50% or more of the sulfated saccharide residues of a NASP may be determined to be sulfated at 4-O-position, such as 60% or more, such as 75% or more, such as 90% or more, such as 95% or more and including all of the sulfated monosaccharide residues of a NASP may be determined to be sulfated at the 4-O-position. In some instances, the percentage of sulfated saccharide residues of the NASP may be determined to be sulfated at the 4-O-position in a range of 50% to 99%, such as 55% to 90%, such as 60% to 85% and including 65% to 75%.

The number of sulfate groups bonded to each saccharide residue on the NASP polysaccharide backbone may also be determined. For example, each saccharide residue (e.g., fucose, galactose, rhamnose, arabinose, glucose, mannose, xylose as described above) may be determined to contain one (i.e., monosulfated) or more (i.e., polysulfated) sulfate moieties. In some instances, each saccharide residue of the NASP may have the same number of sulfate groups. For example, in determining the number of sulfate groups bonded to each monosaccharide residue, 10% or more of the saccharide residues of NASPs of the invention may be determined to be monosulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues. In some instances, the percentage of saccharide residues that are monosulfated ranges from 5% to 99%, such as 10% to 90% and including 15% and 75%. In other embodiments, 10% or more of the saccharide residues of NASPs of the invention are determined to be polysulfated, such as 15% or more of the saccharide residues, such as 25% or more of the saccharide residues, such as 50% or more of the saccharide residues, such as 75% or more of the saccharide residues, such as 90% or more of the saccharide residues, such as 95% or more of the saccharide residues, including 99% or more of the saccharide residues. In some instances, the percentage of saccharide residues that are polysulfated ranges from 5% to 99%, such as 10% to 90% and including 15% and 75%. Where both monosulfated and polysulfated saccharide residues are present, the ratio of monosulfated residues to polysulfated residues in NASPs may be calculated. For example, the calculated ratio of monosulfated to polysulfated saccharide residues may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. Likewise the calculated ratio of polysulfated saccharide to monosaccharide residues may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. Any convenient protocol can be employed to determine the sulfation of the NASPs, such as described above. For example, methods for determining the degree of sulfation, the sulfation configuration and the number of sulfate groups on sulfated saccharide residues of NASPs of interest may include but is not limited to mass spectrometry, electrospray ionization trap mass spectrometry, capillary electrophoresis, ion chromatography, elemental analysis, acidimetric titration, desulfation, stability of sulfate esters to alkali and methylation analysis, NMR spectroscopy, IR spectroscopy, or any combination thereof.

Where the anionic charge density and the degree of sulfation are both determined, methods may also include comparing the ratio of anionic charge density with the degree of sulfation. For example, the calculated ratio of anionic charge density to degree of sulfation may range between 1:1 and 1:1.25; 1:1.25 and 1:1.5; 1:5 and 1:1.75; 1:75 and 1:2 or a range thereof. Likewise the calculated ratio of degree of sulfation to anionic charge may range between 1:1 and 1:1.25; 1:1.25 and 1:1.5; 1:5 and 1:1.75; 1:75 and 1:2 or a range thereof. By comparing the anionic charge density with the degree of sulfation, the percentage of the anionic charge density of the NASP which is related to saccharide residue sulfation may be determined. For example, methods may include determining that 50% or greater of the anionic charge density of the NASP is related to monosaccharide sulfation, such as 60% or greater, such as 70% or greater, such as 80% or greater, such as 90% or greater, such as 95% or greater and including determining that 99% or greater of the anionic charge density of the NASP is related to monosaccharide sulfation. In certain instances, assessing the molecular structure of the NASP includes determining that all of the anionic charge density of the NASP is related to monosaccharide sulfation.

In evaluating a NASP molecular structure to determine whether the NASP may be suitable for administering to a subject having a blood coagulation disorder, methods may further include oversulfating or desulfating the NASP. The term "oversulfating" is used in its conventional sense to refer to chemically or enzymatically increasing the sulfate content of the NASP. Conversely, the term "desulfating" refers to chemically or enzymatically decreasing the sulfate content of the NASP. Any convenient protocol can be used to chemically sulfate a NASP, so long as the sulfate content of the resulting NASP increases as a result of new sulfate moieties covalently bonded to the NASP structure or to chemically desulfate a NASP so long as the sulfate content of the resulting NASP decreases a result of sulfate moieties being removed from the NASP structure. For example, one or more free hydroxyl groups along the polysaccharide backbone may be sulfated by bonding one or more sulfate anions to the free hydroxyl groups along the polysaccharide backbone. In other instances, sulfur trioxide complexes with pyridine, triethylamine, or with stannous complexes may be employed (see for example, the methods as described in the Experimental section below as well as methods for sulfating hydroxyl groups in Calvo-Asin, J. A., et al., *J. Chem. Soc, Perkin Trans 1*, 1997, 1079).

By oversulfating or desulfating the NASP, the impact of sulfation on procoagulant and anticoagulant activity may be further confirmed. For example, in some embodiments, the impact of degree of sulfation on procoagulant or anticoagulant activity may be evaluated by oversulfating a NASP having a predetermined degree of sulfation. Where a NASP is oversulfated, the extent of oversulfation may vary as desired. For example, the NASP may be oversulfated to increase the number of sulfated saccharide residues in the NASP by 10% or more, such as 25% or more, such as 50% or more, such as 75% or more and including oversulfating to increase the number of sulfated saccharide residues in the NASP by 90% or more. In some instances, the NASP may be oversulfated to increase the number of sulfated saccharide residues in the NASP by a percentage that ranges from 5% to 99%, such as 10% to 90% and including 15% to 75%. In other embodiments, the NASP is oversulfated by to increase the number of sulfated saccharide residues in the NASP 1.5-fold or more, such as 2-fold or more, such as 3-fold or more and including oversulfating to increase the number of sulfated saccharide residues in the NASP by 5-fold or more. In some instances, the NASP may be oversulfated to increase the number of sulfated saccharide residues in the NASP in range from 2-fold to 10-fold, such as 3-fold, such as 4-fold and including oversulfating the NASP to increase the number of sulfated saccharide residues by 5-fold. In certain embodiments, the NASP may be oversulfated to a specific desired degree of sulfation, such as for example, to determine a threshold value for a degree of sulfation which is suitable for treating a subject having a blood coagulation disorder. For instance, a NASP may be oversulfated to increase the number of sulfated saccharide residues in the NASP such that the NASP has a final degree of sulfation which is 0.1 or greater, such as 0.2 or greater, such as 0.3 or greater, such as 0.75 or greater, such as 1.0 or greater, such as 1.25 or greater and including oversulfating a NASP to increase the number of sulfated saccharide residues in the NASP such that the NASP has a final degree of sulfation which is 1.5 or greater. In certain instances, the NASP may be oversulfated to increase the number of sulfated saccharide residues in the NASP such that the NASP has a final degree of sulfation which is 0.5 or greater. In some instances, the NASP is oversulfated to increase the number of sulfated saccharide residues in the NASP such that the NASP has a final degree of sulfation which ranges from 0.1 to 3.0, such as 0.5 to 2.5, such as 0.7 to 2.0 and including 1.0 to 1.5.

Likewise, the impact of degree of sulfation on procoagulant or anticoagulant activity may similarly be evaluated by desulfating a NASP having a predetermined degree of sulfation. For example, the NASP may be desulfated to reduce the number of sulfated saccharide residues in the NASP by 10% or more, such as 25% or more, such as 50% or more, such as 75% or more and including desulfating to reduce the number of sulfated saccharide residues in the NASP by 90% or more. In some instances, the NASP may be desulfated to decrease the number of sulfated saccharide residues in the NASP by a percentage that ranges from 5% to 99%, such as 10% to 90% and including 15% to 75%. In other embodiments, the NASP is desulfated to reduce the number of sulfated saccharide residues in the NASP by 1.5-fold or more, such as 2-fold or more, such as 3-fold or more and including desulfating to reduce the number of sulfated saccharide residues in the NASP by 5-fold or more. In some instances, the NASP may be desulfated to decrease the number of sulfated saccharide residues in the NASP in range from 2-fold to 10-fold, such as 3-fold, such as 4-fold and including oversulfating the NASP to increase the number of sulfated saccharide residues by 5-fold. In certain embodiments, the NASP may be desulfated to reduce the number of sulfated saccharide residues in the NASP to a specific desired degree of sulfation, such as for example, to determine a threshold value for a degree of sulfation which is suitable for treating a subject having a blood coagulation disorder. For instance, a NASP may be desulfated to reduce the number of sulfated saccharide residues in the NASP such that the NASP has a final degree of sulfation which is 2.0 or less, such as 1.75 or less, such as 1.5 or less, such as 1.25 or less, such as 1.0 or less, such as 0.75 or less and including desulfating a NASP to reduce the number of sulfated saccharide residues in the NASP such that the NASP has a final degree of sulfation which is 0.5 or less. In some instances, the NASP is desulfated to decrease the number of sulfated saccharide residues in the NASP such that the NASP has a final degree of sulfation which ranges from 0.1 to 3.0, such as 0.5 to 2.5, such as 0.7 to 2.0 and including 1.0 to 1.5.

In some embodiments, aspects of the present invention may include a method of oversulfating or desulfating a NASP followed by determining whether the oversulfated or desulfated NASP has increased procoagulant activity, decreased anticoagulant activity or both increased procoagulant activity and decreased anticoagulant activity as compared to an unmodified NASP. For example, the method may include the steps of: 1) determining the procoagulant or anticoagulant activity of a NASP (as described in detail above); 2) oversulfating or desulfating the NASP; 3) determining the procoagulant or anticoagulant activity of the oversulfated or desulfated NASP; 3) comparing the procoagulant or anticoagulant activity of the unmodified NASP with the procoagulant or anticoagulant activity of the oversulfated or desulfated NASP; and 4) determining whether the oversulfated or desulfated NASP has increased procoagulant activity, decreased anticoagulant activity or both increased procoagulant activity and decreased anticoagulant activity.

In other embodiments, methods of the invention may include oversulfating or desulfating a NASP followed by determining whether one or more of the unmodified NASP, oversulfated NASP or desulfated NASP may be suitable for treating a subject having a blood coagulation disorder. For example, the method may include the steps of 1) determining the procoagulant or anticoagulant activity of a NASP; 2) oversulfating or desulfating the NASP; 3) determining the procoagulant or anticoagulant activity of the oversulfated or desulfated NASP; 3) comparing the procoagulant or anticoagulant activity of the unmodified NASP with the procoagulant or anticoagulant activity of the oversulfated or desulfated NASP; 4) determining whether the oversulfated or desulfated NASP has increased procoagulant activity, decreased anticoagulant activity or both increased procoagulant activity and decreased anticoagulant activity as compared to an unmodified NASP; and 5) determining whether one or more of the unmodified NASP, oversulfated NASP or desulfated NASP may be suitable for treating a subject having a blood coagulation disorder based on the determined procoagulant and anticoagulant activity of the unmodified NASP, oversulfated NASP or desulfated NASP.

In certain embodiments, assessing the molecular structure includes visualizing the NASP by gel electrophoresis. Visualizing the NASP by gel electrophoresis is an efficient technique for determining the lot-to-lot variability of different NASP compositions. As such, gel electrophoresis may be employed to evaluate the consistency of NASP compositions obtained from different sources. Furthermore, the general purity, molecular size-to-charge ratio and affinity for barium may be determined based on gel electrophoresis. Any gel electrophoresis protocol may be employed for visualizing NASP compositions and may include, but is not limited to agarose gel or polyacrylamide gel electrophoresis.

In evaluating a NASP composition according to embodiments of the invention, methods also include assessing the chemical makeup of the NASP composition. By "chemical makeup" is meant any component apart from the NASP that is present in the NASP composition. As such, the chemical makeup of the NASP composition may include proteins, polysaccharides, trace elements, acids or bases, metals, ions, and various other impurities.

In some embodiments, assessing the chemical makeup of the NASP composition includes elemental analysis of the NASP composition. The term "elemental analysis" is used in its conventional sense to refer to determining the elemental and isotopic components of the NASP composition. Elemental analysis may be qualitative (i.e, determining which elements are present) and quantitative (i.e., determining how much of each element is present). In embodiments of the invention, determining the elemental components of the NASP composition may include determining the protein content (e.g., by determining the nitrogen content), the elemental sulfur content, and the impurity content of the NASP composition. Elemental analysis may be conducted by any convenient protocol, such as for example combustion analysis, gravimetry, optical atomic spectroscopy, flame atomic absorption, graphite furnace atomic absorption, inductively coupled plasma mass spectrometry, inductively coupled plasma atomic emission spectroscopy, sodium fusion, X-ray fluorescence, particle-induced X-ray emission, X-ray photoelectron spectroscopy, Auger electron spectroscopy and including by inductively coupled plasma analysis.

In certain instances, elemental analysis includes determining elemental sulfur content of the NASP composition. As discussed above, sulfur may be present in NASPs in the form of sulfate. As such, the amount of sulfur present in the NASP composition may vary. For example, the amount of sulfur may be 10 weight percent or less, such as 9.5 weight percent or less, such as 9.0 weight percent or less, such as 8 weight percent or less, such as 7 weight percent or less and including 5 weight percent or less. In some instances, the amount of sulfur present in the NASP composition ranges from 0.001 weight percent to 10 weight percent, such as 0.01 weigh percent to 9 weight percent, such as 0.1 weight percent to 8 weight percent and including 1 weight percent to 7 weight percent. Where the NASP composition includes a high amount of alginate (e.g., present in amounts greater than about 0.5%), determining the elemental sulfur content of the NASP composition may further include adjusting the weight percent of sulfur determined by elemental analysis to exclude the alginate content. By removing alginate, the calculated total weight of the NASP composition decreases and the weight percent of sulfur in these compositions will increase, giving a more accurate comparison of sulfur content amount NASP compositions. Elemental sulfur content may be determined using any convenient protocol, as described above. In certain instances, the elemental sulfur content is determined by inductively coupled plasma techniques or atomic emission spectroscopy and compared with elemental sulfur content as determined by colorimetric titration.

Depending on the source, the NASP composition may contain impurities. By "impurities" is meant any component of the NASP composition which may be undesirable or is detrimental to its application in treating a subject having a blood coagulation disorder. For example, impurities may interfere (i.e., diminish) or inhibit a particular desirable property of the NASP composition, such as for example procoagulant activity. Alternatively, impurities may not be detrimental to the function of the NASP, but may result in the NASP composition being unsuitable for administration to a subject, such as for example containing elevated levels of toxins, bacteria content or high levels of trace metal ions (e.g., arsenic, lead, cadmium or mercury) as described below Impurities may include, but are not limited to organic impurities such as protein, polysaccharides (e.g., alginate, laminaran and uronic acids), acetic acid and glycerol and inorganic impurities, such as trace elements and metal ions.

In certain embodiments, methods include determining the concentration of organic impurities in the NASP composition. In some instances, organic impurities include protein impurities. In these instances, the concentration of amino acids, peptides or proteins present in the NASP composition may be determined by protein-specific assays (e.g., bicinchoninic acid, Bradford Assay, etc.) or by elemental analysis of nitrogen content. Depending on the source of the NASP composition, the determined concentration of protein may vary, such as 5% by weight or less, such as 2% by weight or less, such as 1% by weight or less, such as 0.1% by weight or less, such as 0.05% by weight or less and including 0.01% by weight or less. In some instances, the determined concentration of protein ranges from 0.001% by weight to 5% by weight, such as 0.01% to 4.5% by weight and including 0.1% to 4% by weight.

In other instances, organic impurities include non-NASP polysaccharides. For example, the concentration of alginate and laminaran may be determined. Alginate is a polysaccharide composed of mannuronic acid with 1-4 linkages and is neither procoagulant nor anticoagulant. Laminaran is composed of glucose residues with 1-3 and 1-6 linkages. Non-NASP polysaccharides may be determined to be present in NASP composition in an amount that varies, ranging from 0.1% to 30% by weight, such as 1% to 25% by weight, such as 5% to 20% by weight, and including 5% to 15% by weight. Alginate and laminaran may be quantified by any convenient protocol, including $^{13}$C-NMR, ion chromatography or by uronic acid specific assays (e.g., carbazole assay).

In other embodiments, methods include determining the inorganic impurity content. For example, inorganic impurities may include trace elements and metal ions. In some instances, methods include identifying and quantifying one or more of silver, aluminum, arsenic, boron, barium, berrylium, bismuth, calcium, cadmium, cobolt, copper, iron, germanium, mercury, lithium, magnesium, manganese, molybdenum, sodium, nickel, phosphorus, lead, antimony, selenium, silicon, tin, strontium, titanium and zinc. Trace elements and metal ions (e.g., As, Cd Hg, Pb) may be determined to be present in the NASP compositions in amounts ranging from 0.05 µg/g to 3.0 µg/g, such as 0.1 µg/g to 2.5 µg/g, such as 0.25 µg/g to 2.0 µg/g, and including 0.5 µg/g to 1.5 µg/g. Trace elements and metal ions may be identified and quantified using any convenient protocol, such as for example mass spectrometry, ion chromatography, atomic absorption, graphite furnace atomic absorption spectrometry, inductively coupled plasma mass spectrometry, inductively coupled plasma atomic emission spectrometry, flame atomic absorption spectrometry, acidimetric titration, or any combination thereof.

As summarized above, one or more NASP compositions are evaluated to determine the coagulation activity and chemical makeup of the composition and the NASP molecular structure. In embodiments of the invention, methods may further include determining whether each NASP composition is suitable for treating a subject having a blood coagulation disorder based on the determined coagulation activities, chemical makeups and NASP molecular structures. In determining whether each NASP composition may be suitable, a human (either alone or with the assistance of a computer, if using a computer-automated process initially set up under human direction, as described below) assesses the determined coagulation activities, chemical makeups and NASP molecular structures and determines whether the NASP composition would be suitable or unsuitable for administering to a subject having a blood coagulation disorder.

Determining whether a NASP composition may be suitable for administering to a subject having a blood coagulation disorder may vary in terms of goal, where in some instances the desired characteristics of the NASP composition are characteristics that ultimately result in effectively treating a subject having a blood coagulation disorder. As such, the desired characteristics of the NASP composition may include one or more of: high procoagulant activity, wide procoagulant window, high TFPI-inhibiting activity, low contact pathway activation, low anticoagulant activity, large ratio of procoagulant activity to anticoagulant activity, high bioavailability, high purity, low polydispersity, high fucose content, high sulfur content, low alginate content, NASP having low molecular weight, consistent lot-to-lot production, and low impurity content or any combination thereof.

For example, after assessing the coagulation activity of the NASP composition, methods may include determining that a NASP composition may be suitable for treating a subject having a blood coagulation disorder where the NASP composition satisfies one or more of the following conditions:

the NASP composition increases in the overall rate of blood coagulation by 50% or more as compared to a suitable control, such as by 75%, such as by 95% and including by 99% as compared to a suitable control;

the NASP composition reduces the time required for blood to begin coagulating by 50% or more as compared to a suitable control, such as by 75%, such as by 90% and including by 95% as compared to a suitable control;

the concentration of the NASP composition required to produce peak thrombin generation ranges from 0.1 to 1.5 µg/mL, such as 0.5 µg/mL, including 1 µg/mL;

the procoagulant window of the NASP composition ranges from about 0.1 to 100 µg/mL or less;

the NASP composition corrects thrombin generation in factor-inhibited plasma to at least 2 times that found in normal plasma, such as 2.5 times that found in normal plasma, such as 3 times that found in normal plasma, including 5 times that found in normal plasma; the NASP composition corrects coagulation in FVIII-inhibited plasma to normal levels in a concentration range from 0.1 to 1.5 µg/mL, such as for example, 0.5 µg/mL, such as 0.9 µg/mL, such as 1.1 µg/mL, and including 1.3 µg/mL;

the $EC_{50}$ value for procoagulant activity of the NASP composition is 0.5 µg/mL or less, such as 0.4 µg/mL, such as 0.3 µg/mL, such as 0.2 µg/mL and including 0.1 µg/mL;

the ratio of the procoagulant activity to anticoagulant activity of the NASP composition is 10 or greater, such as 15, such as 20, such as 25, such as 30, such as 35, such as 40, such as 45 and including 50;

the NASP composition has an $EC_{50}$ for TFPI-inhibiting activity of 0.5 µg/mL or less, such as 0.4 µg/mL, such as 0.3 µg/mL, such as 0.2 µg/mL, including 0.1 µg/mL; and the concentration at which the NASP composition activates the contact pathway is 20-fold or greater than the $EC_{50}$ of the NASP composition, such as 30-fold, such as 35-fold, such as 40-fold and including 50-fold than the $EC_{50}$ of the NASP composition.

In other instances, after assessing the molecular structure of the one or more NASP compositions, a NASP composition may be determined to be suitable for treating a subject having a blood coagulation disorder where the NASP composition satisfies one or more of the following conditions:

the molecular weight of the NASP is 160 kDa or less, such as 150 kDa, such as 130 kDa and including a molecular weight which ranges from 15 kDa to 41 kDa;

the NASP has a degree of polymerization which ranges from 70 to 200, such as 75 to 175, such as 100 to 150 and including a degree of polymerization of 125;

the NASP has a ratio of linear saccharide residues to branching saccharide residues of 2.0 or less, such as 1.4, such as 1.3, such as 1.2 and including 1;

the NASP has a fucose content that is 60% or greater by weight, such as 75% by weight, such as 80% by weight and including 90% fucose content or by weight;

the NASP has an alginate content that is 10% or less by weight, such as 8% by weight, including 5% alginate content by weight;

the NASP has a fucose content that is 80% or greater by weight and an alginate content that 10% or less by weight, such as 85% fucose by weight and 5% alginate content by weight;

the NASP has an anionic charge density which ranges from 0.5 to 0.6, such as 0.51, such as 0.52 and including an anionic charge density of 0.55;

the NASP has a degree of sulfation which is 0.5 or greater, such as 0.55, such as 0.6, such as 0.65, such as 0.7, such as 1.0 and including 1.5; or the sulfur content of the NASP is 8% sulfur or greater by weight, such as 9% sulfur by weight, such as 10% sulfur by weight, including 15% sulfur by weight.

In yet other instances, after assessing the chemical makeup of the one or more NASP compositions, methods include determining that a NASP composition may be suitable for treating a subject having a blood coagulation disorder if the NASP composition has an impurity content that is 1% or less by weight, such as 0.5% by weight, including an impurity content that is 0.1% by weight.

In some embodiments, determining that a NASP composition is suitable for administering to a subject having a blood coagulation disorder includes requiring that the NASP composition possess more than one of the above desired characteristics, such as 2 of the above desired characteristics, such as 3, such as 4, such as 5, such as 6, such as 7, such as 8, and including 10 of the above desired characteristics. In some embodiments, determining that a NASP composition is suitable includes determining that the NASP composition possesses particular desired characteristics. For example, in certain instances, a NASP composition may be determined to be suitable where the composition has an $EC_{50}$ of 0.3 µg/mL or less, a procoagulant window of 0.1 to 100 µg/mL and a ratio of procoagulant activity to anticoagulant activity of 25 or greater. In other instances, a NASP composition may be determined to be suitable where the composition has a molecular weight of 160 kDa or less, a fucose content that is 60% or greater, an alginate content that is 10% or less and a weight percent of sulfur that is 8% or greater. In other instances, determining that a NASP composition may be suitable includes determining that the composition has an $EC_{50}$ of 0.3 µg/mL or less, an $EC_{50}$ for TFPI-inhibiting activity of 0.4 µg/mL or less, a molecular weight of 160 kDa or less, a fucose content that is 70% or greater by weight, an alginate content that is 7% or less by weight and no contact pathway activation up to 100 µg/mL or more. In other instances, determining that a NASP composition may be suitable includes determining that the composition includes a NASP which has a molecular weight ranging from 15 kDa to 41 kDa, a degree of polymerization ranging from 70 to 200, a degree of sulfation of 0.5 or greater. In other instances, determining that a NASP composition may be suitable includes determining that the composition includes a NASP which has a molecular weight ranging from 15 kDa to 41 kDa, a degree of polymerization ranging from 70 to 200, a degree of sulfation of 0.5 or greater, a fucose content that is 70% or greater by weight, a sulfur content of 8% or greater by weight and an alginate content that is 7% or less by weight. In other instances, determining that a NASP composition may be suitable includes determining that the composition has an $EC_{50}$ of 0.3 µg/mL or less, an $EC_{50}$ for TFPI-inhibiting activity of 0.4 µg/mL or less and includes a NASP which has molecular weight ranging from 15 kDa to 41 kDa, an anionic charge density ranging from 0.5 to 0.6, a degree of polymerization ranging from 70 to 200 and a degree of sulfation ranging from 0.5 to 0.6, a fucose content that is 70% or greater by weight, a sulfur content of 8% or greater by weight, an alginate content that is 7% or less by weight and no contact pathway activation up to 100 µg/mL or more.

As noted above, depending on the subject and type of blood coagulation disorder, any combination of the above specified desired characteristics may be used as criteria for determining whether a NASP composition is suitable for treating a subject having a blood coagulation disorder. In other words, any combination of one or more of the above desired characteristics can be used to screen NASP compositions for specific properties as desired.

Certain characteristics may be given more emphasis than others in determining whether a NASP composition may be suitable for treating a subject having a blood coagulation disorder, as desired. For example, coagulation activity may be given more emphasis than structural elements. On the other hand, structural elements may be given more emphasis than coagulation activity. Likewise, coagulation activity and structural elements may be given more emphasis than impurity content.

Where it is immediately apparent that a NASP composition is unsuitable for administering to a subject having a blood coagulation disorder, the NASP composition may be ruled out at any time during methods of the invention. For example, the NASP composition may be immediately ruled out after determining the coagulation activity, after determining the molecular structure or after determining the chemical makeup of the NASP composition. In some instances, a NASP composition is ruled out immediately because it contains toxic impurities. In other instances, a NASP composition is ruled out immediately because it exhibits no procoagulant activity. In yet other instances, a NASP composition is ruled out immediately because the molecular weight of the NASP is too large to be bioavailable.

Aspects of the invention also include in certain embodiments, methods for screening a plurality of NASP compositions to identify one or more NASP compositions that may be suitable for treating a subject having a blood coagulation disorder. As such, methods include determining the coagulation activity, chemical makeup and the NASP molecular structure of a plurality of NASP compositions and comparing the determined coagulation activities, chemical makeups and NASP molecular structures with each other and identifying whether one or more NASP compositions may be suitable for treating a subject having a blood coagulation disorder. After determining the coagulation activity, chemical makeup and NASP molecular structure of each of the NASP compositions, a human (either alone or with the assistance of a computer) compares the determined characteristics of the NASP compositions to identify one or more NASP compositions that may be suitable.

The plurality of NASP compositions may be evaluated by determining the coagulation activities, chemical makeups and NASP molecular structures as described above. After evaluating the NASP compositions by determining the coagulation activities, chemical makeups and NASP molecular structures, methods include comparing the plurality of NASP compositions to assess whether one or more of the NASP compositions may be suitable for treating a subject having a blood coagulation disorder.

In some embodiments, comparing the plurality of the NASP compositions includes ranking the NASP compositions with respect to each desired characteristic (e.g., high procoagulant activity, wide procoagulant window, high TFPI-inhibiting activity, low contact pathway activation, low anticoagulant activity, large ratio of procoagulant activity to anticoagulant activity, high bioavailability, high purity, low polydispersity, high fucose content, high sulfur content, low alginate content, NASP having low molecular weight, consistent lot-to-lot production, and low impurity content) As such, each NASP composition is assigned a ranking with respect to each characteristic. After ranking the NASP compositions with respect to each characteristic, a total cumulative ranking may be calculated. Based on the total cumulative ranking, the suitability of the NASP composition for treating a subject having a blood coagulation disorder is determined. An example of screening a plurality of NASP compositions to identify whether one or more of the compositions may be suitable for treating a subject having a blood coagulation disorder is illustrated in Example 4 below.

Depending on the subject and type of blood coagulation disorder, the ranking of the NASP composition in each characteristic may contribute differently to the total cumulative ranking. In other words, not all characteristics will contribute equally to the total cumulative ranking, where some characteristics may be weighted more heavily than others depending on the ultimate goal in employing the NASP composition. For instance, coagulation activity may be given a higher emphasis than structural characteristics. In other instances, structural characteristics are given a higher emphasis than coagulation activity. For example, the procoagulant activity of the NASP composition may contribute more in identifying a suitable NASP composition than the molecular weight of the NASP. Likewise, the TFPI-inhibiting activity may be weighted more heavily than sulfur content.

The contribution of each characteristic to the total cumulative ranking of the NASP composition may be assigned as desired. In certain embodiments, the coagulation activity of the NASP composition makes a larger contribution to the total cumulative ranking than the molecular structure of the NASP. In other embodiments, the procoagulant activity makes a larger contribution to the total cumulative ranking than anticoagulant activity. In yet other embodiments, the monosaccharide content of the NASP makes a larger contribution to the total cumulative ranking than the molecular weight of the NASP.

After calculating the total cumulative ranking, the suitability of the plurality of NASP compositions for treating a subject having a blood coagulation disorder is determined based on the total cumulative ranking.

In some embodiments, one or more NASP compositions are determined to be suitable if its total cumulative ranking exceeds a predetermined threshold. In these instances, any number of the plurality of NASP compositions may be determined to be suitable (i.e, zero to all of the NASP compositions). For example, none of the screened NASP compositions may exceed the predetermined threshold and thus, none are identified as being suitable. Alternatively, all of the screened NASP compositions may exceed the predetermined threshold and thus, all of the NASP compositions are identified as being suitable.

In other instances, only the NASP composition having the highest total cumulative total ranking is selected. In other words, only the NASP composition with the highest ranking is considered a possible candidate for treating a subject having a blood coagulation disorder.

In other embodiments, each NASP composition may be given a rank based on the number of desired characteristics the NASP composition possesses. For example, a NASP composition may have 2 desired characteristics, such as 3, such as 4 such as 5, including 10 desired characteristics. In these embodiments, a NASP composition may be determined to be suitable if the total number of desired characteristics the NASP composition possesses exceeds a predetermined threshold. For example, the threshold may be 1 or more desired characteristics, such as 2, such as 3, such as 5, such as 10 desired characteristics. Alternatively in some instances, only the NASP composition with the most number of desired characteristics is selected as being suitable.

Compositions Suitable for Treating a Subject Having a Blood Coagulation Disorder Aspects of the invention also include compositions which are suitable for treating a subject having a blood coagulation disorder. NASP compositions which may be suitable for administering to a subject having a blood coagulation disorder may vary in terms of goal, as described above, where in some instances the desired characteristics of the NASP composition are characteristics that ultimately result in effectively treating a subject having a blood coagulation disorder. As such, the desired characteristics of the NASP composition may include one or more of: high procoagulant activity, wide procoagulant window, high TFPI-inhibiting activity, low contact pathway activation, low anticoagulant activity, large ratio of procoagulant activity to anticoagulant activity, high bioavailability, high purity, low polydispersity, high fucose content, high sulfur content, low alginate content, high degree of sulfation, NASP having low molecular weight, consistent lot-to-lot production, and low impurity content or any combination thereof.

In embodiments of the invention, NASP compositions of interest include compositions which satisfy one or more of the following conditions:

the NASP composition increases in the overall rate of blood coagulation by 50% or more as compared to a suitable control, such as by 75%, such as by 95% and including by 99% as compared to a suitable control;

the NASP composition reduces the time required for blood to begin coagulating by 50% or more as compared to a suitable control, such as by 75%, such as by 90% and including by 95% as compared to a suitable control;

the concentration of the NASP composition required to produce peak thrombin generation ranges from 0.1 to 1.5 µg/mL, such as 0.5 µg/mL, including 1 µg/mL;

the procoagulant window of the NASP composition ranges from about 0.1 to 100 µg/mL or less;

the NASP composition corrects thrombin generation in factor-inhibited plasma to at least 2 times that found in normal plasma, such as 2.5 times that found in normal plasma, such as 3 times that found in normal plasma, including 5 times that found in normal plasma; the NASP composition corrects coagulation in FVIII-inhibited plasma to normal levels in a concentration range from 0.5 to 1.5 µg/mL, such as for example, 0.7 µg/mL, such as 0.9 µg/mL, such as 1.1 µg/mL, and including 1.3 µg/mL;

the $EC_{50}$ value for procoagulant activity of the NASP composition is 0.5 µg/mL, such as 0.4 µg/mL, such as 0.3 µg/mL, such as 0.2 µg/mL and including 0.1 µg/mL;

the ratio of the procoagulant activity to anticoagulant activity of the NASP composition is 10 or greater, such as 15, such as 20, such as 25, such as 30, such as 35, such as 40, such as 45 and including 50;

the NASP composition has an $EC_{50}$ for TFPI-inhibiting activity of 0.5 µg/mL or less, such as 0.4 µg/mL, such as 0.3 µg/mL, such as 0.2 µg/mL, including 0.1 µg/mL; and the concentration at which the NASP composition activates the contact pathway is 30-fold or greater than the $EC_{50}$ of the NASP composition, such as 35-fold, such as 40-fold and including 50-fold than the $EC_{50}$ of the NASP composition;

the molecular weight of the NASP is 160 kDa or less, such as 150 kDa, such as 130 kDa and including a molecular weight which ranges from 15 kDa to 41 kDa but greater than or equal to 15 kDa;

the NASP has a degree of polymerization which ranges from 70 to 200, such as 75 to 175, such as 100 to 150 and including a degree of polymerization of 125;

the NASP has a ratio of linear saccharide residues to branching saccharide residues of 2.0 or less, such as 1.6, such as 1.5, such as 1.4, such as 1.3, such as 1.2 and including 1;

the NASP has a fucose content that is 60% or greater by weight, such as 75%, such as 80% and including 90% fucose content by weight;

the NASP has an alginate content that is 10% by weight, such as 8% by weight, including 5% alginate content by weight;

the NASP has a fucose content that is 60% or greater by weight and an alginate content that 10% by weight, such as 75% fucose by weight and 5% alginate content by weight;

the NASP has an anionic charge density which ranges from 0.5 to 0.6, such as 0.51, such as 0.52 and including an anionic charge density of 0.55;

the NASP has a degree of sulfation which is 0.5 or greater, such as 0.7, such as 1.0 and including 1.5; or the sulfur content of the NASP is 8% sulfur or greater by weight, including 10% sulfur by weight, including 15% sulfur by weight;

the NASP composition has an impurity content that is 1% or less by weight, such as 0.5% by weight, including an impurity content that is 0.1% by weight.

In some embodiments, NASP compositions suitable for administering to a subject having a blood coagulation disorder include NASP compositions which possess more than one of the above desired characteristics, such as 2 of the above desired characteristics, such as 3, such as 5, such as 6, such as 7, such as 8, and including 10 of the above desired characteristics.

In certain embodiments, NASP compositions of interest are compositions which possesses particular desired properties or include NASPs which have specific structural characteristics. For example, in certain instances, suitable NASP compositions include NASP compositions which have an $EC_{50}$ of 0.3 µg/mL or less, a procoagulant window of 0.1 to 100 µg/mL and a ratio of procoagulant activity to anticoagulant activity of 10 or greater. In other instances, suitable NASP compositions include NASP compositions which have a molecular weight of 160 kDa or less, a fucose content that is 60% or greater, an alginate content that is 10% or less and a weight percent of sulfur that is 8% or greater. In other instances, suitable NASP compositions include NASP compositions which have an $EC_{50}$ of 0.3 µg/mL or less, an $EC_{50}$ for TFPI-inhibiting activity of 0.4 µg/mL or less, a molecular weight of 160 kDa or less, a fucose content that is 70% or greater by weight, an alginate content that is 7% or less by weight and no contact pathway activiation up to 100 µg/mL or more. In other instances, suitable NASP compositions include NASPs having a molecular weight ranging from 15 kDa to 41 kDa, a degree of polymerization ranging from 70 to 200, a degree of sulfation of 0.5 or greater. Suitable NASP compositions may also include NASP compositions which have a NASP having a molecular weight ranging from 15 kDa to 41 kDa, a degree of polymerization ranging from 70 to 200, a degree of sulfation of 0.5 or greater, a fucose content that is 70% or greater by weight, a sulfur content of 8% or greater by weight and an alginate content that is 7% or less by weight. Suitable NASP compositions may also include NASP compositions which have an $EC_{50}$ of 0.3 µg/mL or less, an $EC_{50}$ for TFPI-inhibiting activity of 0.4 µg/mL or less and includes a NASP which has molecular weight ranging from 15 kDa to 41 kDa, an anionic charge density ranging from 0.5 to 0.6, a degree of polymerization ranging from 70 to 200 and a degree of sulfation ranging from 0.5 to 0.6, a fucose content that is 70% or greater by weight, a sulfur content of 8% or greater by weight, an alginate content that is 7% or less by weight and no contact pathway activiation up to 100 µg/mL or more.

Aspects of the invention also include compositions that are composed of 50% or greater by weight NASPs that satisfy one of more of the above-recited conditions, such as 80% or greater by weight, such as 85% or greater by weight, such as 90% or greater by weight, such as 95% or greater by weight and including compositions which are composed of 99% or greater by weight NASPs that satisfy one or more of the above-recited conditions. In other words, NASP compositions of the invention according to certain embodiments are an enriched composition of NASPs composed of at least 50% by weight NASPs which satisfy one or more of the above-recited conditions and are not merely mixtures which contain a small amount of NASPs which satisfy one or more of the above-recited conditions with a large amount of NASPs which do not satisfy one or more of the above-recited conditions. In some instances, compositions of interest include NASP compositions that are composed of NASPs that satisfy one or more of the above-recited conditions in an amount that ranges from 50% to 99% by weight of the NASP composition, such as 55% to 90%, such as 60% to 85% and including 65% to 75% by weight of the NASP composition.

For example, in one instance, NASP compositions may include compositions which are composed of 50% or greater by weight NASPs which have a degree of sulfation that is 0.5 or greater, such as 75% or greater by weight and including 95% or greater by weight NASPs which have a degree of sulfation that is 0.5 or greater. In some instances, NASP compositions may include compositions which are composed of NASPs which have a degree of sulfation that is 0.5 or greater in an amount that ranges from 50% to 99% by weight of the NASP composition, such as 55% to 90%, such as 60% to 85% and including 65% to 75% by weight of the NASP composition. In certain embodiments, NASP compositions of interest include compositions which are composed of 50% or greater by NASPs which have a degree of sulfation that is 1.0 or greater and including a degree of sulfation of 1.3 or greater.

In other instances, NASP compositions may include compositions which are composed of 50% or greater by weight NASPs which have a degree of polymerization that ranges from 70 to 200, such as 75% or greater by weight and including 95% or greater by weight NASPs which have a degree of polymerization that ranges from 70 to 200. In some instances, NASP compositions may include compositions which are composed of NASPs which have a degree of polymerization that ranges from 70 to 200 in an amount that ranges from 50% to 99% by weight of the NASP composition, such as 55% to 90%, such as 60% to 85% and including 65% to 75% by weight of the NASP composition.

In other instances, NASP compositions may include compositions which are composed of 50% or greater by weight NASPs which have a fucose content that is 60% or greater, such as 75% or greater by weight and including 95% or greater by weight NASPs that have a fucose content of 60% or greater. In certain embodiments, NASP compositions of interest include compositions which are composed of 50% or greater by weight NASPs that have a fucose content that is 90% or greater. In some instances, NASP compositions may include compositions which are composed of NASPs which have a fucose content that is 60% or greater in an amount that ranges from 50% to 99% by weight of the NASP composition, such as 55% to 90%, such as 60% to 85% and including 65% to 75% by weight of the NASP composition.

In other instances, NASP compositions may include compositions that are composed of 50% or greater by weight NASPs which have an $EC_{50}$ value for procoagulant activity of 0.2 µg/mL or less, such as 75% or greater by weight and including 95% or greater by weight NASPs which have an $EC_{50}$ value for procoagualant activity of 0.2 µg/mL or less. In certain embodiments, NASP compositions of interest include compositions which are composed of 50% or greater by weight NASPs which have an $EC_{50}$ value for procoagulant activity of 0.1 µg/mL or less. In some instances, NASP compositions may include compositions which are composed of NASPs which have an $EC_{50}$ value for procoagulant activity of 0.2 µg/mL or less in an amount that ranges from 50% to 99% by weight of the NASP composition, such as 55% to 90%, such as 60% to 85% and including 65% to 75% by weight of the NASP composition.

In yet other instances, NASP compositions may include compositions which are composed of 50% or greater by weight NASPs that have a ratio of linear saccharide residues to branching saccharide residues of 1.4 or less, such as 75% or greater by weight and including 95% or greater by weight NASPs that have a ratio of linear saccharide residues to branching saccharide residues of 1.4 or less. In other words, in these embodiments NASP compositions of interest are composed of NASPs where one in every 1.4 saccharide residues or less has a branching saccharide residue attached to it. In certain embodiments, NASP compositions of interest include compositions which are composed of 50% or greater by weight NASPs that have a ratio of linear saccharide residues to branching saccharide residues of 1 or less. In some instances, NASP compositions may include compositions which are composed of NASPs which have a ratio of linear saccharide residues to branching saccharide residues of 1.4 or less in an amount that ranges from 50% to 99% by weight of the NASP composition, such as 55% to 90%, such as 60% to 85% and including 65% to 75% by weight of the NASP composition.

Compositions of interest may also include one or more blood coagulation factors. For example, compositions of the invention may include an amount of one or more NASPs in combination with one or more blood coagulation factors. Blood coagulation factors of interest include, but are not limited to factor XI, factor XII, prekallikrein, high molecular weight kininogen (HMWK), factor V, factor VII, factor VIII, factor IX, factor X, factor XIII, factor II, factor VIIa, and von Willebrands factor, factor Xa, factor IXa, factor XIa, factor XIIa, and VIIIa, prekallekrein, and high-molecular weight kininogen, tissue factor, factor VIIa, factor Va, and factor Xa.

The amount (i.e, mass) of each of the NASPs and blood coagulation factor in compositions of the invention may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg.

Compositions of the invention may be homogeneous, containing only a single type of NASP. In other embodiments, compositions of interest are heterogenous mixtures of two or more different NASPs. For example, heterogenous mixtures may contain two or more NASPs that vary with respect to monosaccharide content, sulfur content, degree of sulfation as well as NASPs having heterogenous or homogeneous distributions of molecular weight.

In certain embodiments, compositions of the invention may further include one or more pharmaceutically acceptable excipients as part of a pharmaceutical composition. Excipients may include, but are not limited to, carbohydrates, inorganic salts, antimicrobial agents, antioxidants, surfactants, buffers, acids, bases, and any combinations thereof. Excipients suitable for injectable compositions may include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer may also be employed. Some carbohydrate excipients of interest include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. Inorganic salts may include, but are not limited to citric acid, sodium chloride, potassium chloride, sodium sulfate, potassium nitrate, sodium phosphate monobasic, sodium phosphate dibasic, and any combinations thereof.

In certain embodiments, compositions of the invention may also include an antimicrobial agent for preventing or deterring microbial growth, such as for example benzalkonium chloride, benzethonium chloride, benzyl alcohol, cetylpyridinium chloride, chlorobutanol, phenol, phenylethyl alcohol, phenylmercuric nitrate, thimersol, and any combinations thereof.

One or more antioxidants may also be employed. Antioxidants, which can reduce or prevent oxidation and thus deterioration of the composition, may include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and any combinations thereof.

One or more surfactants may also be included in compositions of the invention. For example, suitable surfactants may include, but are not limited to polysorbates, such as "Tween 20" and "Tween 80," and pluronics such as F68 and F88 (BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other cations.

Acids or bases may also be present in compositions of the invention. For example, acids may include but are not limited to hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and any combinations thereof. Examples bases include, but are not limited to sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and any combinations thereof.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, such as from about 5% to about 98% by weight, such as from about 15 to about 95% by weight of the excipient, including less than 30% by weight. Pharmaceutical excipients along with other excipients that may be employed in compositions of the invention are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000, the disclosure of which is herein incorporated by reference.

As described above, compositions of the invention may be administered by any convenient mode of administration. As such, the formulation may vary. For example, compositions of the invention may be an injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. In embodiments where compositions of the invention are employed for injections, diluents for reconstituting solid compositions prior to injection may include, but is not limited to bacteriostatic water for injection, dextrose 5% in water, phosphate buffered saline, Ringer's solution, saline, sterile water, deionized water, and any combinations thereof. In some embodiments, pharmaceutical compositions of the invention may be in the form of a liquid solution or suspension, syrup, cream, ointment, tablet, capsule, powder, gel, matrix, suppository, or any combination thereof.

Compositions of the invention may be pre-loaded into a syringe, an implantation device, or the like, depending upon the intended mode of delivery and use. In certain embodiments, the compositions are in unit dosage form, such that an amount of the composition is ready in a single dose, in a premeasured or pre-packaged form.

Systems for Evaluating One or More NASP Compositions

Aspects of the invention further include systems for practicing methods of the invention. In certain embodiments, systems include a computer that includes a computer readable storage medium having a computer program stored thereon, where the computer program when loaded on a computer operates the computer to: receive coagulation activity data, chemical makeup data and molecular structure data about the one or more NASP compositions and includes a processor to evaluate the inputted coagulation activity data, chemical makeup data and molecular structure data to determine whether one or more of the NASP compositions may be suitable for treating a subject having a blood coagulation disorder.

In embodiments of the invention, the system includes an input module, a processing module and an output module. In some embodiments, the subject systems may include an input module which is connected to the Internet such that data from the determined NASP compositions may be inputted from a remote location. The processing module includes memory having a plurality of instructions for assessing the coagulation activity, chemical makeup and NASP molecular structure of one or more NASP compositions. The processing module is also configured with an algorithm to determine whether one or more of the NASP compositions may be suitable for treating a subject having a blood coagulation disorder based on the assessment of the coagulation activity data, chemical makeup data and NASP molecular structure data received from a user. For example, the processor is configured with memory with instructions to perform the steps as described above to evaluate whether one or more NASP compositions may be suitable or to screen a plurality of NASP compositions.

After the processing module has assessed the coagulation activity, chemical makeup and molecular structure of the one or more NASP compositions and determined whether one or more of the NASP compositions may be suitable for treating a subject having a blood coagulation disorder, an output module communicates the results to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for evaluating the inputted data about the NASP compositions and determining whether one or more of the NASP compositions may be suitable for treating a subject having a blood coagulation disorder. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Pert, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The processor may also have access to a communication channel to communicate with a user at a remote location By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e, smartphone). In these embodiments, input manager receives information, e.g., coagulation activity data, chemical makeup data, molecular structure data, etc., from a user e.g., over the Internet, telephone or satellite network. Input manager processes and forwards this information to the processing module. These functions are performed using any convenient technique.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module (e.g., the identity of one or more NASP compositions that may be suitable for treating a subject having a coagulation disorder) to a user at a remote location, e.g, over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Sun Solaris, Linux, OS/400, Compaq Tru64 Unix, SGI IRIX, Siemens Reliant Unix, and others.

During use, a user enters information about the coagulation activity, chemical makeup and molecular structure of one or more NASP compositions using the input devices of the system, as determined by the methods described in detail above. The processing module is configured to assess the coagulation activity data, chemical makeup data and molecular structure data of the NASP compositions and determine whether one or more NASP compositions are suitable to treating a subject having a blood coagulation disorder. Systems of the invention may screen a plurality of the NASP compositions, such as by comparing and ranking the NASP compositions, such as described above or systems may evaluate one or more NASP compositions and determine whether each NASP composition is suitable using the desired characteristics method.

In certain embodiments, the processing module is also configured to include a data customizing manager. The data customizing manager is a functional element that allows the user to input various parameters for evaluating the coagulation activity data, chemical makeup data and NASP molecular structure data. Furthermore, the data customizing manager is also configured so that a user can input or change criteria used to determine whether a NASP composition is suitable for treating a subject having a blood coagulation disorder. For example, using the data customizing manager a user may customize which characteristics of the NASP composition data to weigh more heavily in determining the suitability of a NASP composition. In this manner, the data customizing manager is a functional element that allows the user to customize the evaluation protocol used in determining whether a NASP composition is suitable for treating a subject having a coagulation disorder.

In certain embodiments, the processing module is also configured to include an input information manager. The input information manager provides information to a user regarding the criteria that was employed by the processor in determining whether a NASP is suitable for treating a subject having a blood coagulation disorder. For example, the input information manager provides a history of input information to a user at the request of the user. The input information may be in the form of a compendium of coagulation activity data, chemical makeup data and molecular structure data for particular NASP compositions as well as parameters used in determining whether it is suitable for treating a subject having a blood coagulation disorder and may be organized temporally or according to some other criterion, etc. As such, the input information manager provides a user the ability to retrace the steps employed in designing a protocol for determining NASP composition suitability, so that knowledge of the data that went into the development of the protocol can be readily obtained and used.

In certain embodiments, the processing module is configured to include a NASP composition comparison manager. The comparison manager is a functional element that is configured to compare one or more NASP composition to each other or to a database of NASP compositions. In comparing a given NASP composition to each other or to a database of NASP composition, the comparison manager may search for similar NASP compositions in the database, and allow the user to visually compare coagulation activity data, chemical makeup data and NASP molecular structure data of the subject NASP composition with a plurality of NASP compositions in the database. The comparison manager may also compare the subject NASP composition to the database of NASP compositions and identify, based on this comparison, characteristics for why the NASP composition may or may not be suitable for treating a subject having a coagulation disorder as compared to those in the database.

In certain embodiments, the processing module of the system is further configured to include a collaboration manager configured to allow at least two different users to jointly provide data about one or more NASP compositions.

In using the subject systems, a user inputs coagulation activity, chemical makeup and NASP molecular structure (such as determined by the methods described above) into the input module of the system, e.g., via a user computer. In certain embodiments, the system takes the provided information and generates a report identifying one or more NASP compositions that may be suitable for treating a subject having a blood coagulation disorder. The report is forwarded to the user, e.g., via the output display or is printed. In some instances, the report, and coagulation activity, chemical makeup and molecular structure data used to generate the report, is stored on the system in a suitable memory element, where the stored information may be accessed at a later time, such as to compare with another NASP composition.

Systems of the invention further include an output manager that generates a report based on information received from one or more users, e.g., coagulation activity, chemical makeup or molecular structure information. The output manager is a functional element that produces a report in response to receiving information and determining whether one or more NASP compositions are suitable for treating a subject having a blood coagulation disorder.

Utility

The subject methods and systems find use in any situation where there is a desire to identify one or more compositions that may enhance blood coagulation in a subject. In certain embodiments, the subject methods may be employed to identify one or more compositions for treating bleeding disorders, such as a chronic or acute bleeding disorder, a congenital coagulation disorder caused by a blood factor deficiency, an acquired coagulation disorder and administration of an anticoagulant. In another aspect, the invention provides a method for screening a plurality of compositions and comparing characteristics of the compositions to determine whether one or more of the compositions may be suitable to treat a subject having a blood coagulation disorder. Bleeding disorders may include, but are not limited to hemophilia A, hemophilia B, von Willebrand disease, idiopathic thrombocytopenia, a deficiency of one or more contact factors, such as Factor XI, Factor XII, prekallikrein, and high molecular weight kininogen (HMWK), a deficiency of one or more factors associated with clinically significant bleeding, such as Factor V, Factor VII, Factor VIII, Factor IX, Factor X, Factor XIII, Factor II (hypoprothrombinemia), and von Willebrand factor, a vitamin K deficiency, a disorder of fibrinogen, including afibrinogenemia, hypofibrinogenemia, and dysfibrinogenemia, an $alpha_2$-antiplasmin deficiency, and excessive bleeding such as caused by liver disease, renal disease, thrombocytopenia, platelet dysfunction, hematomas, internal hemorrhage, hemarthroses, surgery, trauma, hypothermia, menstruation, and pregnancy.

The subject methods and systems also find use in identifying compositions which may be suitable for enhancing blood coagulation to treat a congenital coagulation disorder or an acquired coagulation disorder caused by a blood factor deficiency. The blood factor deficiency may be caused by deficiencies of one or more factors, including but not limited to, factor V, factor VII, factor VIII, factor IX, factor XI, factor XII, factor XIII, and von Willebrand factor.

EXPERIMENTAL

The following examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Fucoidans and Other Reagents

Fucoidan lots from four different brown algae species were evaluated: *Laminaria japonica* (L.j.) (Baxter Innovations GmbH, Austria); and *Fucus vesiculosus* (F.v.), *Undaria pinnatifida* (U.p.), and *Ecklonia maxima* (E.m.) (Marinova, Australia). Chemicals and reagents were all analytical grade.

Clotting Assays

Calibrated Automated Thrombography (CAT)

The procoagulant activity of fucoidans was monitored by calibrated automated thrombography (CAT) as described by Hemker et al. (Pathophysiol. Haemost. Thromb. 33: pp. 4-15), the disclosure of which is herein incorporated by reference. As a model for antibody mediated FVIII deficiency, a normal human plasma pool (George King Biomedical, Overland Park, Kans.) was incubated with anti-human FVIII plasma raised in goat (Baxter Bioscience, Austria). An optimized heat inactivation process ensured that goat coagulation factors in the inhibitor plasma were inactive. The final inhibitor concentration in the plasma was 50 Bethesda units (BU/mL), which was experimentally determined to completely block FVIII activity. For specific inhibition of factor XIIa, the plasmas were mixed with corn trypsin inhibitor (CTI) (Hematologic Technologies, Inc., Essex Junction, Vt., USA), providing a final CTI concentration of 40 µg/mL. To each well of a 96 well micro-plate (Immulon 2HB, U-bottom; Thermo Electron), 80 µL of pre-warmed (37° C.) plasma sample was added. A range of 0.02-300 µg/mL of each fucoidan preparation was added to the plasma (10 µL). Thrombin generation was monitored at 37° C. in a Fluoroskan Ascent reader (Thermo Labsystems, Helsinki, Finland) using FluCa and PPP-reagents (Thrombinoscope BV, Maastricht, The Netherlands). Thrombin generation was triggered by 1 µM tissue factor and 4 µM phospholipids and started by dispensing 20 µL of FluCa reagent (Thrombinoscope BV, Maastricht, The Netherlands) containing fluorogenic substrate and HEPES buffered $CaCl_2$ solution (100 mM) into each well. Fluorescence measurements were performed in a Fluoroskan Ascent® reader (Thermo Labsystems, Helsinki, Finland; filters 390 nm excitation and 460 nm emission) at 37° C. All samples were analyzed in duplicate and in at least two independent assays.

The parameters of the resulting thrombin generation curves were calculated using the Thrombinoscope™ software (Thrombinoscope BV, Maastricht, The Netherlands). With the thrombin calibrator as a reference, the molar concentration of thrombin in the test wells was derived. The thrombin amounts at the peak of each thrombin generation curve (peak thrombin, nM), lag time (time interval between starting measurement and start of thrombin generation), peak time (time interval between starting measurement and peak thrombin), and endogenous thrombin potential (area under the curve of thrombin concentration versus time) were recorded. The procoagulant effect was assessed by plotting the thrombin peak against the concentration within the inclining part of the profile. The $EC_{50}$ was derived using the SigmaPlot 12 software from the resulting sigmoidal curve.

To evaluate the contact activation of fucoidans, CAT assays were performed in normal human plasma pool as described above with and without CTI.

TFPI—Dilute Prothrombin Time Assay (TFPI-dPT)

A dPT assay with added TFPI (TFPI-dPT) was used to demonstrate the TFPI-inhibiting effect of NASPs in normal human plasma (George King Biomedical). Plasma samples were pre-incubated with 0.5 µg/mL full-length TFPI (aa 1-276, constitutively produced by SKHep1 cells) and samples of NASPs (0.03-10 µg/mL) for 15 mM at room temperature.

TFPI inhibition was tested using tissue factor reagent TriniClot PT Excel S (Trinity Biotech), which was diluted in Hepes-buffered saline 1:666 with 0.5% BSA was added to the plasma samples on an ACL Pro Elite hemostasis analyzer. Clotting was initiated with 25 mM $CaCl_2$. The volume ratio of plasma:TF:$CaCl_2$ was 1:1:1. Plotting the clotting time against the log of fucoidan concentration resulted in a sigmoidal curve. The $EC_{50}$ was derived using the SigmaPlot 12 software from the graph.

Activated Partial Thromboplastin Time Assay (aPTT)

The aPTT assay was performed as described in Liu, et al. (Thromb. Haemost. 95: pp. 68-76), the disclosure of which is herein incorporated by reference. Briefly, 50 µL of thawed normal human plasma pool (George King Biomedical, Overland Park, Kans.) was mixed with 5 µL of fucoidan sample (0-60 µg/mL final plasma concentration). Fucoidans were diluted in imidazole buffer (3.4 g/L imidazole; 5.85 g/L NaCl, pH 7.4) containing 1% albumin (Baxter, Austria). After addition of 50 µL aPTT reagent (STA APTT, Roche) the samples were incubated for 4 mM at 37° C. Clotting was initiated by 50 µL of 25 mM $CaCl_2$ solution (Baxter, Austria) and recorded for up to 5 minutes. All pipetting steps and clotting time measurements were carried out with an ACL Pro Elite (Instrumentation Laboratory, Bedford, Mass.) instrument. Samples were run in duplicate. The aPTT was plotted against the NASP concentration and the concentration at which a 50% increase in clotting time over baseline was observed was reported.

Dilute Prothrombin Time (dPT) Assay

One dPT assay for use herein is a modified standard clinical PT assay. Details methods for the dPT assay can be found in Nordfang et al. (1991) Thromb Haemost 66:464-467; Welsch et al. (1991) Thrombosis Research 64: 213-222, which are herein incorporated by reference. A dilute prothrombin time assay with added tissue factor pathway inhibitor (TFPI-dPT) may be used to demonstrate the TFPI-inhibiting effect of fucoidan BAX513 in hemophilic patient plasma (George King Biomedical). Plasma samples are pre-incubated with 0.3 µg/mL full-length TFPI (aa 1-276, constitutively produced by SKHep1) and BAX513 (0.03-1 µg/mL) for 15 min at RT. TF reagent TriniClot PT Excel S (Trinity Biotech), diluted in Hepes-buffered saline 1:400 with 0.5% BSA is added to the plasma samples on an ACL Pro Elite hemostasis analyzer (Instrumentation Laboratory). Clotting is initiated with 25 mM $CaCl_2$. The volume ratio of plasma:TF:$CaCl_2$ was 1:1:1. The time for plasma clotting is measured with a ACL ProElite Hemostasis Analyzer. For data analysis, TFPI-dPT is plotted against the log concentration. Half maximal effective concentrations ($EC_{50}$) values are determined using a sigmoidal curve fit.

Surface Plasmon Resonance Interaction Studies

Surface plasmon resonance experiments (Biacore T200, GE Healthcare) were performed to study the interaction of selected fucoidans with human full-length TFPI (aa 1-276) and a truncated TFPI1-160 protein. fl-TFPI (full-length TFPI) was covalently coupled to a CM5 chip (GE Healthcare) using amine coupling chemistry at pH 5.0 (10 mM sodium acetate) resulting in immobilization of 1000 response units (RU) for fl-TFPI. For the kinetic analysis the surfaces were equilibrated at a flow rate of 30 µL/minute with HBS-N buffer (0.01 M HEPES, pH 7.4; 0.15 M NaCl, GE Healthcare) to which 0.1% Tween-80 (Merck) was added. After 60 seconds, fucoidan samples (0.1-50 µg/mL) dissolved in equilibration buffer were injected for 360 seconds followed by a dissociation time of 600 s. The chip was regenerated by injecting 22.5 µL of 2.5 M NaCl followed by 15 µL of 10 mM NaOH, 1 M NaCl. The flow rate was kept at 30 µL/min Each sensorgram was referenced against buffer and the blank cell. The evaluation was done in Biacore T200 Evaluation Software. The procedure for fucoidan/$TFPI_{1-160}$ binding was carried out in the same manner.

Molecular Structure

Charge-Fractionation

F.v. fucoidan was fractionated by a GE Healthcare LC system, ÄKTA Purifier 100 with a DEAE (diethylaminoethyl) Sepharose F. F. column (5×22 cm, column volume, 431 mL). Solvent A and B were Milli-Q water and 2 M NaCl. A linear gradient was applied for 16 column volumes at a 49 mL/min flow rate. The collected eluate was quantified for carbohydrate content offline with a phenol-sulfuric acid assay.

Size-Fractionation.

F.v. fucoidan was fractionated using ultra-filtration with different cut-off size membranes. Fractions with different Mw ranges were obtained and analyzed.

Phenol-Sulfuric Acid Assay

Phenol-sulfuric acid assays were carried out in a glass tube. To 200 µL (small scale)/300 µL (large scale) eluate, 100 µL 5% (w/v) aqueous phenol was added followed by 1 mL of concentrated sulfuric acid. The reactions incubated at 100° C. in an oven for 10 minutes. After the reacted solutions were cooled down to room temperature, they were transferred to a 96 well plate (200 µL in each cell) and absorbance was measured at 490 nm with a plate reader. The chromatograms were generated by plotting the absorbance as function of retention time or tube number.

Agarose Gel Analysis

Fucoidans were analyzed by agarose gel electrophoresis. A Bio-Rad Mini-Sub cell was used to cast the gel. Samples (10-20 µg of each) were applied to a 0.5% agarose gel in 0.04 M barium acetate buffer (pH5.3) and run for 2 h at 100 mA in 0.05 M 1,3-diaminopropane-acetate (pH adjusted to 9.0 with acetic acid). The gel was stained in Alcian Blue aqueous solution for 30 minutes and destained in Milli-Q water overnight to clean the background.

Average Molecular Weight (Mw) and Polydispersity (polyD) Determination Using Size-Exclusion Chromatography and Multi-Angle Laser Light Scattering (SEC-MALLS)

An Agilent HPLC System coupled with Wyatt Technology DAWN HELEOS, QELS (Quasi-Elastic Light Scattering) and Optilab rEX differential refractive index (dRI) detectors was used to measure the molecular weight and polydispersities of different fucoidans. Each fucoidan (about 5 mg of solid) was dissolved in 250 µL of PBS mobile phase, and 50 µL was injected on a column, Superdex 200 (10 mm/300 mm, GE Healthcare, Piscataway, N.J.). The change in refractive index/change in concentration (dn/dc) value (0.113 mL/g) was determined on a sample of F.v. fucoidan. This value was used to calculate the molecular weight of all NASP samples.

Monosaccharide Analysis Using High-Performance Anion Exchange with Pulsed Amperometric Detection (HPAE-PAD)

Each sample was hydrolyzed to monosaccharides using 2 M trifluoroacetic acid (TFA) in a concentration of 2 mg/mL at 100° C. for 5 h. The excess TFA in each sample was removed by drying the sample in a vacuum centrifuge and the hydrolysates were dried using a SpeedVac concentrator. The dried hydrosylate was re-dissolved in the same volume of water and pH was adjusted to neutral with diluted NaOH after it was re-dissolved in the same volume of water.

A Dionex ICS 3000 system (Dionex, Sunnyvale, Calif.) equipped with pulsed amperometric detector, Dionex guard column CarboPac® PA10 (2×50 mm), and Dionex analytical column CarboPac® PA1 (4×250 mm), was used to analyze their monosaccharide compositions. An isocratic gradient of 15 mM NaOH (0-10 minutes) was performed at 1 mL/min to first separate neutral sugars, followed by a NaOAc gradient (0-200 mM) with fixed 15 mM NaOH (10-40 minutes) to separate acidic sugars. The injection volume was about 25 µL. The column temperature was 30° C. The waveform of the PAD was the Dionex default program for carbohydrates. The HPAE-PAD system was controlled by Chromeleon software (version 6.80). Seven monosaccharides were used as standards: glucose, galactose, mannose, arabinose, rhamnose, xylose and fucose (Sigma, St. Louis, Mo.).

Nuclear Magnetic Resonance (NMR) Spectroscopy

A Bruker Avance III NMR spectrometer operating at a $^1H$ frequency of 600 MHz with a dual $^1H/^{13}C$-cryoprobe was used to acquire quantitative $^{13}C$-NMR spectra. About 20 mg of each fucoidan were dissolved in 0.6 mL $D_2O$ with 0.02% deuterium sodium-3-trimethylsilylprionate (TMSP) (Cambridge Isotope Lab., Andover, Mass.) and transferred to NMR tubes. The relaxation delay for $^{13}C$ NMR was optimized to obtain quantitative data. $^{13}C$-NMR spectra with relaxation delays of 1 s, 2 s, 5 s, 10 s, 30 s and 60 s, were acquired on sample L.j. fucoidan, to determine a suitable delay time for full relaxation of the carbonyl groups. To prevent nuclear Overhauser enhancement (NOE) of all signals in the $^{13}C$-NMR spectra, the decoupler was gated on only during the data acquisition time. Recycle delays of 5 s and an acquisition time of 0.1 s were used for full relaxation of the carbonyl groups and to prevent NOE enhancement of all signals in the $^{13}C$-NMR spectra. The spectra were processed using Topspin 2.1 software (Bruker, Germany).

About 20 mg of each NASP was dissolved in 0.6 mL $D_2O$ with 0.02% deuterium sodium-3-trimethylsilylprionate (TMSP) (Cambridge Isotope Lab., Andover, Mass.) as a chemical shift reference. One-dimensional $^1H$-NMR $^{13}C$ NMR spectra, two-dimensional (2D) $^1H$-$^1H$ Correlation Spectroscopy (COSY), $^1H$-$^{13}C$ phase sensitive multiplicity edited Heteronuclear Single Quantum Correlation (HSQC), $^1H$-$^{13}C$ magnitude mode Heteronuclear Multiple Bond Correlation (HMBC), and 3D HSQC-TOCSY spectra were acquired and processed using Topspin 3.0 software (Bruker Biospin Corporation, Billerica, Mass.).

Oversulfation of NASPs

Oversulfation reactions were carried out on a fucoidan having a Mw of about 50 kDa. Fucoidan (0.2 g) was stirred in 4 mL of DMF and 6 mL of pyridine at 90° C. for 30 min Different amounts (1.4 and 0.4 g) of sulfation reagent (sulfur trioxide-pyridine complex) were added in order to produce fucoidans with two levels of oversulfation. For each preparation, corresponding to the higher and lower degrees of oversulfation, the mixture was stirred at 90° C. for 2 hours, cooled to room temperature, and filtered to get a white solid. This solid was dissolved in 10 mL of saturated $NaHCO_3$ solution. The dried solid was desalted and lyophilized.

Desulfation of NASPs

A mixture of DMSO (45 mL) and toluene (15 mL) was refluxed under Dean Stark conditions until 15 mL of solution was removed. The solution was cooled to 120° C. and 1.0 g of fucoidan was added. After 5 min, 2.5 mL of pyridine, 0.75 g of pyromellitic acid and 0.5 g of NaF were added. Then, 5 mL of additional pyridine was added. The reaction was carried out at 120° C. under argon. To obtain different degrees of desulfation, two aliquots were taken out from the mixture at 1 and 2 hours. When the aliquots were cooled to room temperature, 40 mL of EtOAc was added to each aliquot and was kept at 5-8° C. for 2 hours. Each aliquot was filtered and the yielded white solid was washed with EtOAc (5 mL). The white solid was dissolved in deionized water (10 mL) and was added to 1.5 mL of saturated $NaHCO_3$. The solution was desalted and lyophilized to yield the final desulfated fucoidan.

Chemical Makeup

Elemental Analysis

Inductively Coupled Plasma (ICP) analyses

A combination of ICP-mass spectrometry (MS) and ICP-atomic emission spectroscopy (AES) analyses were performed to obtain the elemental profile for the different fucoidans. The ICP-MS analyses were performed using a Thermo Scientific X-Series 2 ICP-MS 2 configured with microflow PFA-ST nebulizer and glass impact bead spray chamber. The instrument was operated with and without the collision cell (7% hydrogen/helium collision cell gas). Scandium and indium were used as internal standards for the ICP-MS analyses. The ICP-AES analyses were performed using a Varian Radial ICP-AES system. The test solution for ICP-AES was mixed in line with a solution containing 2 ppm yttrium as the internal standard and 2% cesium chloride as an ionization suppressant. The instruments were standardized using NIST traceable Stock Standard Solutions (High Purity Standards, Inc and Inorganic Ventures).

The samples were prepared at 0.5% (w/v, 0.1 g sample in 20 mL solution) in 5% aqua regia ($HCl/HNO_3$) for analyses. Representative test samples were supplemented with the target elements. The analytical recovery of each element was calculated and compared to an acceptance criterion of 100±30%. The lowest quantity determinable (LQD) was established as ten times the standard deviation of the blank response for each element. The lowest qualified standard response was used as the reporting limit for each element.

Additional C, N, H, and S Analysis

The PE 2400 CHN Analyzer was used for C, H, and N measurements. Sulfur was analyzed by colorimetric titration.

Example 1

Coagulation Activity

Figure 2:
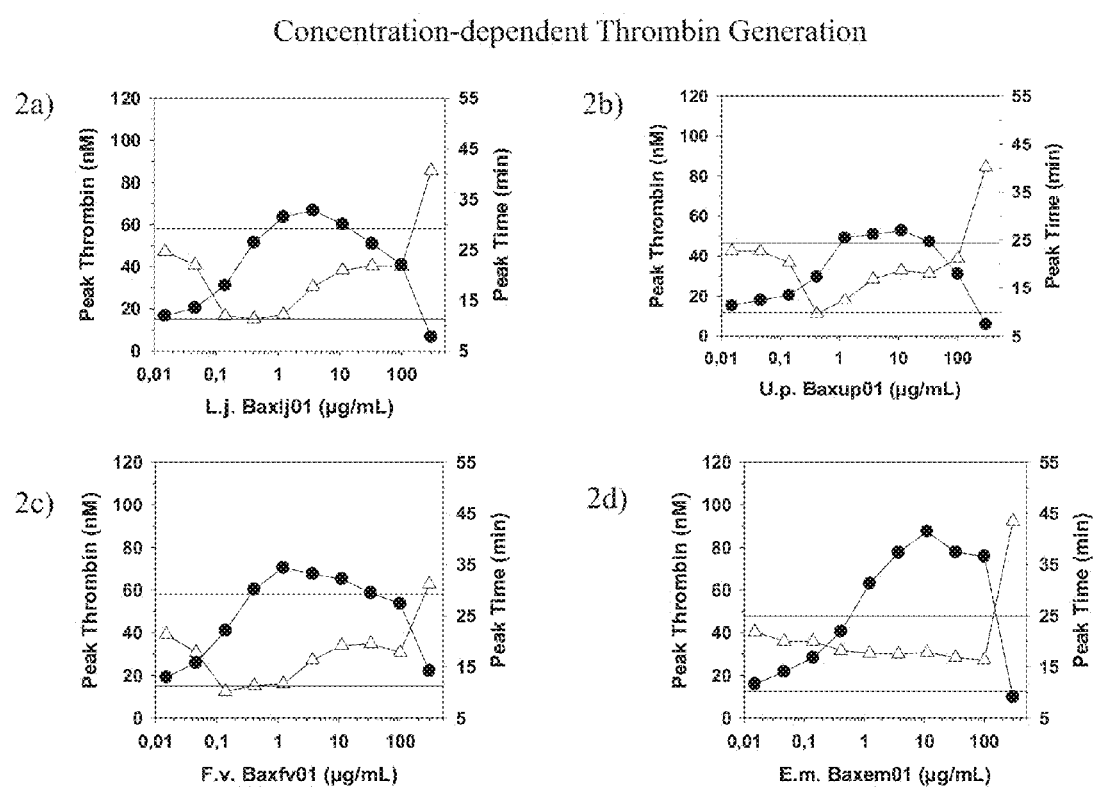
FIGS. 2a-d show examples of data acquired for the procoagulant activity of NASP compositions as measured using calibrated automated thrombography (CAT).
Figure 3:
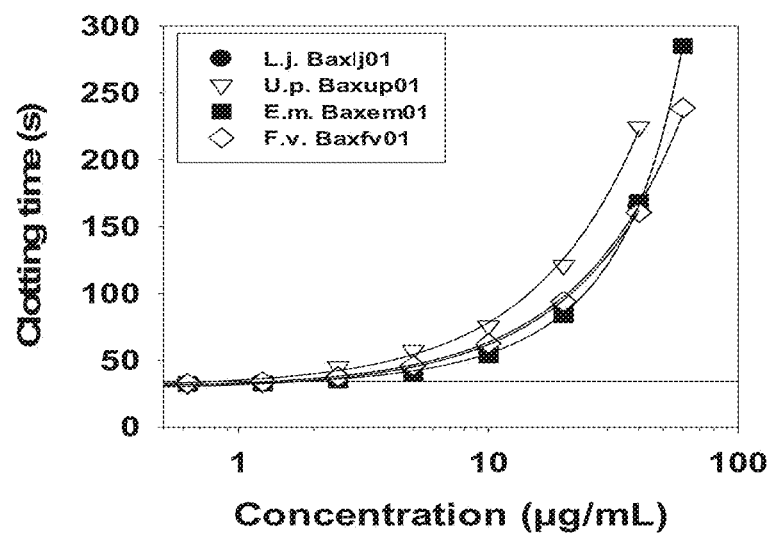
FIG. 3 shows an example of anticoagulant activity data of NASP compositions as measured using the Activated Partial ThromboplastinTime (aPTT) Assay.

Biological activity was tested using fucoidan candidates to determine suitable candidates for the development of a new treatment for subjects with blood coagulation disorders. Fucoidans exhibit procoagulant activity by inhibiting TFPI and by accelerating thrombin-dependent FVa formation. The fucoidans tested exhibited inhibition of full-length TFPI. Fucoidans also demonstrated some anticoagulant activity. Potentiation of the thrombin inhibitors antithrombin III and/or heparin cofactor II have been described as one anticoagulant mechanism. Contact system activation and subsequent generation of bradykinin, was also observed in some fucoidans. The procoagulant window of the fucoidans tested were within the concentration range of four magnitudes (~0.1-100 µg/mL, as depicted in FIG. 2). Furthermore, these fucoidans increase thrombin generation in normal plasma, demonstrating procoagulant activity independent of hemophilic factors. In order to select the NASP candidate with the highest quality, all of the procoagulant and anticoagulant activities were evaluated and compared. Two candidates, L.j. and F.v. fucoidan exhibited high procoagulant and low anticoagulant activity (FIGS. 2 and 3 and Table 7); E.m. fucoidan has a procoagulant activity differing from the other three fucoidans with thrombin generation improvement up to two-fold over the normal level 1; U.p. fucoidan has a higher anticoagulant activity. L.j. and E.m. fucoidans activate the contact pathway at concentrations >5 µg/mL (see FIGS. 4a-j). U.p. and F.v. fucoidan did not activate the contact pathway up to a concentration 30-fold higher than their procoagulant optima.

Procoagulant Activity

Several fucoidans tested showed improvement in clotting parameters via the extrinsic pathway of coagulation by inhibiting TFPI. In order to identify whether a fucoidan may be suitable for treating a subject having a blood coagulation disorder, fucoidans from four different species: L.j., U.p., E.m. and F.v. (FIG. 1) were screened for their procoagulant and anticoagulant activities. First, their pro- and anticoagulant activities in FVIII-inhibited plasma were assessed using calibrated automated thrombography (CAT). The concentration-dependent thrombin generation of the fucoidan candidates is shown in FIG. 2. All of the fucoidans tested were able to correct coagulation of hemophilic plasma to normal levels at about 1 µg/mL. Although the procoagulant activity declines at concentrations higher than 10 µg/mL, it still outweighs the anticoagulant effects. A fucoidan extracted from E.m. reached a thrombin generation level of twofold of the normal plasma level. Half-maximum levels ($EC_{50}$ values in Table 7) ranged from 0.2-0.8 µg/mL depending on the biological source (i.e., algae species). All NASPs were equally able to improve clotting parameters of FVIII-inhibited whole blood as was demonstrated by Rotation Thromboelastometry (ROTEM) analysis (data not shown).

FIGS. 2a-2d show the effects of fucoidans from four different brown algae species on thrombin generation. Clotting of human plasma was triggered by 1 µM of tissue factor in the CAT assay in the presence of 0-300 µg/mL fucoidan. FIG. 2a shows thrombin generation profiles of L.j. fucoidan; FIG. 2b is U.p. fucoidan; FIG. 2c is E.m. fucoidan and FIG. 2d is F.v. fucoidan. Thrombin peaks (nM, black circles) and peak time (min, white triangles) are shown. All fucoidans had a concentration-dependent effect on thrombin generation and were able to correct coagulation of FVIII-inhibited plasma (lower black line) to normal levels (upper black line) at around ~1 µg/mL.

In order to identify whether NASPs having certain charge densities and degree of sulfation characteristics may be suitable for treating a subject having a blood coagulation disorder, NASPs obtained by charge fractionation of F.v. fucoidan samples using DEAE ion exchange chromatography were screened for their procoagulant activity. Procoagulant activity for fractions C2-C6 were determined using assay conditions described above. In the CAT assay, fractions C2-C6 showed a procoagulant effect between about 0.05 and 10 µg/mL, and the $EC_{50}$ for the procoagulant activity for fractions C2-C6 were about 0.2 µg/mL. Table 1 summarizes the procoagulant activity of NASPs obtained by charge fractionation of F.v. fucoidan samples.

TABLE 1

Degree of sulfation and procoagulant activity of NASPs from charge separated fractions of F.v. fucoidan

| Fractions | Degree of Sulfation | CAT $EC_{50}$ (µg/mL) |
|---|---|---|
| C1 | 0.28 | 1.3 ± 0.48 |
| C2 | 0.49 | 0.2 ± 0.02 |
| C3 | 0.72 | 0.2 ± 0.04 |
| C4 | 0.72 | 0.2 ± 0.08 |
| C5 | 0.8 | 0.2 ± 0.01 |
| C6 | 0.8 | 0.2 ± 0.09 |
| F.v. Fucoidan | 0.6 | 0.1 ± 0.04 |

Figure 5:
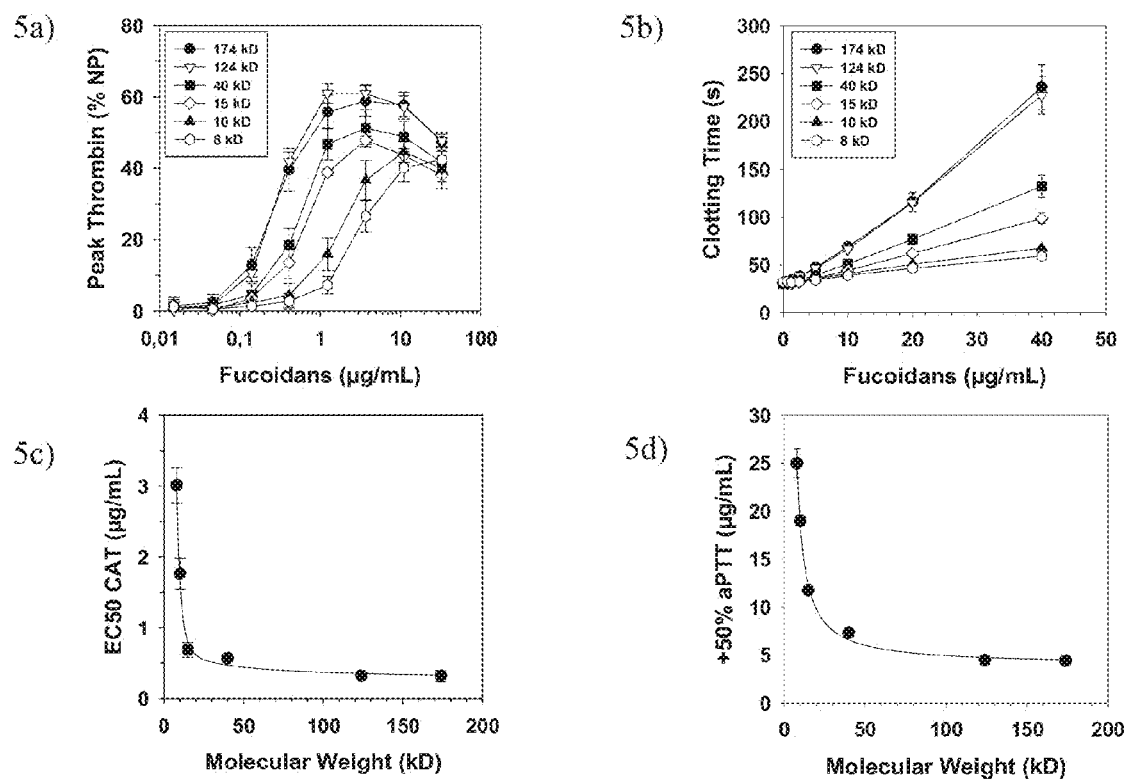
FIGS. 5a-d show procoagulant and anticoagulant activities of size-separated NASP compositions.

In order to identify whether NASPs having certain molecular weights and degree of polymerization may be suitable for treating a subject having a blood coagulation disorder, NASPs obtained by size-separated fractionation of F.v. fucoidan samples using ultrafiltration were screened for their procoagulant activity. The CAT results are shown in FIG. 5a and summarized in Table 2. The molecular weight-procoagulant activity relationship of NASPs is shown in FIG. 5c. The procoagulant activity was determined to be related to molecular weight. In this example, a molecular weight of equal to or greater than 15 kDa showed high activity, whereas, the procoagulant activity of NASPs having a molecular weight of below 15 kDa were significantly lower. The degree of polymerization was calculated from the Mw and degree of sulfation. In this example, a degree of polymerization of at least 70 showed high activity, whereas the procoagulant activity of NASPs having a degree of polymerization below about 70 were significantly lower.

TABLE 2

Molecular weight, degree of polymerization and procoagulant activity of size separated fractions of F.v. fucoidan

| Fraction Number | Molecular Weight (kDa) | Degree of Polymerization | CAT $EC_{50}$ (µg/mL) |
|---|---|---|---|
| S1 | 174 | 840 | 0.3 ± 0.07 |
| S2 | 124 | 590 | 0.3 ± 0.02 |
| S3 | 40 | 200 | 0.6 ± 0.06 |
| S4 | 15 | 70 | 0.7 ± 0.11 |
| S5 | 10 | 50 | 1.8 ± 0.22 |
| S6 | 8 | 40 | 3.0 ± 0.26 |

Figure 6:
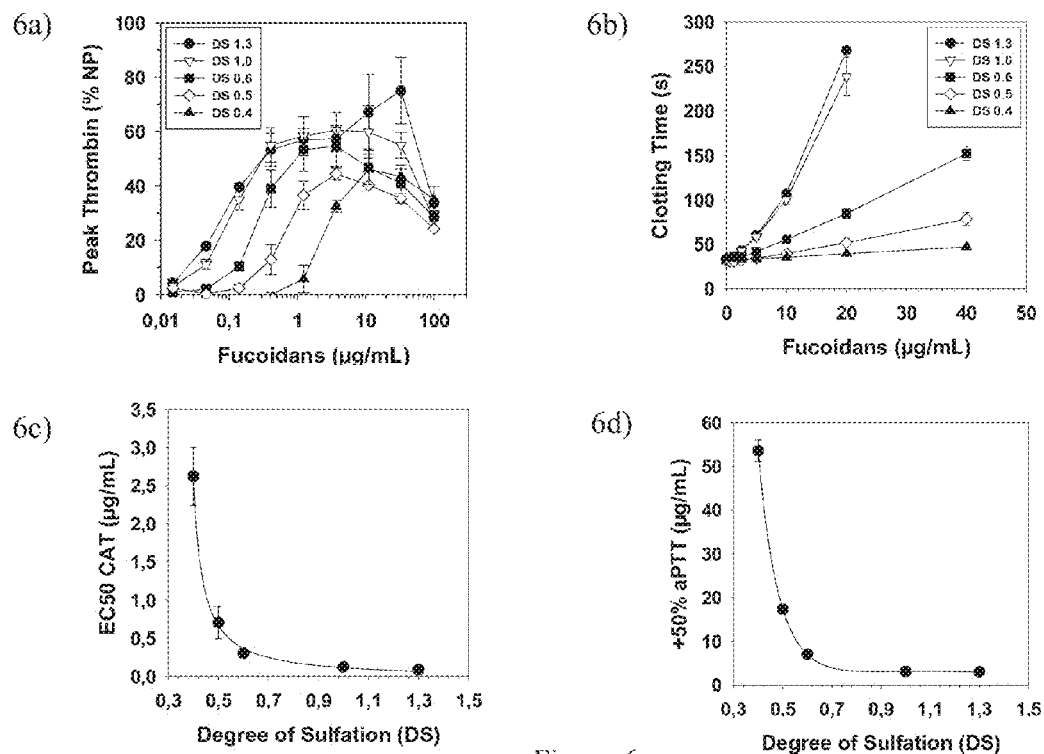
FIGS. 6a-d show procoagulant and anticoagulant activities of oversulfated and desulfated NASP compositions.

Desulfated and oversulfated F.v. fucoidans were also used to investigate the impact of charge density and degree of sulfation on procoagulant activity. In the CAT assay, the procoagulant activity of the chemically-sulfated fucoidans showed a rough dependence on charge density. As shown in Table 3 and FIGS. 6a and 6c, the procoagulant activity decreases as the degree of polymerization decreases from 1.3 to 0.4. The two oversulfated fucoidans showed procoagulant effect between 0.01 and 10 µg/mL, and the CAT $EC_{50}$ values were 0.09 and 0.12 µg/mL. Meanwhile the two desulfated fucoidans showed higher effective concentration range and $EC_{50}$ values indicating lower procoagulant activity than that of unmodified fucoidan. The procoagulant activity $EC_{50}$ was plotted as a function of degree of polymerization in FIG. 6c.

TABLE 3

Procoagulant activity of oversulfated and desulfated F.v. Fucoidan

| Sample | Degree of Sulfation | Molecular Weight (kDa) | Degree of Polymerization | CAT $EC_{50}$ (µg/mL) |
|---|---|---|---|---|
| Oversulfated Fucoidan 1 | 1.34 | 65 | 230 | 0.09 ± 0.01 |
| Oversulfated Fucoidan 2 | 1.03 | 55 | 220 | 0.12 ± 0.01 |
| Unmodified Fucoidan | 0.63 | 51 | 240 | 0.30 ± 0.01 |
| Desulfated Fucoidan 1 | 0.50 | 24 | 120 | 0.70 ± 0.21 |
| Desulfated Fucoidan 2 | 0.37 | 15 | 80 | 2.62 ± 0.38 |

Inhibition of Tissue Factor Pathway Inhibitor (TFPI)

Figure 7:
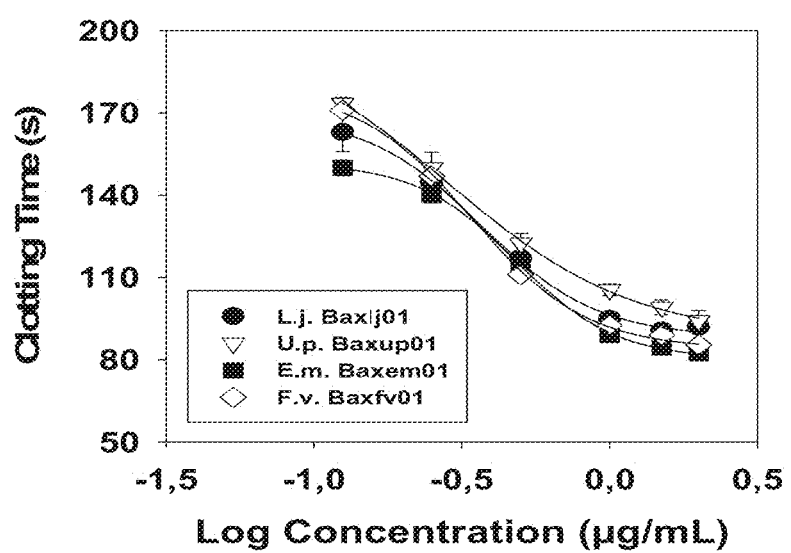
FIG. 7 shows an example of data for measuring inhibition of tissue factor pathway inhibitor (TFPI) by NASP compositions as measured by dilute prothrombin time assay (dPT) according to certain embodiments.

NASPs exhibited TFPI-neutralizing activity in mechanistic studies. Fucoidans were tested for TFPI-inhibiting activity using a TFPI dilute prothrombin time (TFPI-dPT) assay, CAT experiments and surface plasmon resonance (Biacore) studies. The tested fucoidans showed similar effects on full-length TFPI added to normal human plasma. They reversed the TFPI-induced prolonged clotting time with half-maximum concentrations of about 0.4 µg/mL (FIG. 7). In addition, fucoidans had no procoagulant effect in TFPI-depleted plasma CATs. This supports the TFPI-inhibiting mechanism of fucoidans. Interaction of NASPs with full-length TFPI was also confirmed by surface plasmon resonance binding experiments.

FIG. 7 shows a dilute prothrombin time assay where added tissue factor pathway inhibitor (TFPI-dPT) was used to evaluate the TFPI-inhibiting effect of different fucoidans. Pooled normal human plasma was pre-incubated with 0.5 µg/mL full-length TFPI (aa1-276) and the respective fucoidan (0.03-1 µg/mL) for 15 min at room temperature. Each of the fucoidan that were tested showed TFPI-inhibiting activities with an $EC_{50}$ of ~0.4 µg/mL.

Figure 19:
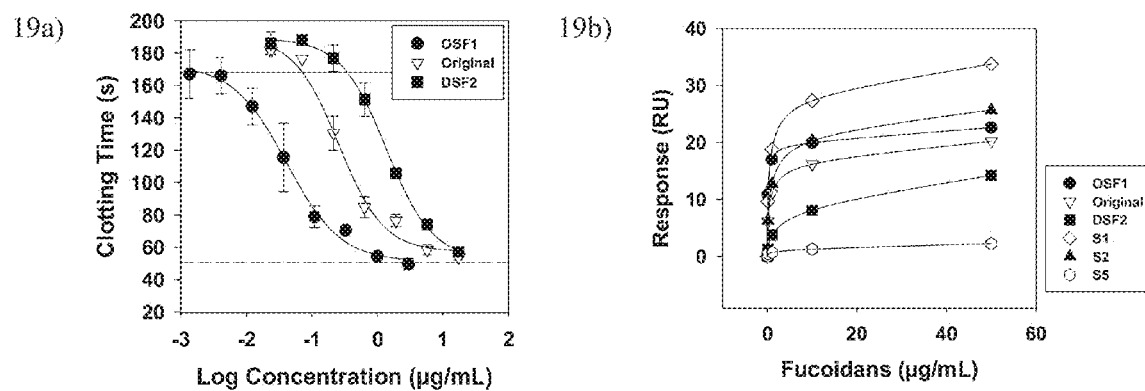
FIG. 19 shows an example of TFPI-dPT assay and Biacore experiments used to analyze the inhibition of TFPI anticoagulant effect and binding of NASPs to TFPI.

The inhibition of TFPI by NASPs obtained by charge fractionation of F.v. fucoidan samples using DEAE ion exchange chromatography and size fractionation by ultrafiltration were assessed with a dilute prothrombin time assay (dPT) with added full-length TFPI. All NASPs were able to reverse the anticoagulant effect of this coagulation inhibitor. Similar to the CAT experiments, the fucoidan's activity in the TFPI-dPT assay increased with higher degree of sulfation. $EC_{50}$ values of TFPI inhibition corresponded well to the ones determined by thrombin generation assays suggesting that blocking of TFPI is the mechanism of the procoagulant action of NASPs. The TFPI-blocking activity was determined to be dependent on the degree of sulfation of the NASPs. Interaction of selected NASPs with TFPI was confirmed by surface plasmon resonance studies (FIG. 19). All NASPs bound to full-length TFPI but not a C-terminally truncated form $TFPI_{1-160}$. This indicates that the molecular weight and degree of sulfation are related to the procoagulant activity of the NASPs. Size fractionation fraction S5 with a size of 10 kDa did not substantially interact with TFPI indicating that a molecular weight threshold of about 15 kDa may be suitable for sufficient inhibition of TFPI.

The inhibition of TFPI anticoagulant effect and binding of fucoidans to TFPI is depicted in FIGS. 19a and 19b Inhibition of TFPI by fucoidans was analyzed in a modified dPT assay where fl-TFPI was added (FIG. 19a). Fucoidans reverse the anticoagulant effect of TFPI in a dose dependent manner Inhibition of TFPI was increased or decreased by oversulfating or desulfating the fucoidan, respectively. Thus, inhibition of TFPI was shown to depend on charge density of the NASP. Interaction of fucoidans with fl-TFPI in Biacore experiments. (FIG. 19b) Fucoidans dose-dependently interact with TFPI. The response also increased with higher molecular weight and degree of sulfation.

Anticoagulant Activity

The NASPs tested exhibit anticoagulant activity at higher concentrations (>4 µg/mL) according to CAT and aPTT experiments. To measure their anticoagulant effect aPTT assays were performed and the concentration at which a 50% increase in the clotting time occurred compared to normal human plasma was determined. The data show that U.p. fucoidan had about twice the anticoagulant activity as L.j, F.v. and E.m. fucoidans (FIG. 3 and Table 7). All fucoidans displayed increasing anticoagulant activities starting at about tenfold above the optimal procoagulant concentration. The ratio of the NASP's procoagulant and anticoagulant activities was calculated (Table 7). F.v. and L.j. fucoidan showed good procoagulant activity and little anticoagulant effect.

FIG. 3 shows the anticoagulant activity of several tested fucoidans. The anticoagulant effect of fucoidans at concentrations of 0-60 µg/mL was assessed by the activated partial thromboblastin time assay in normal human plasma. Concentration-dependent increase in clotting time for four representative candidates are shown. U.p. fucoidan (white triangles) showed higher anticoagulant activity than the other fucoidans.

In order to identify whether NASPs having certain charge densities and degree of sulfation characteristics may be suitable for treating a subject having a blood coagulation disorder, NASPs obtained by charge fractionation of F.v. fucoidan samples using DEAE ion exchange chromatography were screened for their anticoagulant activity. Anticoagulant activity for fractions C1-C6 were determined using assay conditions described above. The concentrations at which a 50% increase in the clotting time occurred compared to normal human plasma were determined by the aPTT assay and are summarized in Table 4. All of the NASPs obtained by charge-separated fractionation exhibited anticoagulant activity at higher concentrations (>5 µg/mL) according the aPTT experiments.

TABLE 4

Degree of sulfation and anticoagulant activity of charge-separated fractions of F.v. fucoidan

| Fractions | Degree of Sulfation | aPTT +50% concentration (µg/mL) |
|---|---|---|
| C1 | 0.28 | 24.7 ± 0 |
| C2 | 0.49 | 7.5 ± 0.42 |
| C3 | 0.72 | 5.9 ± 0.35 |
| C4 | 0.72 | 6.9 ± 1.45 |
| C5 | 0.8 | 6.1 ± 0.64 |
| C6 | 0.8 | 6.1 ± 0.55 |
| F.v. Fucoidan | 0.6 | 4.0 ± 0.28 |

In order to identify whether NASPs having certain molecular weights and degree of polymerization may be suitable for treating a subject having a blood coagulation disorder, NASPs obtained by size-separated fractionation of F.v. fucoidan samples using ultrafiltration were screened for their anticoagulant activity. The aPTT results are shown in FIGS. 5B and 5D and summarized in Table 5. The anticoagulant activity was determined to be related to molecular weight. In this example, a molecular weight of equal to or greater than 41 kDa showed high anticoagulant activity, increasing clotting time by 50% at 5 µg/mL whereas, the NASPs having a molecular weight of below 41 kDa were require higher concentration. The degree of polymerization was also similarly investigated. In this example, a degree of polymerization of equal to or greater 200 showed high anticoagulant activity, whereas the anticoagulant activity of NASPs having a degree of polymerization below about 200 were significantly lower.

TABLE 5

Molecular weight, degree of polymerization and anticoagulant activity of size-separated fractions of F.v. fucoidan

| Fraction Number | Molecular Weight (kDa) | Degree of Polymerization | aPTT +50% conc. (µg/mL) |
|---|---|---|---|
| S1 | 174 | 840 | 4.4 ± 0.14 |
| S2 | 124 | 590 | 4.5 ± 0.14 |
| S3 | 40 | 200 | 7.3 ± 0.49 |
| S4 | 15 | 70 | 11.6 ± 0.14 |
| S5 | 10 | 50 | 18.8 ± 0.64 |
| S6 | 8 | 40 | 23.6 ± 3.54 |

Desulfated and oversulfated F.v. fucoidans were also used to investigate the impact of charge density and degree of sulfation on anticoagulant activity. The two oversulfated fucoidans increased the clotting time to 50% above normal at much lower concentrations in an aPTT assay than the two desulfated fucoidans (Table 6). Thus, anticoagulant activity follows the same trend as seen with the procoagulant activity.

TABLE 6

Anticoagulant activity of oversulfated and desulfated F.v. Fucoidan

| Sample | Degree of Sulfation | Molecular Weight (kDa) | Degree of Polymerization | aPTT +50% conc. (µg/mL) |
|---|---|---|---|---|
| Oversulfated Fucoidan 1 | 1.34 | 65 | 230 | 2.9 ± 0.02 |
| Oversulfated Fucoidan 2 | 1.03 | 55 | 220 | 3.0 ± 0.23 |

TABLE 6-continued

Anticoagulant activity of oversulfated and desulfated F.v. Fucoidan

| Sample | Degree of Sulfation | Molecular Weight (kDa) | Degree of Polymerization | aPTT +50% conc. (µg/mL) |
|---|---|---|---|---|
| Unmodified Fucoidan | 0.63 | 51 | 240 | 7.0 ± 0.57 |
| Desulfated Fucoidan 1 | 0.50 | 24 | 120 | 17.3 ± 0.25 |
| Desulfated Fucoidan 2 | 0.37 | 15 | 80 | 53.6 ± 2.74 |

Contact Pathway Activation

Figure 4:
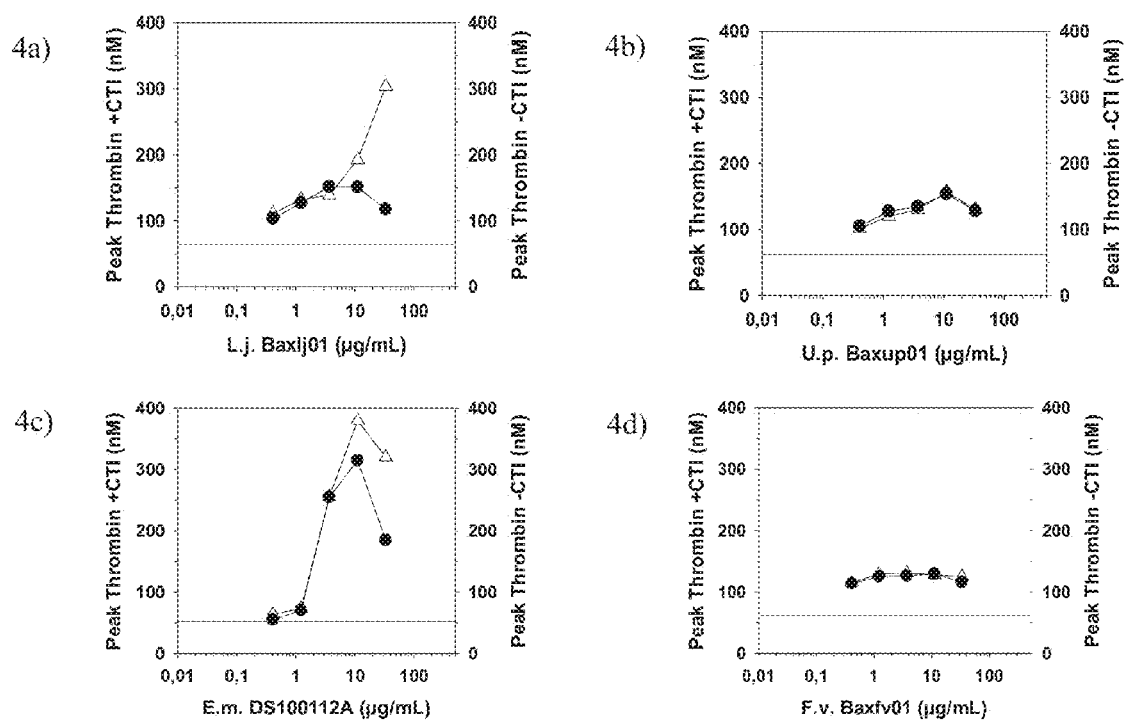
FIGS. 4a-j show examples of data for contact pathway activation of NASP compositions as measured using CAT in the presence and absence of corn trypsin inhibitor (CTI).
Figure 4:
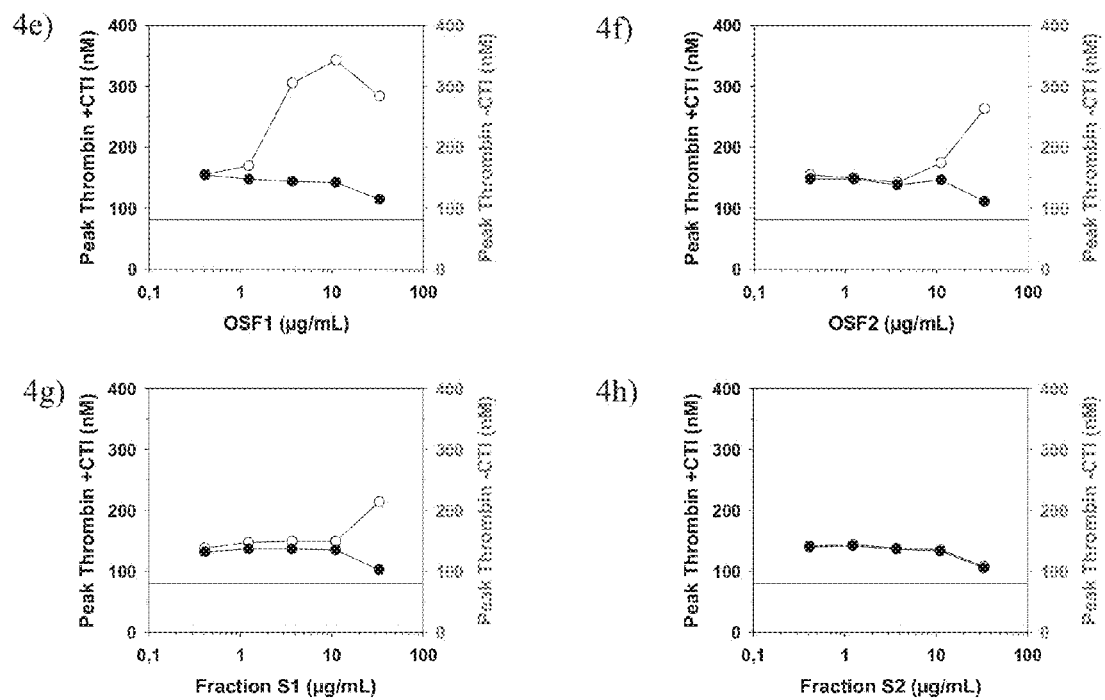
Figure 4:
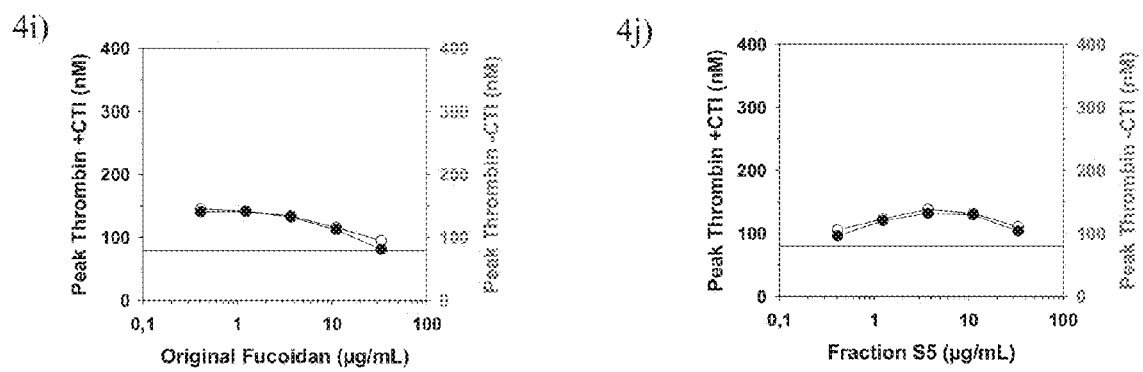

Many anionic polymers, such as sulfated glycosaminoglycans and polyphosphates are known to activate coagulation via the intrinsic contact pathway However, contact pathway activation is detrimental to treating a blood coagulation disorder because of its association with inflammation. Fucoidans were tested for their activation of the contact pathway. Addition of CTI (corn trypsin inhibitor) blocks FXIIa and thus, blocks the contact pathway. Therefore, fucoidans were tested in thrombin generation assays using a normal human plasma pool in the presence and absence of CTI to determine contact activation. All four fucoidans improved thrombin generation indicating their FVIII independent mode of action. L.j. fucoidan showed a clear increase in thrombin generation in the absence of CTI compared to the plasma control with CTI at concentrations greater than 5 µg/mL. E.m. fucoidan had a slight effect at a higher concentration. On the contrary, U.p. and F.v. fucoidans did not activate the contact pathway up to a concentration 30-fold higher than their procoagulant optimum (FIG. 4).

FIGS. 4a-4j depict the activation of the contact pathway by the tested fucoidans as well as by oversulfated NASPs and NASP fractions S1, S2 and S5 from size-separated fractionation as described in greater detail below. The tissue-factor triggered CAT assay in normal human plasma was performed in the absence and presence (40 µg/mL) of the FXIIa inhibitor CTI. FIGS. 4a-j show thrombin generation profiles of L.j. fucoidan, U.p. fucoidan, E.m. fucoidan and F.v. fucoidan as well as oversulfated NASPs and NASP fractions S1, S2 and S5 from size-separated fractionation with and without FXIIa inhibitor CTI. All fucoidans showed procoagulant activity in normal plasma: Thrombin peaks (nM, black circles) and normal plasma control (black line). L.j. and E.m. fucoidans show an increased thrombin formation in absence of CTI at concentrations >5 µg/mL (white triangles). This indicates activation of the contact pathway.

TABLE 7

Activity of Fucoidan samples from four different species and three lots of fucoidans from F.v. brown algae

| | L.j. Fucoidan | U.p. Fucoidan | E.m. Fucoidan | F.v. Fucoidan Lot 1 | F.v. Fucoidan Lot 2 | F.v. Fucoidan Lot 3 |
|---|---|---|---|---|---|---|
| $EC_{50}$ (µg/mL) | 0.3 | 0.4 | 0.8 | 0.2 | 0.3 | 0.2 |
| aPTT (µg/mL) | 7 | 4.5 | 8.7 | 6.5 | 6.3 | 6.2 |
| Ratio aPTT/$EC_{50}$ | 23.3 | 11.3 | 10.9 | 32.5 | 21.0 | 31.0 |

It was found that oversulfation may stimulate an activation of the contact pathway. In absence of the FXIIa inhibitor CTI, highly oversulfated fucoidan induced an increased thrombin generation at concentrations as low as 1 µg/mL. Unmodified and desulfated fucoidan did not show this effect.

Based on results obtained from NASPs from size fractionated samples of F.v. fucoidan, the largest fucoidan with a Mw of 174 kD also slightly activated the contact pathway in the absence of CTI. However, contact activation did not occur up to a degree of polymerization 600.

Example 2

Molecular Structure

A comparison of molecular structure of the tested fucoidans was also conducted. Three lots of F.v. fucoidan were characterized for product consistency.

Agarose Gel

Figure 8:
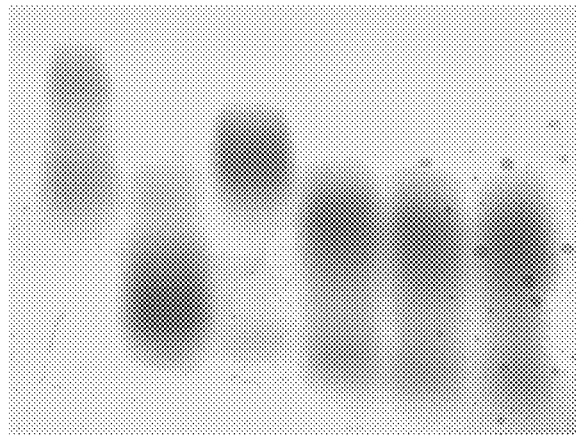
FIG. 8 shows an example of an agarose gel used to characterize NASP compositions according to certain embodiments.

Electrophoresis was used to compare fucoidans. In this work, agarose gels were applied to the tested fucoidans. (FIG. 8) The various species were distinguished by the migration of the fucoidans on the agarose gel, and the three lots appear similar on the gel, implying good lot-to-lot manufacturing reproducibility. The purity, molecular size-to-charge ratio, and affinity to barium are all properties that determine the migration of a sample in the gel. The gel for analysis of different fucoidans is shown in FIG. 8. The fucoidans from different sources were easily distinguished and the consistent performance of F.v. fucoidan lots on the gel was also confirmed.

Polyacrylamide Gel Electrophoresis (PAGE)

Different fucoidan lots were analyzed by polyacrylamide gel electrophoresis and their molecular weights could be roughly ranked.

Molecular Weight and Polydispersity Determination by Size Exclusion Chromatography-Multi-Angle Laser Light Scattering (SEC-MALLS)

The molecular weight and polydispersities of different fucoidans are listed in Table 8. The do/dc value specific to F.v. fucoidan (0.113 mL/g) was measured and used to calculate the average molecular weight of all fucoidans tested. From the SEC-MALLS data, F.v. fucoidans have an average molecular weight of about 130 to 160 kDa and L.j. fucoidans have similar average molecular weight of about 170 kDa. E.m. fucoidans have the largest molecular weight tested of more than 1,000 kDa; and the molecular weight of U.p. fucoidan is also large at greater than 500 kDa. Polydispersity, which is a reflection of size heterogeneity, is similar for all fucoidans in this report.

TABLE 8

Molecular weights (Mw) and polydispersities (PolyD) determined by SEC-MALLS

| | L.j. Fucoidan | U.p. Fucoidan | E.m. Fucoidan | F.v. Fucoidan Lot 1 | F.v. Fucoidan Lot 2 | F.v. Fucoidan Lot 3 |
|---|---|---|---|---|---|---|
| Average Mw. (kDa) | 170 | 620 | 1360 | 160 | 150 | 130 |
| PolyD | 1.8 | 1.6 | 1.5 | 1.6 | 1.7 | 1.7 |

Monosaccharide Analysis Using Ion Chromatography (IC)

Figure 9:
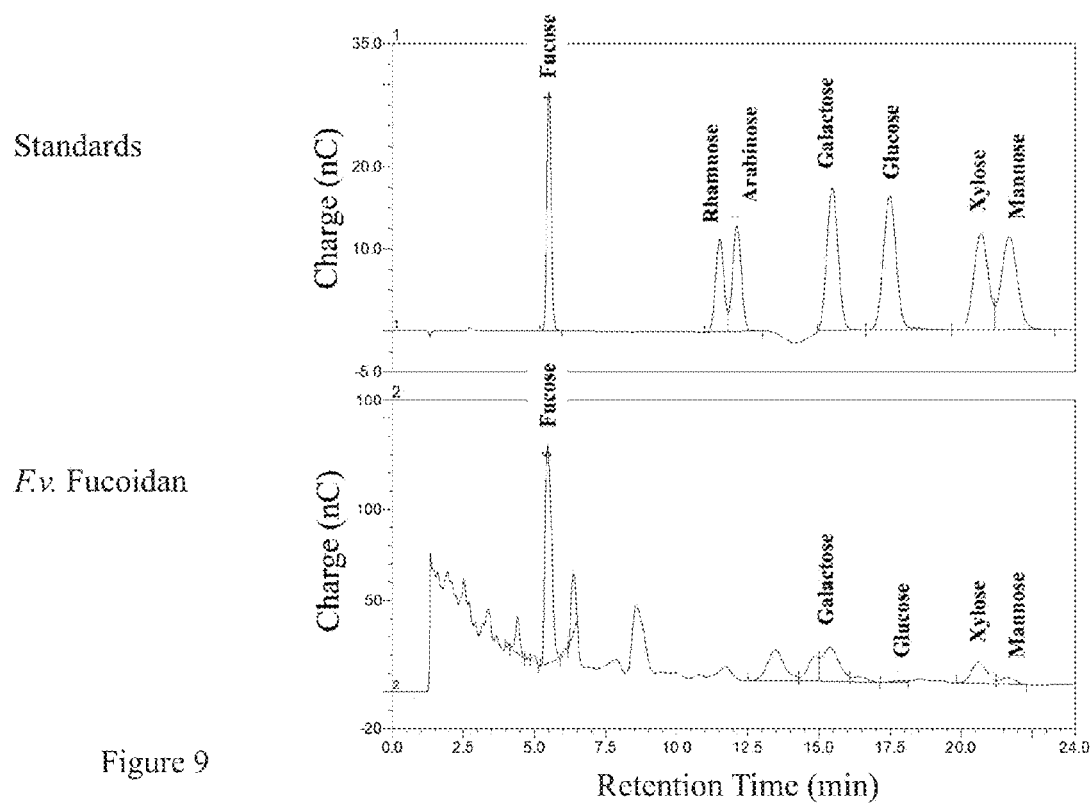
FIG. 9 shows an example of monosaccharide content for a NASP composition as measured by Ion Chromatography according to certain embodiments.

Fucoidan samples were hydrolyzed to monosaccharides. The hydrolysis was monitored by TLC. The separation of monosaccharide standards and one representative sample chromatogram are shown in FIG. 9. The monosaccharide composition results are listed in Table 9. Three components, fucose, galactose and xylose, were observed in L.j. fucoidan;

fucose and galactose were observed in U.p. and E.m. fucoidans. F.v. fucoidans contained almost entirely fucose.

TABLE 9

Monosaccharide composition determined by IC

| Relative Area (%) | L.j. Fucoidan | U.p. Fucoidan | E.m. Fucoidan | F.v. Fucoidan | | |
|---|---|---|---|---|---|---|
| | | | | Lot 1 | Lot 2 | Lot 3 |
| Fucose | 39 | 58 | 38 | 73 | 75 | 76 |
| Galactose | 35 | 37 | 41 | 15 | 15 | 14 |
| Glucose | 1 | 3 | 8 | 1 | 0 | 0 |
| Xylose | 21 | 1 | 5 | 9 | 8 | 8 |
| Mannose | 4 | 1 | 8 | 2 | 2 | 2 |

Fucose, Alginate and Heterogeneity Determinations Using $^{13}$C-NMR

The structure of the tested fucoidans were quantitatively characterized by $^{13}$C-NMR. This is the first time that a quantitative $^{13}$C-NMR approach was utilized as a method to evaluate fucoidans to identify whether one or more of the compositions may be suitable for treating a subject having a blood coagulation disorder.

Figure 11:
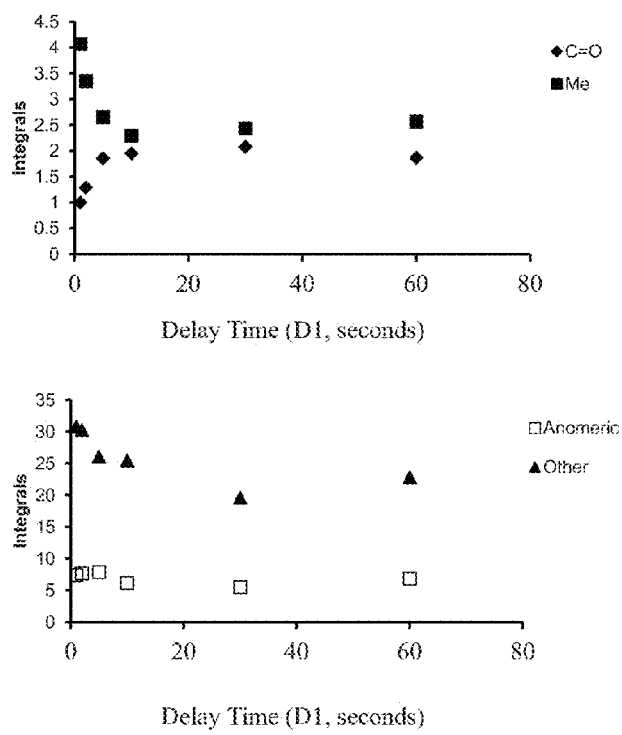
FIG. 11 shows an example of measuring integrals from the $^{13}$C-NMR plotted as a function of relaxation delay time (D1) for NASP compositions according to certain embodiments.

FIG. 11 depicts the integrals from the $^{13}$C-NMR plotted as a function of their relaxation delay time (D1). The pulse sequence employed was such that the decoupler was on only during an acquisition time. The relative integrals of the carbonyls increased when D1 was varied from 1 second to 5 seconds. The carbonyl groups were fully relaxed after a 5 second delay. The integrals of the methyl groups had a different response than those of the carbonyl groups. The integrals of methyl groups decreased when D1 was varied from 1 second to 5 seconds because the nuclear Overhauser enhancement was not completely removed until the D1 was longer than 5 seconds. The integrals for the other carbons on the sugar ring had similar behavior to that of the methyl groups, i.e., they decreased in intensity until a D1 of 5 seconds and were level at longer D1 values. The integrals for the anomeric carbons did not change significantly with D1. Based on these data, the minimum D1 for full relaxation of carbonyls is 5 seconds. All carbon NMR spectra of the fucoidan candidates were acquired with a 5 second delay time to obtain the quantitative data.

Figure 10:
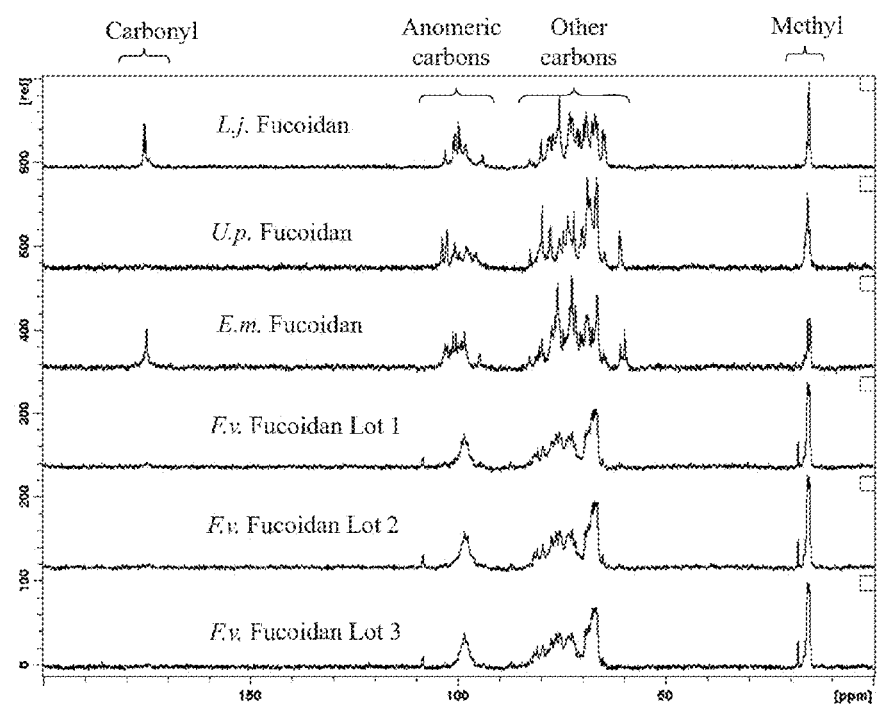
FIG. 10 shows an example of $^{13}$C-NMR used to characterize heterogeneity, fucose and alginate content of NASP compositions according to certain embodiments.

The $^{13}$C spectra were integrated over the ranges as shown in FIG. 10. Carbonyl groups from alginate were observed at δ 170-185 ppm, the anomeric peaks were observed at δ 88-112 ppm, the other carbons on the sugar ring were observed at δ 55-88 ppm, and the methyl group of fucose was observed at δ 9-20 ppm. The alginate content (% mol alginate/mol total polysaccharide) was calculated based on the fact that the alginate molecule contains one carbonyl per saccharide residue while each sugar residue, from any monosaccharide, has one anomeric carbon. Therefore:

$$C \%^{alginate} = \frac{\int carbonyls}{\int anomerics} \times 100\% \qquad \text{Eq. [1]}$$

where $\int carbonyls$ = integral of carbonyl groups;

$\int anomerics$ = integral of anomerics region.

Fucose content (% mol fucose/mol fucoidan) was calculated based on the fact that there is one methyl group per fucose residue while excluding of the contribution of the alginate impurity to the total polysaccharide. Therefore:

$$C \%^{fucose} = \frac{\int methyls}{\int anomerics - \int carbonyls} \times 100\% \qquad \text{Eq. [2]}$$

where $\int methyls$ = integral of methyl groups.

Some fucoidan samples had negligible alginate content (<10%) and, for those samples, equation 2 was simplified to:

$$C \%^{fucose} = \frac{\int methyls}{\int anomerics} \times 100\% \qquad \text{Eq. [3]}$$

The alginate and fucose contents are listed in Table 10. L.j. and E.m. fucoidans contained relatively high amounts of alginate, while U.p. and F.v. fucoidans only contained small amounts. F.v. fucoidan contained almost entirely fucose. L.j. and U.p. fucoidan contained 55-59% fucose, and E.m. fucoidan contained only 39% fucose. A comparison of fucose contents from IC and NMR (Table 9 and Table 10) were generally in agreement. Ion chromatography and NMR differ in that IC depends on hydrolysis of the polysaccharides to produce the monomers, while solution NMR observes the intact polysaccharides that are completely dissolved.

TABLE 10

Alginate and fucose content based on $^{13}$C-NMR analysis

| | L.j. Fucoidan | U.p. Fucoidan | E.m. Fucoidan | F.v. Fucoidan | | |
|---|---|---|---|---|---|---|
| | | | | Lot 1 | Lot 2 | Lot 3 |
| Alginate content (%)[a] | 28 | 2 | 25 | 7 | 6 | 5 |
| Fucose content (%) | 55[b] | 59[c] | 39[b] | 83[c] | 86[c] | 83[c] |

[a]calculated using Eq [1];
[b]calculated using Eq [2];
[c]calculated using Eq [3]

Charge Separated Fractionation to Determine Charge Density and Degree of Sulfation Fucoidan samples were fractionated using ion exchange chromatography as described above. Six fractions (C1-C6) were collected from the DEAE column. Both the charge density and the degree of sulfation were independently determined. The degree of sulfation was calculated from sulfur content measured by colorimetric titration.

The degree of sulfation of the eluted fractions was consistent with elution order, (Table 11) where the higher the degree of sulfation, the later the fraction was eluted. Monosaccharide analysis revealed that the sugar compositions of these fractions were also different from each other. Fraction C1 contains high levels of xylose (44%) and mannose (17%), relatively low levels of fucose (about 34%) and small amounts of other sugars. Fraction C2 contains increased fucose (about 60%), low xylose (about 18%) and mannose (about 7%) and has the highest galactose content (16%). Fractions C3-C6 have increasing fucose contents ranging from 78% to 94%, decreasing galactose content ranging from 14% to 6% and negligible amounts of xylose and mannose. However, unlike charge density, degree of sulfation and sugar composition, the average molecular of NASPs in fractions C2-C6 are similar ranging from about 100 to about 160 kDa, The avergage molecular weight of NASPs in fraction C1 was about 280 kDa.

TABLE 11

Degree of sulfation (DS), molecular weight and monosaccharide composition of F.v. fucoidan separated by charge

| Fractions | DS | Mw (kD) | Mol (%) | | | | | | |
|---|---|---|---|---|---|---|---|---|---|
| | | | Fucose | Rhanmose | Arabinose | Galactose | Glucose | Mannose | Xylose |
| C1 | 0.28 | 282 | 33.5 | 0.3 | 0.1 | 3.9 | 1.1 | 17.0 | 44.2 |
| C2 | 0.49 | 121 | 58.5 | 0.5 | 0.2 | 15.7 | 0.6 | 6.8 | 17.8 |
| C3 | 0.72 | 136 | 78.0 | 0.1 | 0.3 | 14.3 | N/A | 1.3 | 6.0 |
| C4 | 0.72 | 161 | 81.6 | 0.1 | 0.2 | 13.9 | N/A | 1.0 | 3.2 |
| C5 | 0.80 | 151 | 93.3 | 0.1 | N/A | 6.3 | 0.3 | N/A | N/A |
| C6 | 0.80 | 117 | 93.8 | N/A | N/A | 6.0 | 0.2 | N.A | N/A |
| Original fucoidan | 0.63 | 124 | 74.3 | 0.1 | 0.1 | 10.3 | 0.3 | 3.8 | 11.7 |

Size Separated Fractionation to Determine Size and Degree of Polymerization

Figure 12:
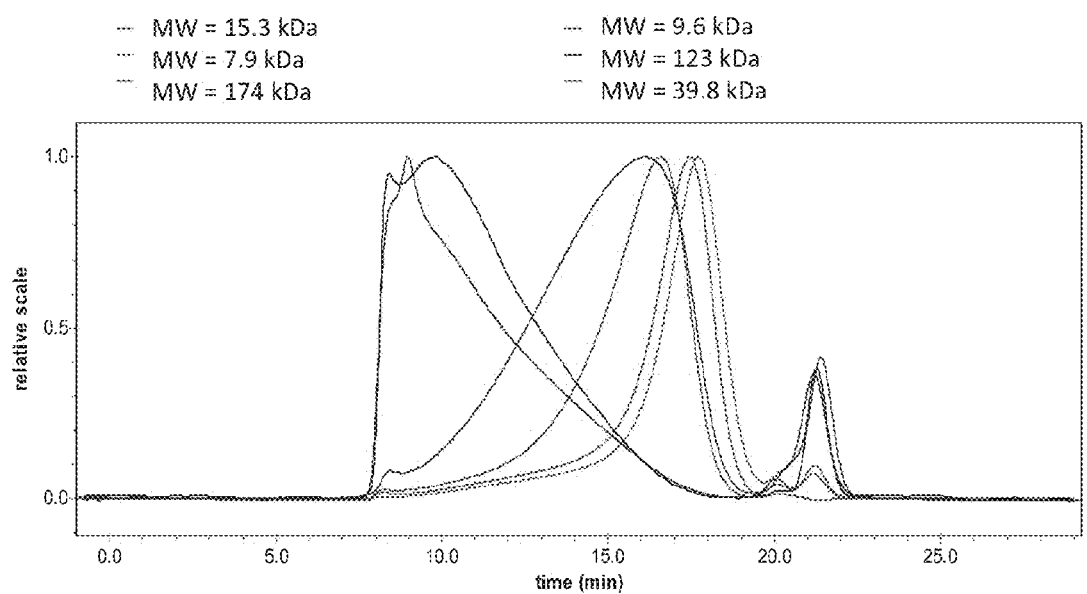
FIG. 12 shows an example of size exclusion chromatography refractive index overlay of NASP compositions according to certain embodiments.
Figure 13:
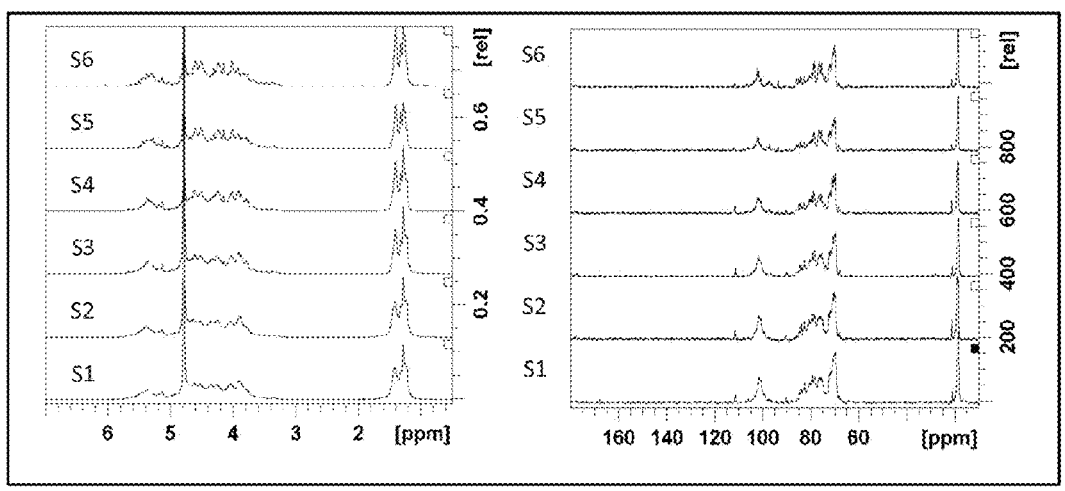
FIG. 13 shows an example of $^1$H-NMR and $^{13}$C-NMR used to characterize size-separated NASP compositions according to certain embodiments.

Size-fractionated fucoidans were prepared from F.v. fucoidan by ultra-filtration. Six size separated fractions were produced and studied. The molecular weights of each fraction were determined with SEC-MALLS and are summarized in Table 12. The overlaid refractive index chromatograms of the size separated fractions are shown in FIG. 12. The molecular weight of the fractions ranged from about 8 kD to about 170 kD. NMR spectra (FIG. 13) of six fractions S1-S6 were obtained and demonstrated similar structural properties. Using the molecular weight, sulfur content, and sugar composition, the degrees of polymerization (i.e., length of sugar chain) were calculated and are summarized in Table 12.

TABLE 12

Molecular weight and degree of sulfation of F.v. fucoidan separated by size-separated fractionation

| Fractions | Molecular Weight (kDa) | Degree of Polymerization |
|---|---|---|
| S1 | 174 | 840 |
| S2 | 124 | 590 |
| S3 | 40 | 200 |
| S4 | 15 | 70 |
| S5 | 10 | 50 |
| S6 | 8 | 40 |

Elucidation of NASP Structure Using 2-D and 3-D NMR

One and two-dimensional NMR spectra were acquired on the above described charge-separated fractions to elucidate molecular structure. In all charge-separated fractions except for C6, there was a significant peak overlap in the 1D and 2D NMR spectra indicating a mixture of sub-structures, which precluded specific peak assignment and elucidation of discrete structures.

Figure 14:
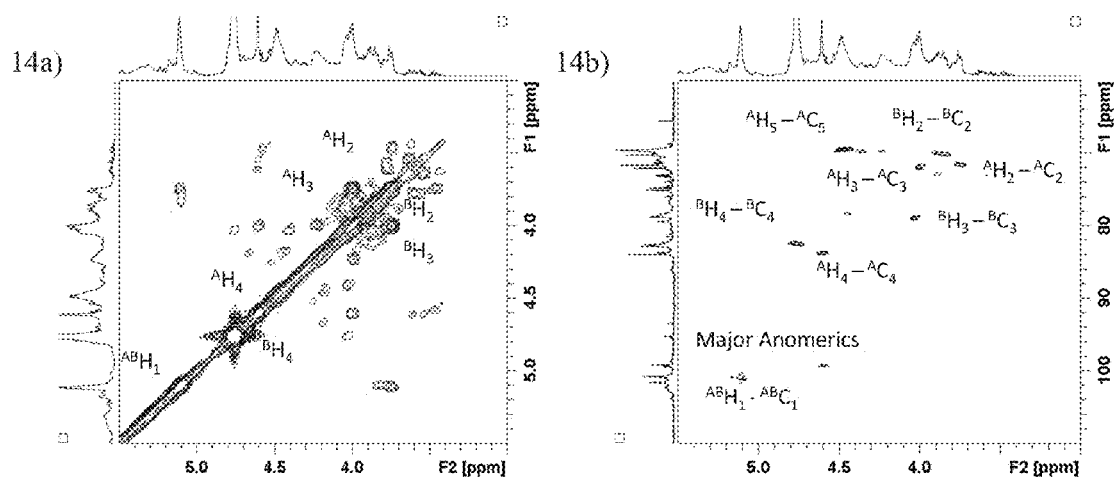
FIG. 14 shows examples of 2D-NMR used to characterize NASP compositions according to certain embodiments.
Figure 15:
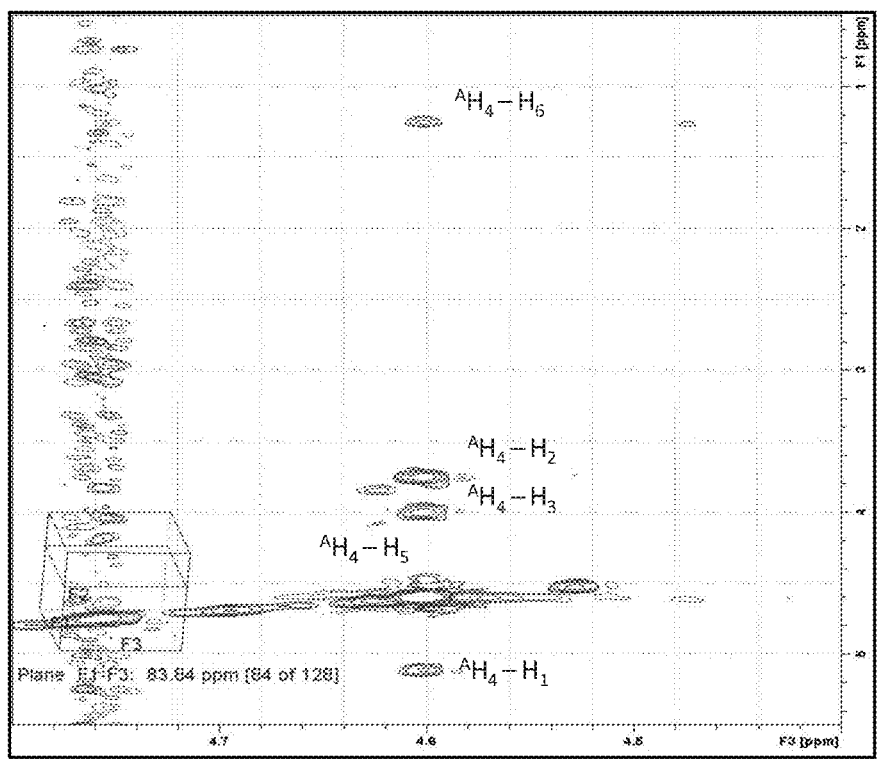
FIG. 15 shows an example 2D-plane of a 3D-NMR data set used to characterize NASP compositions according to certain embodiments.
Figure 16:
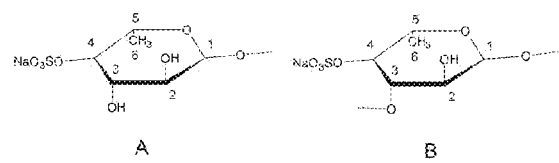
FIG. 16 illustrates an example of NASP sulfation and glycosidic bond configuration according to certain embodiments.
Figure 16:
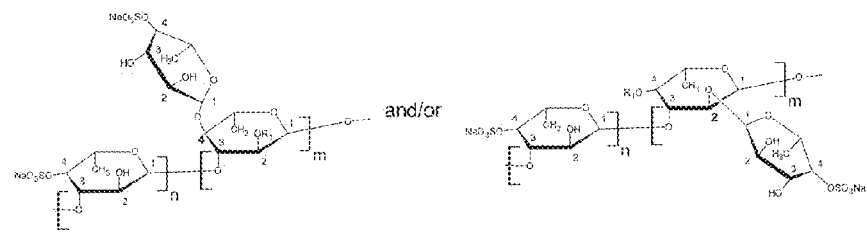

The structure of fraction C6 was elucidated. Fraction C6 obtained as described above was assigned by 2-D COSY (FIG. 14A) and HSQC spectra (FIG. 14B). The labels "C" and "H" are used to denote the atom in the NASP structure, a superscript A or B is used to denote the type of fucose residue and a subscript number to denote the position in the monosaccharide residue. Three-dimensional HSQC-TOCSY was also used to clarify peak assignments (FIG. 15). Fraction C6 included at least two kinds of fucose residues, A and B. The chemical shifts, which were calibrated by internal standard TMSP, are listed in Table 13. The chemical shifts of $^{A}H_4$ and $^{A}C_4$ are 4.60 ppm and 83.9 ppm, respectively. These relatively high chemical shifts indicate O-sulfation at the hydroxyl on $^{A}C_4$. The chemical shifts of other positions are relatively low indicating no substitutions. Thus, A residues are terminal 4-O-sulfated fucose residues. Both $^{B}H_4$ and $^{B}C_4$ also have large chemical shifts similar to those of the 4-position in the A residue, which indicates sulfation at the 4-position of the B residue. The chemical shift of $^{B}C_3$ has a value of 78.8 ppm, whereas that of the corresponding $^{B}H_3$ has a value of 4.03 ppm. These chemical shifts indicate that the 3-position is the linking position. Therefore, B residues are determined to be α-1-3 linked 4-O-sulfated fucose residues. The chemical structures of residues A and B are shown in FIG. 16. The cross peaks of residue A in the HSQC spectrum is relatively intense indicating an abundance of A residues in this fraction. Since A is a terminal residue, fraction C6 contains a highly branched polysaccharide with a backbone of B residues connected to branches composed of A residues. The ratio of B residues to A residues is about 1.4 indicating that about one in every 1.4 B residues has a branch with an A residue.

Figure 17:
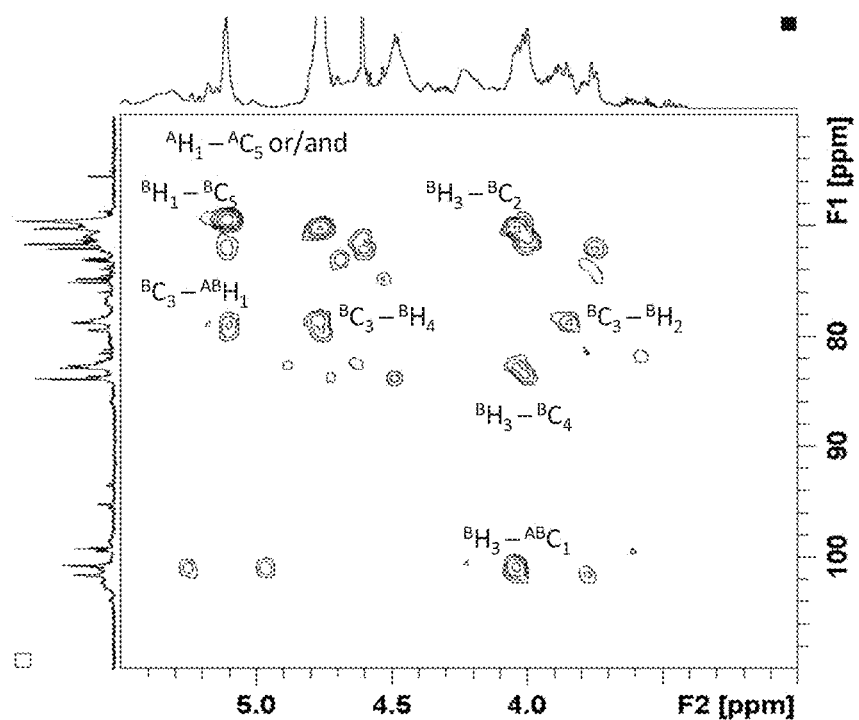
FIG. 17 shows another example of 2D-NMR used to characterize NASP compositions according to certain embodiments.

The structure of fraction C6 was also assigned by HMBC (FIG. 17). As depicted in FIG. 17, no unambiguous correlation was observed between A residues and B residues across the oxygen on the glycosidic bonds. The proton and carbon chemical shifts of position 1 in these two residues are close to each other. The cross peak labeled as $^{B}C_3$-$^{AB}H_1$ in FIG. 16 is the correlation between $^{B}C_3$ and $^{B}H_1$ or the correlation between $^{B}C_3$ and $^{A}H_1$, both pairs of which are separated by 3 bonds. The branching pattern was determined that most of the A and B residues are not directly linked to each other, and most of the B residues are not part of the branched chain. Thus, the major structure of this fraction was determined to be an α-1-3 linked, 4-O-sulfated, and highly branched polyfucan, in which the most branches are 4-O-sulfated fucose at 2 or 4 positions.

TABLE 13

Chemical shifts of residues in the structure of NASPs in fraction C6.

| Residues | Position 1 | Position 2 | Position 3 | Position 4 | Position 5 | Position 6 |
|---|---|---|---|---|---|---|
| | Proton chemical shifts (ppm) | | | | | |
| A | 5.11 | 3.75 | 4.00 | 4.60 | 4.49 | 1.24 |
| B | 5.10 | 3.83 | 4.03 | 4.76 | 4.49 | 1.27 |
| | Carbon chemical shifts (ppm) | | | | | |
| A | 100.4 | 71.6 | 71.7 | 83.9 | 69.5 | 18.6 |
| B | 100.9 | 70.1 | 78.8 | 82.5 | 69.5 | 18.6 |

Desulfation and Oversulfation of NASPs

Figure 18:
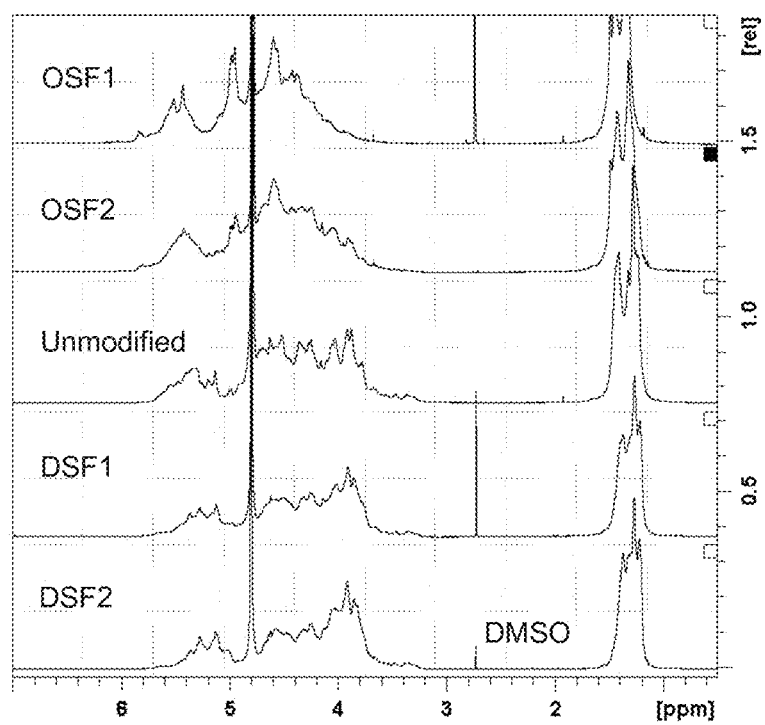
FIG. 18 shows an example of $^1$H-NMR used to characterize oversulfated and desulfated NASPs according to certain embodiments.

Fucoidans were desulfated and oversulfated using the method as described above. $^1$H NMR spectra of chemically modified fucoidans are shown in FIG. 18. $^1$H NMR spectra of oversulfated fucoidans (OSF) are shown at the top of FIG. 3. Oversulfated fucoidan sample 1 (OSF 1) was prepared with a high amount of sulfating reagent and oversulfated fuocidan sample 2 (OSF 2) was prepared with a low amount of sulfating reagent. $^1$H NMR spectra of desulfated fucoidans (DSF) are shown at the bottom of FIG. 18. Desulfated fucoidan sample 1 (DSF 1) was subjected to 1 hours of desulfation reaction. Desulfated fucoidan sample 2 (DSF2) was subjected to 2 hours of desulfation reaction. A sample of unmodified fucoidan was also analyzed and $^1$H NMR for unmodified fucoidan is depicted in FIG. 18 as a reference.

A comparison of the spectra reveals that most peaks in the range of 3.2-5.9 ppm gradually shifted from high to low frequency implying that the degree of sulfation follows a decreasing trend. The degree of sulfation calculated based on the sulfur measurements of these chemically modified fucoidans are listed in Table 14 and were consistent with the results from NMR analysis.

TABLE 14

Degree of sulfation and degree of polymerization of oversulfated and desulfated F.v. Fucoidan

| Sample | Degree of Sulfation | Molecular Weight (kDa) | Degree of Polymerization |
|---|---|---|---|
| Oversulfated Fucoidan 1 | 1.34 | 65 | 230 |
| Oversulfated Fucoidan 2 | 1.03 | 55 | 220 |
| Unmodified Fucoidan | 0.63 | 51 | 240 |
| Desulfated Fucoidan 1 | 0.50 | 24 | 120 |
| Desulfated Fucoidan 2 | 0.37 | 15 | 80 |

The molecular weight and degree of polymerization were also determined and are listed in Table 14. The results indicated that depolymerization occurred with desulfation, and the change in degree of depolymerization is reaction time dependent. On the other hand, the degree of polymerization of oversulfated fucoidans are similar to unmodified fucoidan which indicates that no depolymerization occurs during the oversulfation. The change in molecular weight are the result of the addition of sulfate groups.

Example 3

Chemical Makeup

The sulfur content was also used to characterize the tested fucoidans. L.j and E.m showed low sulfur content, but the quantitated low sulfur contents were partially affected by high alginate content, and thus, may not entirely be an indication of low sulfur contents in the fucoidans. For example, the sulfur content of L.j. fucoidan was adjusted from 5.8 to 8.5 wt % after alginate was excluded (other adjusted S % were shown in Table 5).

Impurities in NASP composition may affect NASP coagulation activity, increase the possibility of toxicity, and impact quality control in the processing. Thus, organic and inorganic impurities were analyzed.

Non-NASP polysaccharides are co-extracted with fucoidans in brown seaweed, such as alginate and laminaran. Alginate is composed of mannuronic and guluronic acid with 1-4 linkage and is neither pro- nor anti-coagulant in the concentration range relevant to the tested fucoidans. The carbonyl groups from alginate observed in the $^{13}$C-NMR spectra were integrated and the alginate contents were calculated. The alginate content can also be quantified by a uronic acid-specific assay, the carbazole assay. Laminaran is composed of glucose with 1-3 and 1-6 linkages. The glucose determined by monosaccharide composition analysis (Table 9) indicated the presence of laminaran. Glucose contents of the tested fucoidans was small and thus, laminaran content was negligible in the tested fucoidans.

Elemental analysis for nitrogen indicated protein content. All these fucoidans contained small amounts of proteins (N≤0.12%).

Other organic impurities could come from the manufacturing process, such as acetic acid, glycerol, etc. One-dimensional $^1$H-NMR with 2D ($^1$H-$^1$H and $^1$H-$^{13}$C) NMR were used to test for acetic acid and glycerol.

Table 15 shows the elemental analysis of select fucoidan samples. As shown in Table 15, inorganic impurities were only detected in trace amounts.

TABLE 15

Elemental analysis with ICP

| Species/Lots | L.j. Fucoidan | U.p. Fucoidan | E.m. Fucoidan | F.v. Fucoidan Lot 1 | F.v. Fucoidan Lot 2 | F.v. Fucoidan Lot 3 |
|---|---|---|---|---|---|---|
| Ag | <0.1 | <0.1 | 3.8 | 0.2 | <0.1 | <0.1 |
| Al | 17 | 74 | 743 | 16 | 13 | 5.1 [a] |
| As | <0.1 | <0.1 | 0.9 | 0.1 | <0.1 | <0.1 |
| B | <2.8 | 3.2 [a] | 4.7 [a] | <2.8 | <2.8 | <2.8 |
| Ba | 37 | 2.2 [a] | 8.7 [a] | 4.7 [a] | 2.7 [a] | 3.0 [a] |
| Be | <0.1 | <0.1 | <0.1 | <0.1 | <0.1 | <0.1 |
| Bi | <0.1 | <0.1 | <0.1 | <0.1 | <0.1 | <0.1 |
| Ca wt % | 1.8 | 0.1 | 0.9 | 0.2 | 0.1 | 0.1 |
| Cd | <0.1 | <0.1 | 0.8 | <0.1 | <0.1 | <0.1 |
| Co | <0.1 | <0.1 | <0.1 | <0.1 | <0.1 | <0.1 |
| Cu | <0.2 | 0.3 | 12.7 | 0.8 | 1.2 | 1.3 |
| Fe | 45 | 100 | 181 | 48 | 15 | 10 |
| Ge | <0.1 | <0.1 | <0.1 | <0.1 | <0.1 | <0.1 |
| Hg | <0.1 | <0.1 | 0.4 | <0.1 | <0.1 | <0.1 |
| Li | <0.1 | 0.2 | 0.1 | <0.1 | <0.1 | <0.1 |
| Mg | 901 | 1783 | 3848 | 1703 | 61 | 70 |
| Mn | 0.3 | 3.3 | 8.4 | 11.4 | 1.2 | 1.2 |

TABLE 15-continued

Elemental analysis with ICP

| Species/Lots | L.j. Fucoidan | U.p. Fucoidan | E.m. Fucoidan | F.v. Fucoidan | | |
|---|---|---|---|---|---|---|
| | | | | Lot 1 | Lot 2 | Lot 3 |
| Mo | 0.4 | <0.2 | <0.2 | <0.2 | <0.2 | <0.2 |
| Na wt % | 7.5 | 7.0 | 6.9 | 6.3 | 6.9 | 7.2 |
| Ni | 1.6 | 0.3 | 1.9 | 0.7 | 0.4 | 0.3 |
| P | 30 | 227 | 763 | 20 [a] | <26 | 12 [a] |
| Pb | <0.1 | 0.2 | 1.3 | 0.2 | <0.1 | <0.1 |
| S wt % | 5.8 | 10 | 6.0 | 8.7 | 9.1 | 9.9 |
| Theoretical S wt % of fucoidan [b] | 8.5 | 10.2 | 8.4 | 9.5 | 9.8 | 10.5 |
| Sb | <0.2 | <0.2 | <0.2 | <0.2 | <0.2 | <0.2 |
| Se | <0.1 | <0.1 | <0.1 | <0.1 | <0.1 | <0.1 |
| Si | 13 | 46 | 1238 | 140 | 275 | 80 |
| Sn | <0.2 | 4.2 | 0.3 | 0.2 | <0.2 | 0.3 |
| Sr | 344 | 103 | 168 | 226 | 177 | 194 |
| Ti | 14 | <6.7 | 11 | <6.7 | <6.7 | <6.7 |
| Zn | 1.4 [a] | 6.4 [a] | 23 | 5 [a] | 1.8 [a] | 1.8 [a] |

[a] indicates a read value between the LQD and lowest standard;
[b] the theoretical S wt % was calculated from S wt %, alginate content in Table 10, and the monosaccharide composition in Table 9.

Elemental Analysis

Thirty elements were analyzed using ICP (Tables 15 and 16). The sulfur contents of select fucoidans varied from 5.8% (wt %) for L.j. to 10% (wt %) for U.p. fucoidan. Sodium, which corresponded to the primary counter ion ranged from 6.3 to 7.5 wt %, while lesser amounts of calcium and magnesium were also observed: 1.8 and ≤0.1 wt % for L.j.; 0.9 and ≤0.4 wt % for E.m.; and ≤0.2% for other fucoidans, respectively. Arsenic is a toxin of interest for algae sourced fucoidans. Only trace amounts of As were detected, in which the highest value was 0.9 µg/g in E.m.; and other fucoidans contained ≤0.1 µg/g. The concentration of the other elements determined ranged from ≤0.00001% (0.1 µg/g) to 0.13%.

TABLE 16

Elemental analysis of As, Ca, Mg, Na, S, and theoretical S wt %.

| Species/Lots | L.j. Fucoidan | U.p. Fucoidan | E.m. Fucoidan | F.v. Fucoidan | | |
|---|---|---|---|---|---|---|
| | | | | Lot 1 | Lot 2 | Lot 3 |
| As (µg/g) | <0.1 | <0.1 | 0.9 | 0.1 | <0.1 | <0.1 |
| Ca wt % | 1.8 | 0.1 | 0.9 | 0.2 | 0.1 | 0.1 |
| Mg (µg/g) | 901 | 1783 | 3848 | 1703 | 61 | 70 |
| Na wt % | 7.5 | 7.0 | 6.9 | 6.3 | 6.9 | 7.2 |
| S wt % | 5.8 | 10 | 6.0 | 8.7 | 9.1 | 9.9 |
| Adjusted S wt % of fucoidan [a] | 8.5 | 10.2 | 8.4 | 9.5 | 9.8 | 10.5 |

[a] the theoretical S wt % was calculated from S wt %, alginate content in Table 4, and the monosaccharide composition in Table 3.

Colorimetric Titration

The sulfur contents from colorimetric titration (Table 17) were consistent with those from ICP. Carbon and hydrogen contents were similar among all fractions. Higher nitrogen content, 0.6 wt % was observed in E.m. and ≤0.1% of nitrogen was observed in all other fucoidans, implying E.m. fucoidan contained higher amounts of proteins.

TABLE 17

Elemental analysis with CNH analyzer and colometric titration

| Relative Area (%) | L.j. Fucoidan | U.p. Fucoidan | E.m. Fucoidan | F.v. Fucoidan | | |
|---|---|---|---|---|---|---|
| | | | | Lot 1 | Lot 2 | Lot 3 |
| C % | 27.8 | 23.4 | 27.8 | 25.3 | 26.2 | 26.4 |
| H % | 4.7 | 4.6 | 4.8 | 4.9 | 4.7 | 4.8 |
| N % | <0.05 | <0.05 | 0.6 | <0.05 | 0.1 | 0.07 |
| S % | 3.4 | 9.6 | 5.0 | 8.1 | 8.9 | 9.2 |

Example 4

Screening a Plurality of NASP (Fucoidan) Compositions

A plurality of fucoidan compositions was screened by evaluating coagulation activities, chemical makeups and NASP molecular structure to identify whether one or more of the fucoidan compositions may be suitable for treating a subject having a blood coagulation disorder. In screening the fucoidan compositions, each of the determined coagulation activities, chemical makeups and NASP molecular structure as described in Examples 1-3 were compared and ranked in the manner as described above. Since each category contributes to a total cumulative ranking, a (1) indicated the lowest possible rank and (4) was the highest rank in this example. Numerous factors were considered: procoagulant activity, anticoagulant activity, molecular size, polydispersity, structural heterogeneity, and impurities. The score for each category for the six selected NASPs is shown in Table 18.

In this example, activity was given the highest priority to screen NASP compositions. Structural heterogeneity and impurities were evaluated to identify NASP compositions which would be facile for quality control and manufacturing.

The procoagulant and anticoagulant activities, the ratio of these two activities, and the contact activation were all compared and ranked as shown in Table 18. The activation of contact pathway was ranked from (1) to (2), where (1) indicates the lowest concentration to activate contact pathway. Based on this comparison, the candidate having the highest activity and widest therapeutic window (i.e., F.v. fucoidan) was identified as suitable for treating a subject having a blood coagulation disorder.

Larger molecular weight fucoidans have lower solubility and reduced bioavailability. Therefore, the larger molecular weight fucoidans (E.m. and U.p. fucoidans) were assigned a lower ranking as compared to lower molecular weight fucoidans (L.j. and F.v. fucoidans). High polydispersity and structural heterogeneity can make quality control difficult and can complicate bioavailability and pharmacokinetics studies. Therefore, fucoidans having higher polydispersity and heterogeneity obtained lower rankings.

For example, based on the degree of the complexity of anomeric and the other carbon regions in the $^{13}$C-NMR spectra (as depicted for example in FIG. 6), the heterogeneity order was roughly ranked from (1) to (4), where (1) is the highest heterogeneity. The heterogeneity tested by $^{13}$C-NMR reflected not only the sugar compositions, which agreed with IC's results, but also complex sulfation patterns and linkages among different fucoidans. L.j. fucoidan had the highest heterogeneity and therefore was assigned a (1) ranking. F.v. fucoidan had the lowest heterogeneity and therefore was assigned a (4) ranking in this example.

Only alginate impurity was ranked in this example since all other impurities were negligible or were not detected. E.m. and L.j. fucoidan showed the largest amount of alginate whereas U.p. and F.v. fucoidans showed the smallest amount of alginate.

After ranking each category, shown in Table 18, the total cumulative ranking was calculated and the fucoidan(s) having the highest total cumulative ranking (i.e., F.v. fucoidans) were selected as suitable for treating a subject having a blood coagulation disorder.

TABLE 18

Screening a plurality of NASP (fucoidan) compositions

| Species/Lots | L.j. Fucoidan | U.p. Fucoidan | E.m. Fucoidan | F.v. Fucoidan Lot 1 | F.v. Fucoidan Lot 2 | F.v. Fucoidan Lot 3 |
|---|---|---|---|---|---|---|
| Procoagulant activity [a] | (3) | (2) | (1) | (3) | (3) | (3) |
| Anticoagulant [b] | (2) | (1) | (3) | (2) | (2) | (2) |
| Ratio [c] | (2) | (1) | (1) | (3) | (2) | (3) |
| Act of contact pathway [d] | (1) | (2) | (1) | (2) | (2) | (2) |
| Mw [e] | (3) | (2) | (1) | (3) | (3) | (3) |
| Monosaccharide composition [f] | (1) | (3) | (2) | (4) | (4) | (4) |
| Heterogeneity tested by NMR [g] | (1) | (3) | (2) | (4) | (4) | (4) |
| Alginate impurity [h] | (1) | (2) | (1) | (2) | (2) | (2) |
| Sum [i] | (14) | (16) | (12) | (23) | (22) | (23) |

[a] The procoagulant activities were ranked in a small range from (1) to (3), where (1) indicates the highest $EC_{50}$ concentration;
[b] The anticoagulant activities were ranked from (1) to (3), where (1) indicates the lowest concentration to increase 50% of clotting time;
[c] The ratio of pro- and anticoagulant activities were ranked from (1) to (3), where (1) indicates the lowest ratio;
[d] The activations of contact pathway were ranked from (1) to (2), where (1) indicates the lowest concentration to activate the pathway.
[e] Mw order ranked from (1) to (3), where (1) indicates the highest Mw;
[f] Based on the monosaccharide compositions listed in Table 3, their complexity was ranked from (1) to (4), where (1) is the most complex one;
[g] Based on degree of the complexity of anomerics and the other carbon regain in $^{13}$C-NMR spectra. The heterogeneity order was roughly ranked from (1) to (4), where (1) is the highest heterogeneity;
[h] Based on the data in Table 4, the alginate content were ranked from (1) to (2), where (1) is >10% and (2) <10%;
[i] Sum of the rankings for each candidate, the highest -scoring fucoidans (i.e., F.v. fucoidans) were selected as suitable for treating a subject having a blood coagulation disorder.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method of evaluating whether a composition comprising a NASP (non-anticoagulant sulfated polysaccharide) is suitable for treating a subject having a blood coagulation disorder, the method comprising:
assaying a blood or blood derived sample in the presence of the composition to determine coagulation activity;
determining:
the coagulation activity of the NASP from the assay;
the chemical makeup of the composition; and
the molecular structure of the NASP; and
evaluating whether the composition is suitable for treating a subject having a blood coagulation disorder based on the determined coagulation activity of the NASP from the assay, the chemical makeup of the composition and the determined molecular structure of the NASP.

2. The method according to claim 1, wherein determining coagulation activity of the composition comprises assessing the procoagulant activity of the composition.

3. The method according to claim 1, wherein determining coagulation activity of the composition comprises assessing the anticoagulant activity of the composition.

4. The method according to claim 1, wherein determining the coagulation activity of the composition comprises calculating the ratio of procoagulation activity to anticoagulation activity.

5. The method according to claim 1, wherein determining coagulation activity of the composition comprises assessing the TFPI-inhibiting activity of the NASP.

6. The method according to claim 1, wherein determining coagulation activity of the composition comprises determining the effect of the composition on contact pathway activation.

7. The method according to claim 1, wherein determining the molecular structure of the NASP comprises determining the molecular weight of the NASP.

8. The method according to claim 1, wherein determining the molecular structure of the NASP comprises determining the polydispersity of the NASP.

9. The method according to claim 1, wherein determining the molecular structure of the NASP comprises determining the monosaccharide content of the NASP.

10. The method according to claim 1, wherein determining the molecular structure of the NASP comprises determining the sulfur content of the NASP.

11. The method according to claim 1, wherein determining the molecular structure of the NASP comprises determining glycosidic bond configuration of the NASP.

12. The method according to claim 1, wherein determining the chemical makeup of the composition comprises determining the elemental components of the composition.

13. The method according to claim 1, wherein the method further comprises determining that a composition may be suitable for treating a subject having a blood coagulation disorder where the composition comprises:
- an $EC_{50}$ value for procoagulant activity of 0.3 µg/mL or less as determined by calibrated automated thrombography (CAT);
- a procoagulant window of 0.1 to 100 µg/mL;
- a ratio of the procoagulant activity to anticoagulant activity of the composition that is 10 or greater;
- a molecular weight of the NASP that is 160 kDa or less;
- a fucose content of the NASP that is 60% fucose or greater;
- an alginate content of the NASP that is 10% alginate or less;
- a weight percent of sulfur of the NASP is 8% sulfur by weight or greater; and
- a weight percent of impurities in the composition that is 0.1% impurities by weight or less.

14. The method according to claim 1, wherein the NASP is a fucoidan.

15. The method according to claim 14, wherein the fucoidan is a *Fucus vesiculosus* fucoidan.

16. A method of screening a plurality of compositions comprising a NASP for treating a subject having a blood coagulation disorder, the method comprising:
- assaying blood or blood derived samples in the presence of each of the plurality of compositions to determine coagulation activity of each composition;
- determining:
  - the coagulation activity of the NASP from each assay;
  - the chemical makeup of the plurality of compositions; and
  - the molecular structure of the NASP; and
- comparing the determined coagulation activities of the NASP from each assay, the chemical makeups of the plurality of compositions and the molecular structure of the NASP; and
- identifying whether one or more of the plurality of compositions may be suitable for treating a subject having a blood coagulation disorder.

17. A system for screening a plurality of compositions comprising a NASP, the system comprising:
- a processor comprising memory operably coupled to the processor, wherein the memory includes instructions stored thereon, the instructions comprising:
  - an algorithm for assessing coagulation activity of the NASP from an assay of a blood or blood derived sample in the presence of each of the plurality of compositions;
  - an algorithm for assessing chemical makeup of the plurality of compositions;
  - algorithm for assessing molecular structure of the NASP;
  - instructions for comparing coagulation activity of the NASP from the assay and the chemical makeup of the plurality of compositions and the molecular structure of the NASP; and
  - instructions for identifying whether one or more of the plurality of compositions may be suitable for treating a subject having a blood coagulation disorder.

18. A NASP composition suitable for treating a subject having a blood coagulation disorder, the composition comprising one or more NASPs, wherein the NASP composition comprises 50% or greater by weight NASPs that comprise one or more properties selected from the group consisting of:
- an $EC_{50}$ value for procoagulant activity of the NASP composition that is 0.5 µg/mL or less as determined by calibrated automated thrombography (CAT);
- a procoagulant window of the NASP composition that ranges from 0.1 to 100 µg/mL;
- a ratio of procoagulant activity to anticoagulant activity that is 10 or greater;
- an $EC_{50}$ for TFPI-inhibiting activity that is 0.4 µg/mL or less;
- a molecular weight that is 160 kDa or less;
- a degree of polymerization that ranges from 70 to 200;
- a ratio of linear saccharide residues to branching saccharide residues that is 1.4 or less;
- a fucose content that is 60% or greater by weight;
- an alginate content that is 10% or less by weight;
- a degree of sulfation that is 0.5 or greater; and
- a sulfur content that is 8% sulfur or greater by weight.

19. The composition according to claim 18, wherein the composition comprises 90% or greater by weight NASPs that comprise one or more properties selected from the group consisting of:
- an $EC_{50}$ value for procoagulant activity of the NASP composition that is 0.5 µg/mL or less as determined by calibrated automated thrombography (CAT);
- a procoagulant window of the NASP composition that ranges from 0.1 to 100 µg/mL;
- a ratio of procoagulant activity to anticoagulant activity that is 10 or greater;
- an $EC_{50}$ for TFPI-inhibiting activity that is 0.4 µg/mL or less as determined by calibrated automated thrombography (CAT);
- a molecular weight that is 160 kDa or less;
- a degree of polymerization that ranges from 70 to 200;
- a ratio of linear saccharide residues to branching saccharide residues that is 1.4 or less;
- a fucose content that is 60% or greater by weight;
- an alginate content that is 10% or less by weight;
- a degree of sulfation that is 0.5 or greater; and
- a sulfur content that is 8% sulfur or greater by weight.

20. The method according to claim 1, wherein the method comprises assaying the composition by one or more of activated partial thromboplastin time (aPTT) assay, calibrated automated thrombography (CAT) and dilute prothrombin (dPT) assay.

21. The method according to claim 1, wherein the composition comprises a purified NASP.

* * * * *